(12) United States Patent
Baumgartner et al.

(10) Patent No.: US 10,036,058 B2
(45) Date of Patent: Jul. 31, 2018

(54) PORTABLE TESTING DEVICE FOR ANALYZING BIOLOGICAL SAMPLES

(71) Applicant: Agdia, Inc., Elkhart, IN (US)

(72) Inventors: Mark B. Baumgartner, Alexandria, MN (US); Cory D. Hodgson, Alexandria, MN (US); Andrew L. Bristow, Alexandria, MN (US); Paul A. Syverson, Glenwood, MN (US); Grant L. Pexsa, Alexandria, MN (US); Christopher T. Davis, Alexandria, MN (US); Rich Schoeneck, Alexandria, MN (US); Duane Brown, Buffalo, MN (US); Darren Cook, Alexandria, MN (US)

(73) Assignee: AGDIA INC., Elkhart, IN (US)

( * ) Notice: Subject to any disclaimer, the term of this patent is extended or adjusted under 35 U.S.C. 154(b) by 22 days.

(21) Appl. No.: 15/027,797

(22) PCT Filed: Oct. 7, 2014

(86) PCT No.: PCT/US2014/059487
§ 371 (c)(1),
(2) Date: Apr. 7, 2016

(87) PCT Pub. No.: WO2015/054245
PCT Pub. Date: Apr. 16, 2015

(65) Prior Publication Data
US 2016/0265040 A1    Sep. 15, 2016

Related U.S. Application Data

(60) Provisional application No. 61/926,759, filed on Jan. 13, 2014, provisional application No. 61/887,754, filed on Oct. 7, 2013.

(51) Int. Cl.
*B01L 3/00*   (2006.01)
*B01L 7/00*   (2006.01)
(Continued)

(52) U.S. Cl.
CPC ........ *C12Q 1/6848* (2013.01); *B01L 3/50851* (2013.01); *B01L 7/00* (2013.01);
(Continued)

(58) Field of Classification Search
CPC ........... B01L 2200/10; B01L 2200/141; B01L 2300/021; B01L 2300/024;
(Continued)

(56) References Cited

U.S. PATENT DOCUMENTS 5,184,020 A    2/1993  Hearst et al.
5,475,610 A   12/1995  Atwood et al.
(Continued)

FOREIGN PATENT DOCUMENTS

CA    2505886 A1    5/2004
CN    201035009     3/2008
(Continued)

OTHER PUBLICATIONS

State Intellectual Property Office of People'S Republic of China; Translation of First Office Action issued in connection to correspondence CN Application No. 201480064137.1; dated Jul. 27, 2017; 5 pagers; China.
(Continued)

*Primary Examiner* — Jennifer Wecker
(74) *Attorney, Agent, or Firm* — Kilpatrick Townsend & Stockton LLP

(57) ABSTRACT

A portable testing device includes a housing with an integrated touchscreen display and a receptacle in which a sample holder containing a biological sample and reagent mixture can be placed. The portable testing device further
(Continued)

includes an optical assembly positioned in the housing, an electronic assembly that is configured to receive data from the optical assembly and transmit it for display on the touchscreen display, and a power supply in the housing to power the portable testing device. The optical assembly includes an excitation filter that extends across the entire optical assembly and an emission filter that extends across the entire optical assembly.

14 Claims, 75 Drawing Sheets

(51) Int. Cl.
| | | |
|---|---|---|
| *B01L 9/06* | (2006.01) | |
| *G01N 21/64* | (2006.01) | |
| *G01N 21/25* | (2006.01) | |
| *C12Q 1/6848* | (2018.01) | |
| *G01N 21/03* | (2006.01) | |
| *C12Q 1/68* | (2018.01) | |

(52) U.S. Cl.
CPC ............ *B01L 9/06* (2013.01); *G01N 21/0332* (2013.01); *G01N 21/253* (2013.01); *G01N 21/645* (2013.01); *G01N 21/6428* (2013.01); *B01L 2200/10* (2013.01); *B01L 2200/141* (2013.01); *B01L 2300/021* (2013.01); *B01L 2300/024* (2013.01); *B01L 2300/025* (2013.01); *B01L 2300/041* (2013.01); *B01L 2300/0654* (2013.01); *G01N 2021/0325* (2013.01); *G01N 2021/6441* (2013.01); *G01N 2021/6482* (2013.01); *G01N 2201/0221* (2013.01); *G01N 2201/0231* (2013.01)

(58) Field of Classification Search
CPC ......... B01L 2300/025; B01L 2300/041; B01L 2300/0654; B01L 3/50851; B01L 7/00; B01L 9/06; C12Q 1/6848; G01N 2021/0325; G01N 2021/6441; G01N 2021/6482; G01N 21/0332; G01N 21/253; G01N 21/6428; G01N 21/645; G01N 2201/0221; G01N 2201/0231
See application file for complete search history.

(56) References Cited

U.S. PATENT DOCUMENTS

| | | | |
|---|---|---|---|
| 5,503,721 A | 4/1996 | Hearst et al. | |
| 5,585,069 A | 12/1996 | Zanzucchi et al. | |
| 5,683,661 A | 11/1997 | Hearst et al. | |
| 5,854,967 A | 12/1998 | Hearst et al. | |
| 6,043,880 A | 3/2000 | Andrews et al. | |
| 6,084,683 A | 7/2000 | Bruno et al. | |
| 6,258,319 B1 | 7/2001 | Hearst et al. | |
| 6,369,893 B1 | 4/2002 | Christel et al. | |
| 6,461,567 B1 | 10/2002 | Hearst et al. | |
| 6,565,815 B1 | 5/2003 | Chang et al. | |
| 6,664,113 B2 | 12/2003 | Kurihara et al. | |
| 6,680,025 B2 | 1/2004 | Hearst et al. | |
| 6,699,713 B2 | 3/2004 | Benett et al. | |
| 6,828,567 B2 | 12/2004 | Amirkhanian et al. | |
| 6,835,574 B2 | 12/2004 | Neilson et al. | |
| 6,940,598 B2 | 9/2005 | Christel et al. | |
| 6,995,841 B2 | 2/2006 | Scott et al. | |
| 7,186,989 B2 | 3/2007 | Farmer et al. | |
| 7,315,376 B2 | 1/2008 | Bickmore, Jr. et al. | |
| 7,355,194 B2 | 4/2008 | Tobimatsu | |
| 7,483,805 B2 | 1/2009 | Sparks et al. | |
| 7,511,811 B2 | 3/2009 | Scott et al. | |
| 7,846,315 B2 | 12/2010 | Amirkhanian et al. | |
| 8,089,628 B2 | 1/2012 | Scott et al. | |
| 8,153,064 B2 | 4/2012 | Doebler, II et al. | |
| 8,380,541 B1 | 2/2013 | Holmes | |
| 8,460,531 B2 | 6/2013 | Amirkhanian et al. | |
| 2004/0257753 A1 | 12/2004 | Rossini | |
| 2006/0066850 A1* | 3/2006 | Kimura | G01J 3/10 356/328 |
| 2011/0207137 A1 | 8/2011 | Malik et al. | |
| 2011/0291609 A1 | 12/2011 | Bae | |
| 2011/0300550 A1 | 12/2011 | Tanigami | |
| 2012/0100551 A1 | 4/2012 | Kojima et al. | |
| 2012/0123686 A1 | 5/2012 | Xiang et al. | |
| 2012/0145587 A1 | 6/2012 | Yeo et al. | |
| 2012/0171756 A1 | 7/2012 | Doebler, II et al. | |
| 2012/0197622 A1 | 8/2012 | Jain | |
| 2013/0011912 A1* | 1/2013 | Battrell | G01N 21/645 435/287.2 |
| 2013/0085680 A1 | 4/2013 | Arlen et al. | |
| 2013/0156286 A1 | 6/2013 | Holmes | |
| 2013/0210127 A1 | 8/2013 | Williams et al. | |
| 2014/0045186 A1 | 2/2014 | Gubatayao et al. | |
| 2015/0111287 A1* | 4/2015 | Rawle | B01L 7/52 435/287.2 |
| 2015/0233828 A1* | 8/2015 | Courtney | G01N 21/6486 250/459.1 |

FOREIGN PATENT DOCUMENTS

| | | |
|---|---|---|
| EP | 0640828 A1 | 3/1995 |
| EP | 2605001 | 6/2013 |
| WO | WO2009103003 A2 | 8/2009 |
| WO | WO2011119404 A1 | 9/2011 |
| WO | 2012142516 A1 | 10/2012 |
| WO | WO2013049702 A2 | 4/2013 |
| WO | WO2013049709 A1 | 4/2013 |
| WO | 2013133725 | 9/2013 |
| WO | 2015054245 | 4/2015 |

OTHER PUBLICATIONS

European Patent Office; European Search Report issued in connection to corresponding EP Application No. 14852273.3; dated Jul. 19, 2017; 15 pages; Europe.

European Patent Office; Translation of Abstract to CN201035009; 1 page; Sep. 16, 2017; Europe.

International Search Report and Written Opinion from PCT Application Serial No. PCT/US2014/059487, dated Mar. 11, 2015, 18 pages.

European Patent Office; European Extended Search Report issued in connection to corresponding EP Application No. 14852273.3; dated Oct. 10, 2017; 16 pages; Europe.

* cited by examiner

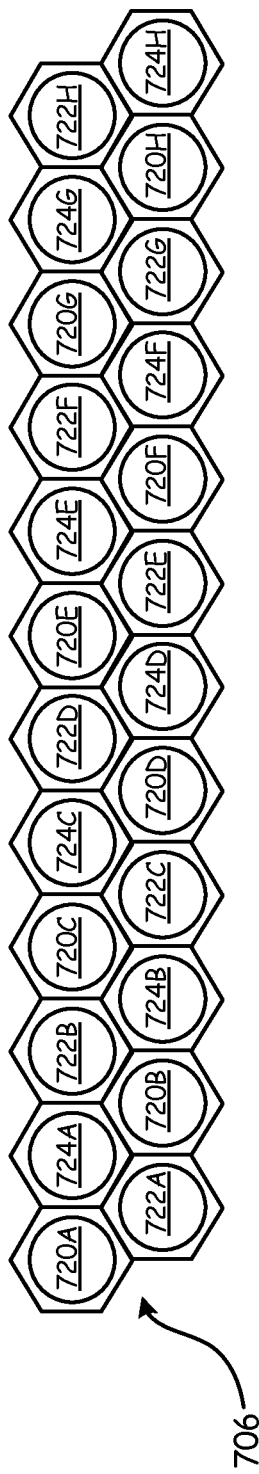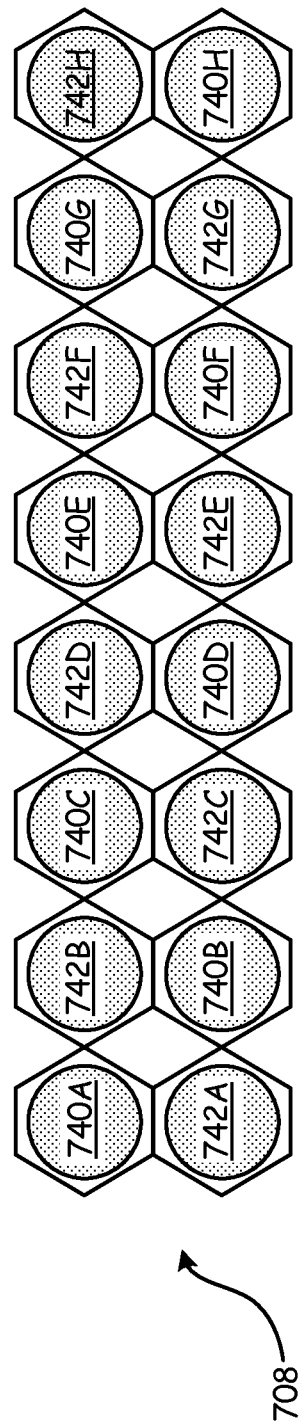
Fig. 26A
Fig. 26B

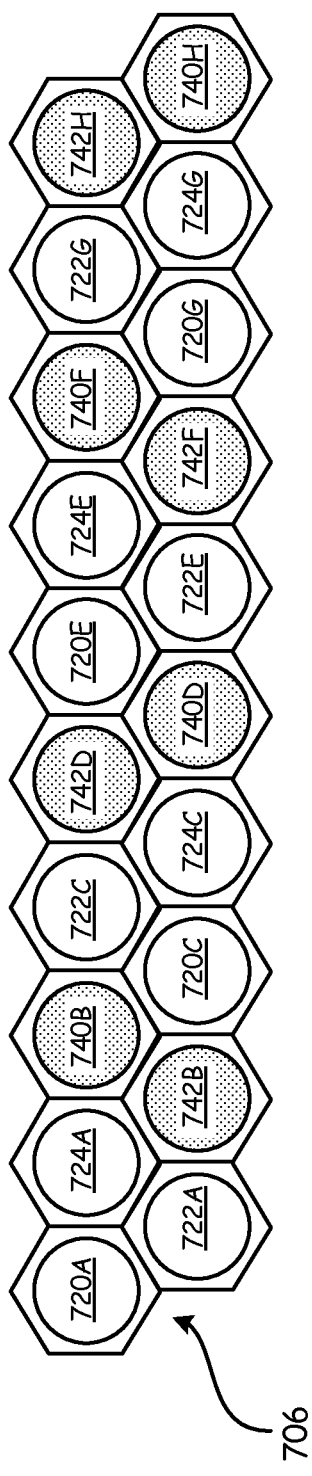
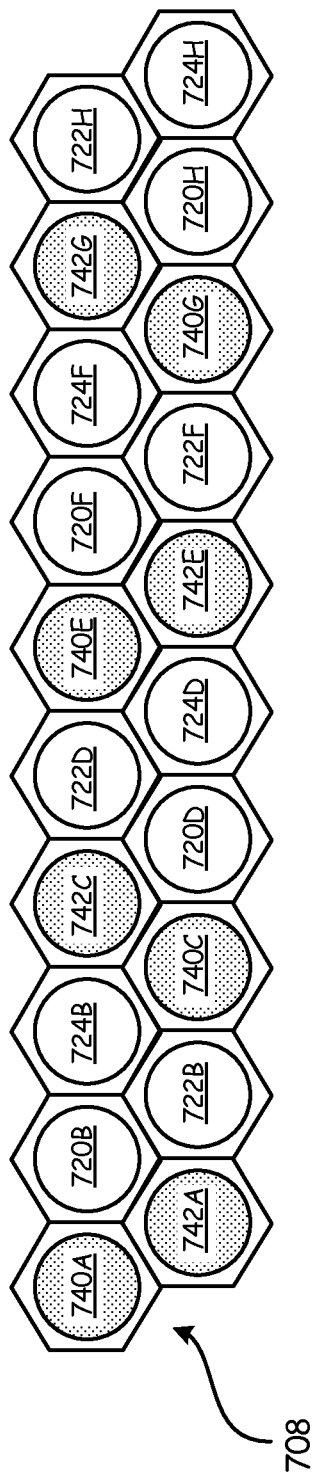
Fig. 27A
Fig. 27B

PORTABLE TESTING DEVICE FOR ANALYZING BIOLOGICAL SAMPLES

BACKGROUND

The present invention relates to devices that are capable of analyzing biological samples, and in particular, to a portable testing device that is capable of being used in the field.

Biological samples are typically tested in laboratories after the biological samples are collected in the field. A number of steps are taken to prepare the sample after it has been collected, including mixing the sample with reaction buffers, dyes, and any other chemical solutions needed to prepare the sample for testing. During or after sample preparation, testing equipment also needs to be prepared. This can include warming up the equipment, calibrating the equipment for the specific tests to be run, and running through any other initial procedures required for the specific testing equipment being used. Once the sample and the equipment are prepared, the prepared sample can be placed in the equipment for testing.

The typical process for testing biological samples described above has significant disadvantages. One disadvantage is that biological samples need to be collected in the field, brought into the laboratory, and then tested. This can present the following issues. One, the biological sample can be contaminated between the times when it was collected and time that it is to be tested. Two, it can be discovered that not enough biological sample was collected in the field, preventing the testing from being complete. Three, it can be later discovered that the biological samples that were taken are otherwise unsuitable for testing. When a biological sample is unsuitable for testing for any of the above reasons, an additional biological sample will need to be collected in order to complete the testing. This requires additional time, money, and other resources to complete.

SUMMARY

A portable testing device includes a housing with an integrated touchscreen display and a receptacle in which a sample holder containing a biological sample and reagent mixture can be placed. The portable testing device further includes an optical assembly positioned in the housing, an electronic assembly that is configured to receive data from the optical assembly and transmit it for display on the touchscreen display, and a power supply in the housing to power the portable testing device. The optical assembly includes an excitation filter that extends across the entire optical assembly and an emission filter that extends across the entire optical assembly.

BRIEF DESCRIPTION OF THE DRAWINGS

FIG. 26A is a side view of a first side of the optical assembly according to a first configuration.

FIG. 26B is a side view of a second side of the optical assembly according to the first configuration.

FIG. 27A is a side view of a first side of the optical assembly according to a second configuration.

FIG. 27B is a side view of a second side of the optical assembly according to the second configuration.

DETAILED DESCRIPTION

In general, the present invention is a portable testing device for analyzing biological samples. The portable testing device can be taken into the field to test biological samples as they are collected. This is advantageous over prior art systems, as it allows a user to test biological samples as the user is collecting them. This can prevent problems with contamination and degradation of biological samples due to transportation to a laboratory for testing, later discovery that not enough sample was taken, or later discovery that the collected biological sample is otherwise unsuitable for use. Allowing a user to test the biological sample in the field can save time, money, and resources. Testing in the field also provides the ability for rapid safety response if test results indicate a pathogen or toxin that may be harmful.

In the embodiments described below, the portable testing device is capable of testing biological samples with an isothermal amplification process, such as EnviroLogix's DNAble® chemistry or LAMP chemistry. This eliminates the need for thermocycling as a means to amplify nucleic acid products for endpoint detection. This allows a user to obtain data from the biological sample while the test is being run. The portable testing device displays this data on a screen on the portable testing device or on a tablet computer so that a user can view the results of the test in the field.

Allowing a user to view the results of the test in the field is advantageous, as the user can then make an informed decision of whether additional tests are needed. Further, if testing indicates that there is a pathogen or toxin in the biological sample, a user can initiate proper safety protocol right away to protect against the pathogen or toxin. In alternate embodiments, the portable testing device is also capable of incorporating a thermocycler to allow for the use of non-isothermal polymerase chain reaction (PCR) chemistries and result in qPCR and end-point analysis.

Portable Testing Device 100 with Optical Assembly 156

Figure 1:
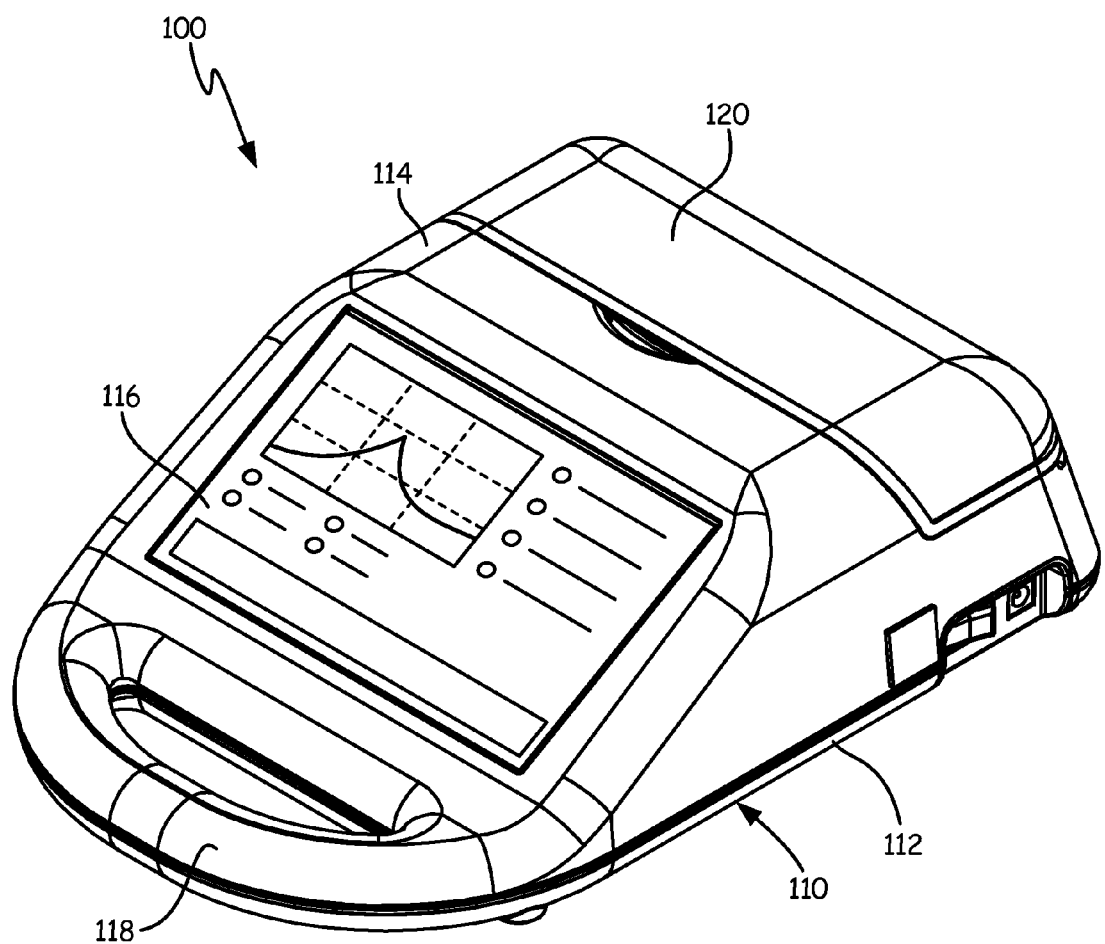
FIG. 1 is a perspective view of a portable testing device.

FIG. 1 is a perspective view of portable testing device 100. Portable testing device 100 includes housing 110 (including first housing portion 112 and second housing portion 114), display 116, handle 118, lid 120, and receptacle 122 (shown in FIG. 4A).

Portable testing device 100 is used to analyze biological samples that have been mixed with a reaction mixture (also referred to as a biological sample and reagent mixture). Housing 110 forms the body of portable testing device 100. Housing 110 includes first housing portion 112 and second housing portion 114. First housing portion 112 forms a base portion of portable testing device 100 and second housing portion 114 forms a top portion of portable testing device 100. Located on a front top side of housing 110 is display 116. Display 116 is a touchscreen display in the embodiment shown, but can be any suitable display in alternate embodiments. A user can use display 116 to select test protocol and set up the parameters for tests that will be run in portable testing device 100. A user can also use display 116 to provide sample and assay traceability information to portable testing device 100. Display 116 will also display data that is collected during testing.

Housing 110 further includes handle 118. Handle 118 is located on a front side of housing 110 in the embodiment shown, but can be located in any suitable location in alternate embodiments. Handle 118 is shown as an integrated handle with housing 110 in the embodiment shown, but can be attached to portable testing device 100 in any suitable manner in alternate embodiments. Handle 118 is included on portable testing device 100 so that portable testing device 100 can be easily transported in the field.

Housing 110 also includes lid 120. Lid 120 is located on a top side of housing 110 in the embodiment shown, but can be located in any suitable location in alternate embodiments. Lid 120 is included on portable testing device 100 to cover receptacle 122 (shown in FIG. 4A). Biological samples that are to be tested are loaded into a sample holder that can then be placed in receptacle 122. Lid 120 covers receptacle 122 to prevent contamination from entering into receptacle 122 when portable testing device 100 is being used in the field. Lid 120 further prevents radiation from escaping out of portable testing device 100 and prevents ambient light from entering into portable testing device 100 when testing is being completed. Lid 120 can be moved between an open and closed position and can be held in the closed position with any suitable means. In the embodiment shown, lid 120 is held in a closed position with magnets. When lid 120 is in a closed position, it puts pressure on the sample holder that is placed in a heat block in portable testing device 100. This improves engagement and heat transfer between the sample holder and the heat block in portable testing device 100.

Portable testing device 100 is designed for use in the field and provides many advantages for such use. Biological materials that are collected in the field can be tested in the field as they are collected. This alleviates concerns about contamination or degradation of the biological sample, as there is no need to transport the biological sample back to a laboratory for testing. Further, portable testing device 100 allows a user to quickly react to results from tests that are run in the field. If a test is inconclusive, additional biological material can be collected and sampled right away. Further, if testing indicates that there is a pathogen or toxin in the sample, a user can initiate proper safety protocol right away to protect against the pathogen or toxin.

Portable testing device 100 includes a number of features that make it suitable for use in the field. Handle 118 is included to easily transport the device. Display 116 is integrated into portable testing device 100 so that portable testing device 100 can act as an all-in-one system, as portable testing device 100 is capable of testing a biological sample, processing the data that is collected, and displaying the data on display 116. Display 116 eliminates the need for portable testing device 100 to be connected to another machine or computer to process and display the results of testing. This can allow a user to avoid having to carry an additional device in the field or having to wait till they get back to a laboratory to read the data. Portable testing device 100 includes all of the features that are necessary for testing, processing, and displaying results of the tests in a compact all-in-one device.

Figure 2A:
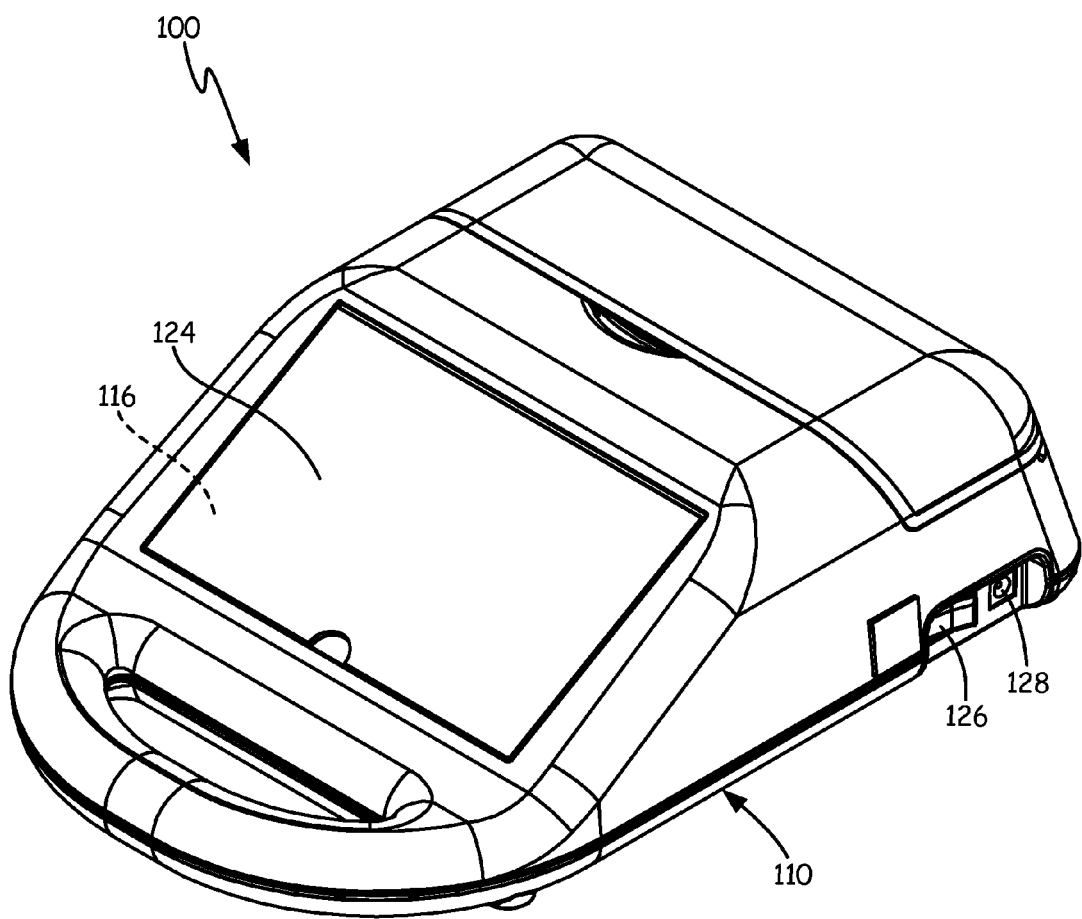
FIG. 2A is a perspective view of a top side of the portable testing device when a cover is placed over a display.
Figure 2B:
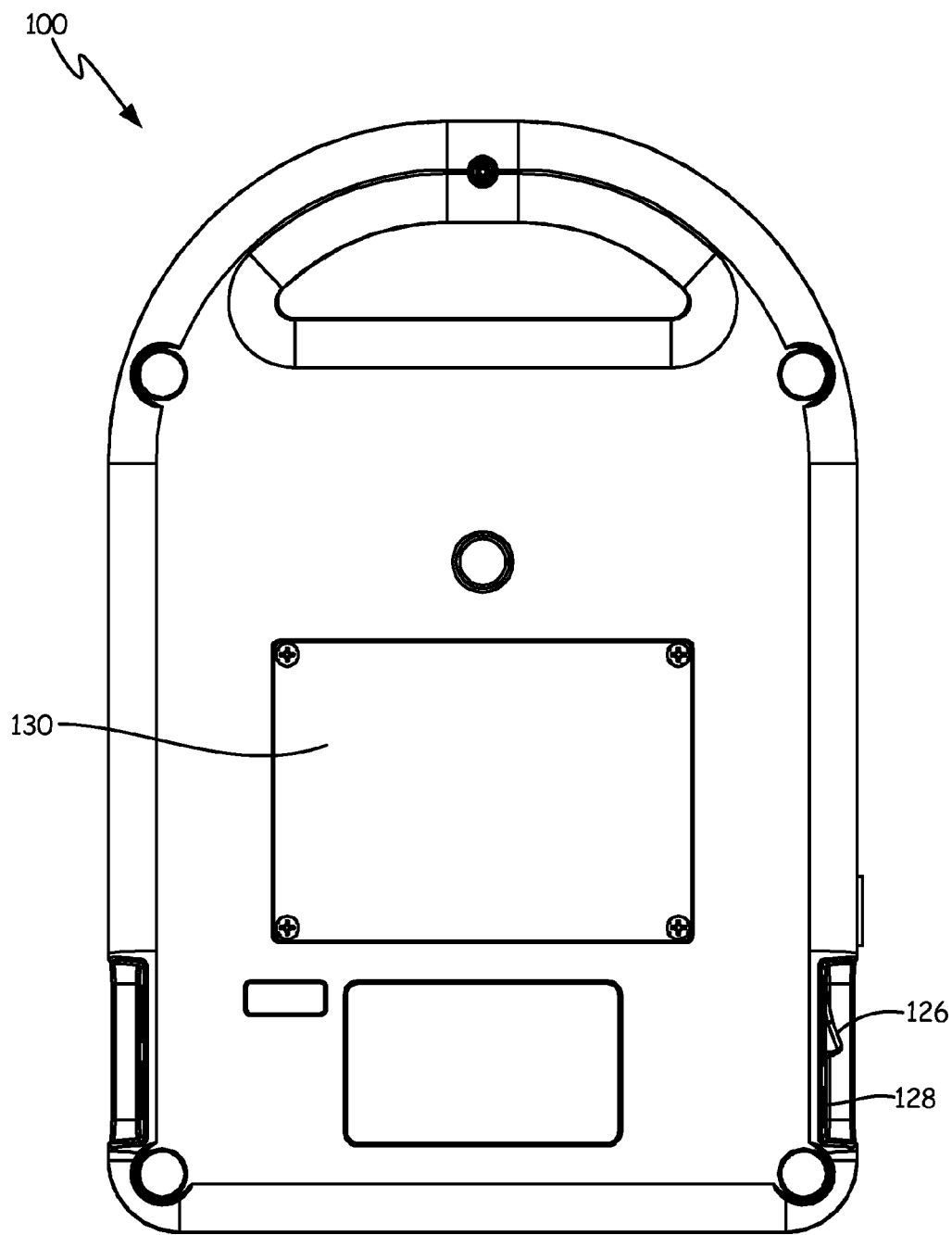
FIG. 2B is a bottom plan view of the portable testing device.

FIG. 2A is a perspective view of a top side portable testing device 100 when cover 124 is placed over display 116. FIG. 2B is a bottom plan view of portable testing device 100. Portable testing device 100 includes housing 110, display 116 (not shown in FIGS. 2A-2B), cover 124, power switch 126, power jack 128, and battery lid 130.

Housing 110 forms the body of portable testing device 100. Display 116 is positioned on a top front portion of housing 110. Display 116 is a touchscreen display and a user can use display 116 to select test protocol and to view data collected during testing. Cover 124 is provided to cover and protect display 116. Portable testing device 100 is designed for use in the field, so there is a significant risk that display 116 could be damaged if it was exposed when portable testing device 100 was being transported in the field. Cover 124 forms an interference fit with housing 110 over display 116. Cover 124 can be positioned over display 116 and snapped into place so that it is retained during transportation of portable testing device 100. Cover 124 protects display 116 from damage during transportation of portable testing device 100. Cover 124 can be removed from display 116 using a notch that is located along a perimeter portion of cover 124. A user can place a finger in the notch and pull cover 124 off of display 116.

Portable testing device 100 further includes power switch 126 and power jack 128 located on a side of housing 110. Power switch 126 can be used by a user to turn portable testing device 100 on and off. Power jack 128 is used to connect portable testing device 100 to a power source so that a battery in portable testing device 100 can be charged. Battery lid 130 holds the battery in portable testing device 100 and can be removed to access the battery.

Providing cover 124 over display 116 is advantageous, as display 116 could be easily damaged when portable testing device 100 is being used in the field. Display 116 is a touchscreen display that acts as the main user interface between a user and portable testing device 100, thus damage to display 116 could affect overall operation of portable testing device 100. Protecting display 116 with cover 124 prevents display 116 from being damaged. Further, powering portable testing device 100 with a battery is advantageous, as it allows portable testing device 100 to be used in the field.

Figure 3A:
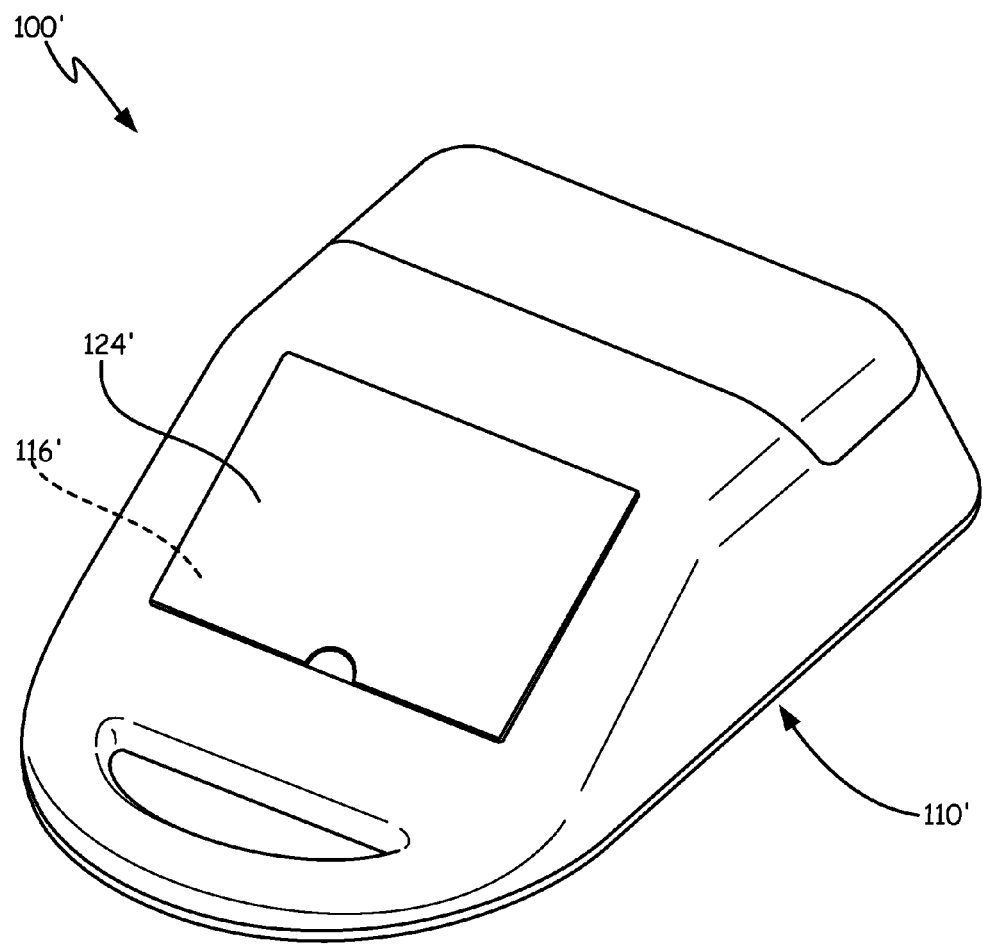
FIG. 3A is a perspective view of a top side of an alternate design of the portable testing device when a cover is placed over a display.
Figure 3B:
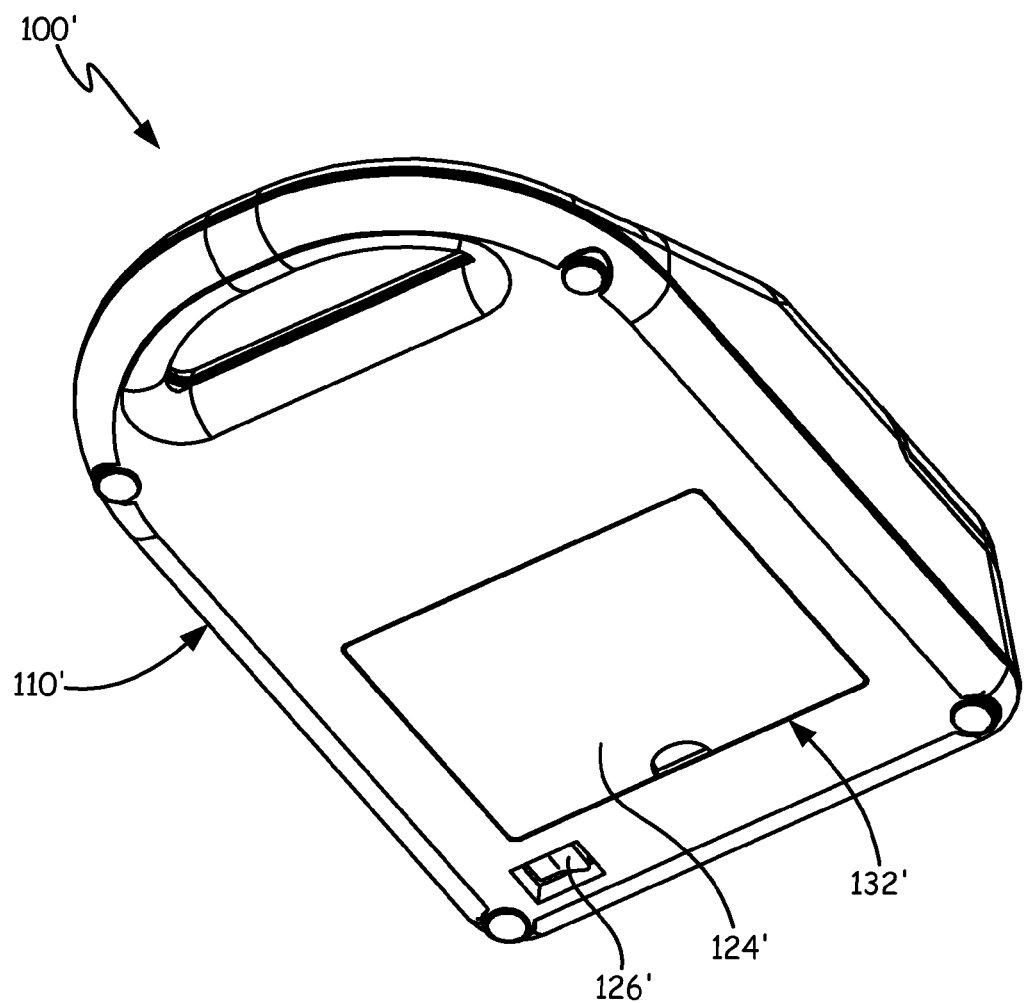
FIG. 3B is a perspective view of a bottom side of the alternate design of the portable testing device when the cover is stored in a recess on the bottom side of the portable testing device.

FIG. 3A is a perspective view of a top side of an alternate design of portable testing device 100' when cover 124' is placed over display 116'. FIG. 3B is a perspective view of a bottom side of the alternate design of portable testing device 100' when cover 124' is stored in recess 132' on the bottom side of portable testing device 100'. Portable testing device 100' includes housing 110', display 116' (not shown in FIGS. 3A-3B), cover 124', power switch 126', and recess 132'.

Housing 110' forms the body of portable testing device 100'. Display 116' is positioned on a top front portion of housing 110'. Cover 124' forms an interference fit with housing 110' over display 116'. Cover 124' can be positioned over display 116' and snapped into place so that it is retained during transportation of portable testing device 100'. Cover 124' protects display 116' from damage during transportation of portable testing device 100'. Cover 124' can be removed from display 116' using a notch that is located along a perimeter portion of cover 124'. A user can place a finger in the notch and pull cover 124' off of display 116'.

When portable testing device 100' is being used, cover 124' can be stored in recess 132'. Recess 132' is built into a bottom side of portable testing device 100' and is shaped to fit cover 124'. Cover 124' forms an interference fit with recess 132' and can be snapped into place in recess 132'. When portable testing device 100' is no longer being used, cover 124' can be removed from recess 132' using the notch that is located along the perimeter of cover 124' to pull cover 124' out of recess 132'. Power switch 126' is also positioned on the bottom side of portable testing device 100'. Power switch 126' can be used to turn portable testing device 100' on and off.

Providing cover 124' over display 116' is advantageous, as display 116' could be easily damaged when portable testing device 100' is being used in the field. Protecting display 116' with cover 124' prevents display 116' from being damaged. Further, providing recess 132' to store cover 124' is advantageous, as it allows a user to easily store cover 124' when portable testing device 100' is being used. This prevents a user from forgetting cover 124' sitting somewhere or from purposely removing cover 124' so that the user does not have to keep track of cover 124'. Providing an easy way to store cover 124' in recess 132' will ensure proper use of cover 124' and protect display 116' from damage.

Figure 4A:
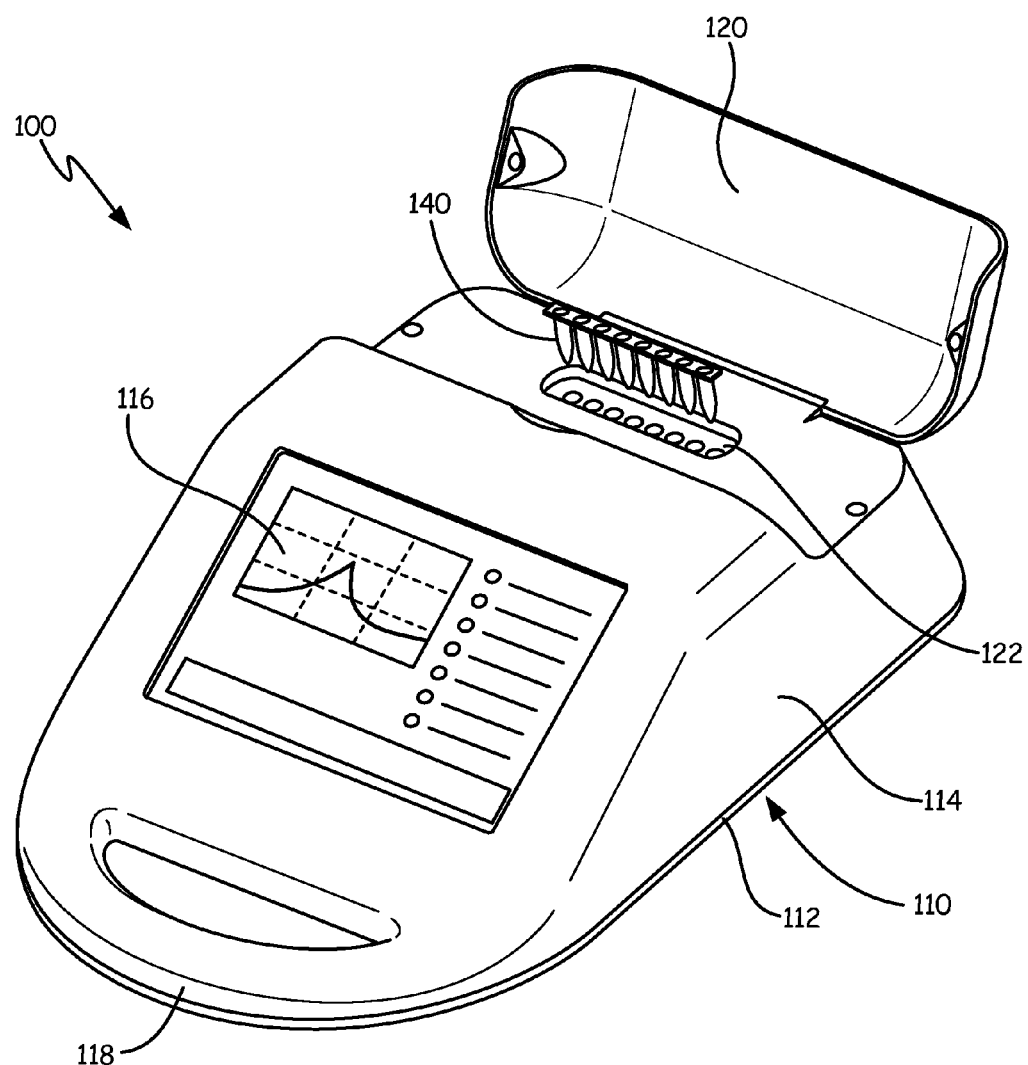
FIG. 4A is a perspective view of the portable testing device when a sample holder in the form of a tube array is being placed in the portable testing device.
Figure 4B:
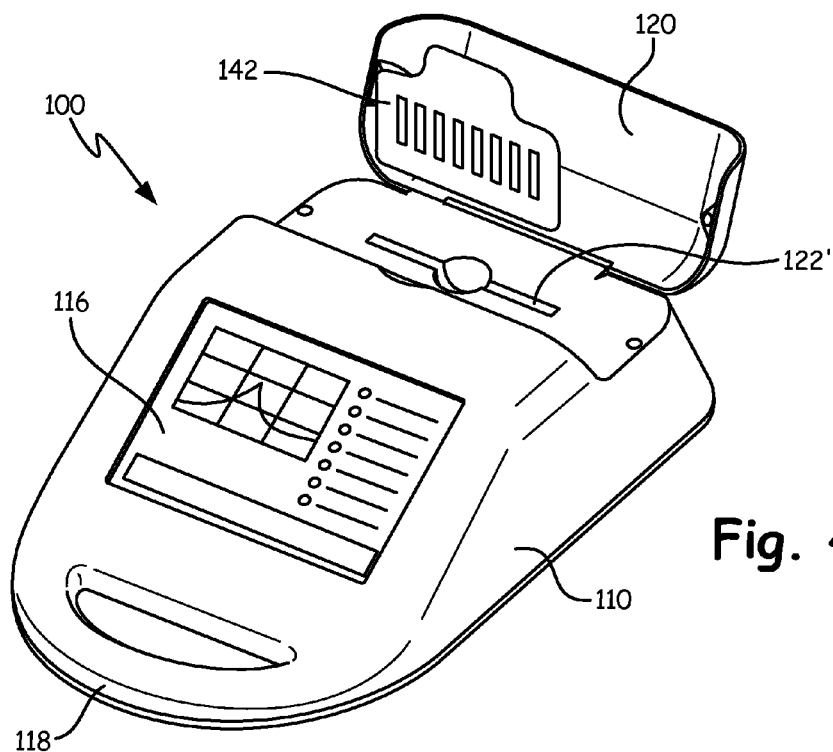
FIG. 4B is a perspective view of the portable testing device when a sample holder in the form of a card is being placed in the portable testing device.
Figure 4C:
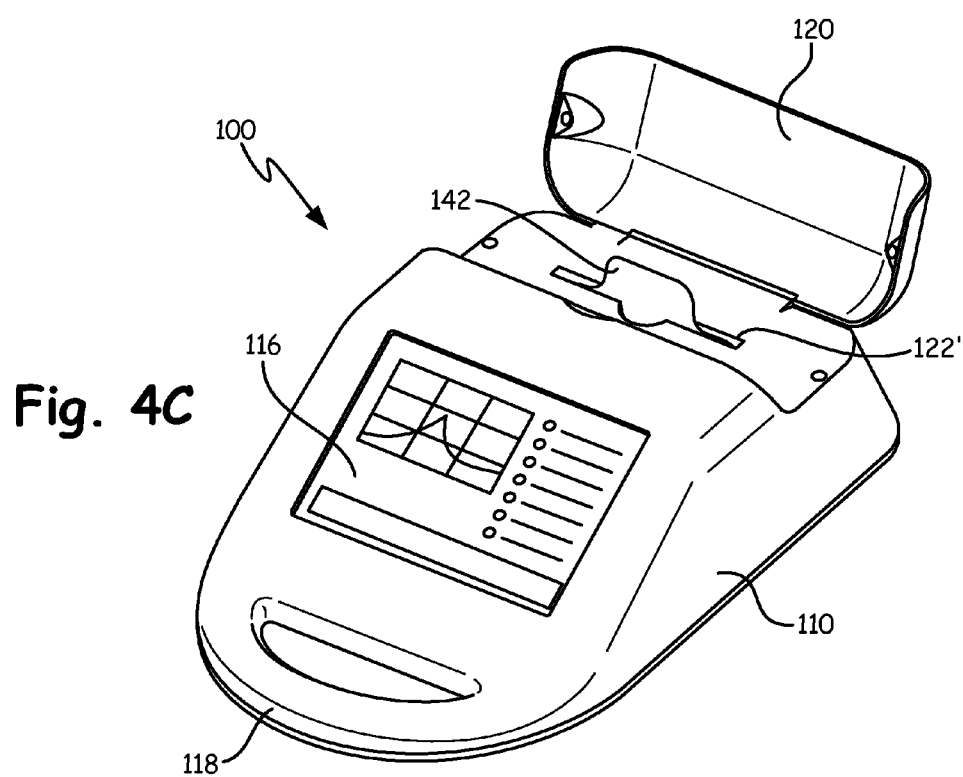
FIG. 4C is a perspective view of the portable testing device when the card is placed in the portable testing device.

FIG. 4A is a perspective view of portable testing device 100 when a sample holder in the form of tube array 140 is being placed in portable testing device 100. FIG. 4B is a perspective view of portable testing device 100 when a sample holder in the form of card 142 is being placed in portable testing device 100. FIG. 4C is a perspective view of portable testing device 100 when card 142 is placed in portable testing device 100. Portable testing device 100 includes housing 110, display 116, handle 118, and lid 120. FIG. 4A also includes receptacle 122 and tube array 140. FIGS. 4B-4C also include receptacle 122' and card 142.

As seen in FIG. 4A, receptacle 122 is located on a top side of portable testing device 100 in the embodiment shown, but can be located in any suitable location in alternate embodiments. Receptacle 122 is an opening in housing 110 of portable testing device 100. A sample holder containing a biological sample can be placed in receptacle 122 for testing. In FIG. 4A, receptacle 122 is configured to receive tube array 140. In alternate embodiments, receptacle 122 can be configured in any manner that is capable of receiving a sample holder.

As seen in FIGS. 4B-4C, receptacle 122' is located on a top side of portable testing device 100 in the embodiment shown, but can be located in any suitable location in alternate embodiments. Receptacle 122' is an opening in housing 110 of portable testing device 100. A sample holder containing a biological sample can be placed in receptacle 122' for testing. In FIGS. 4B-4C, receptacle 122' is configured to receive card 142. In alternate embodiments, receptacle 122' can be configured in any manner that is capable of receiving a sample holder.

When a sample holder is placed in receptacle 122 (or receptacle 122') of portable testing device 100 it will be positioned in an optical assembly that is held in portable testing device 100. The optical assembly will be able to amplify, excite, and detect the biological sample in the sample holder. The optical assembly includes a heating component that is used to heat the biological sample, causing it to amplify. The optical assembly will then use radiation to excite the biological sample, so that the biological sample with emit radiation. Lid 120 is positioned over receptacle 122 to prevent radiation from escaping housing 110 through receptacle 122. Lid 120 further prevents ambient light from entering housing 110 through receptacle 122, which prevents the ambient light from skewing or negating results of the tests that are being run in portable testing device 100. Lid 120 is capable of being moved between an open and closed position. When lid 120 is in an open position, sample holders (including tube array 140 or card 142) can be inserted into and removed from receptacle 122. When lid 120 is closed, sample holders will be held in receptacle 122 and radiation in portable testing device 100 will not escape from housing 110.

Receptacle 122 can be shaped to receive any sample holder, allowing portable testing device 100 to be designed to accommodate a wide variety of standard and custom designed sample holders. Tube array 140 and card 142 are examples of each. Tube array 140 is a standard sample holder that is widely available on the market. Card 142 is a custom designed sample holder that is designed to be used with portable testing device 100. Receptacle 122 allows portable testing device 100 to be designed to accommodate a wide variety of sample holder shapes and sizes.

Figure 5:
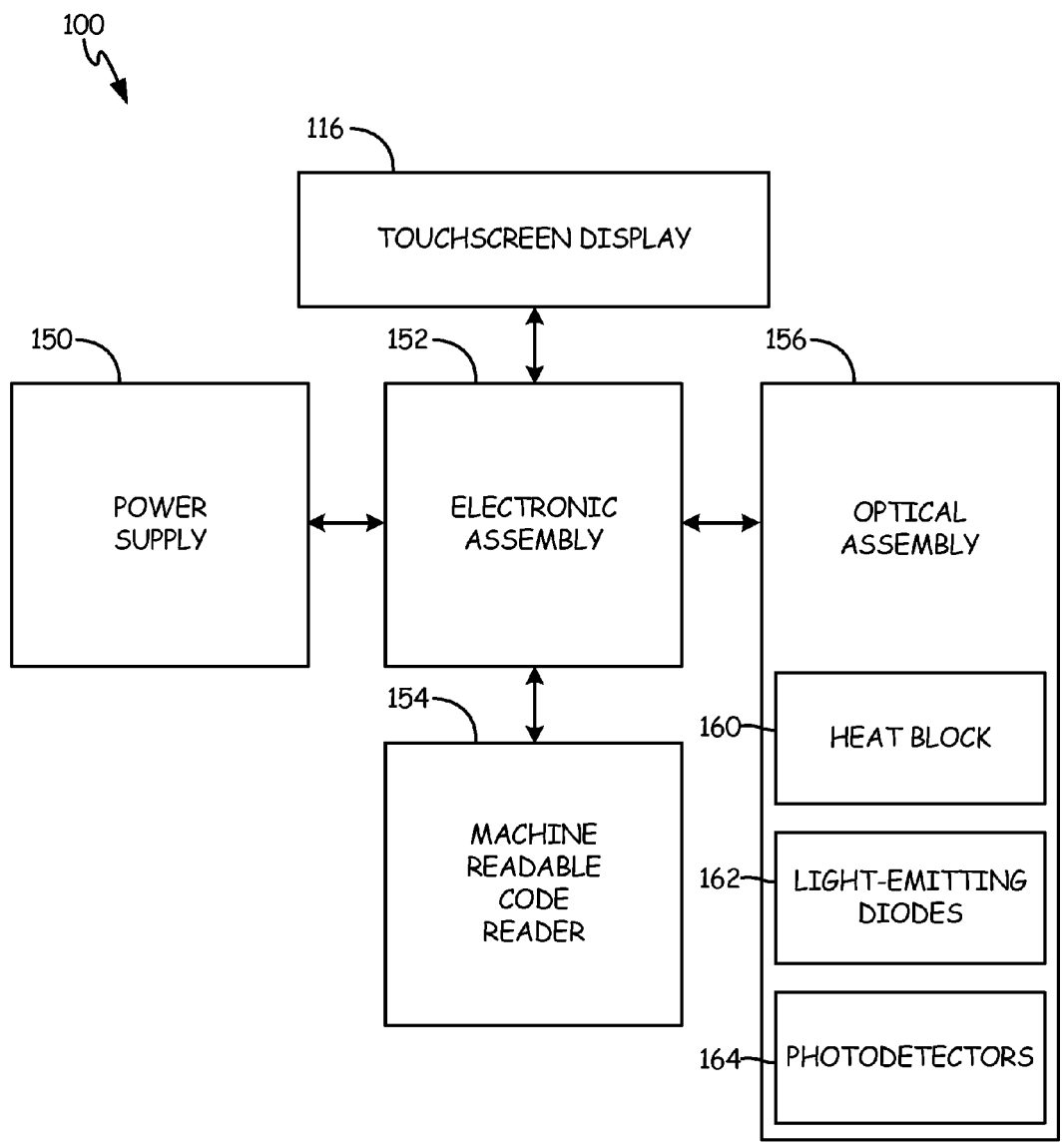
FIG. 5 is a block diagram of the portable testing device.

FIG. 5 is a block diagram of portable testing device 100. Portable testing device 100 includes display 116, power supply 150, electronic assembly 152, machine readable code reader 154, and optical assembly 156. Optical assembly 156 includes heat block 160, light-emitting diodes 162, and photodetectors 164.

Portable testing device 100 is used to analyze and obtain data from biological samples in the field. To accomplish this, portable testing device 100 is equipped with display 116, power supply 150, electronic assembly 152, machine readable code reader 154, and optical assembly 156. In the embodiment shown, display 116 is a touchscreen display that acts as a primary user interface between a user and portable testing device 100. A user can input information into display 116 to indicate what testing should be run in portable testing device 100 for each biological sample. Further, a user can monitor the results of tests that are run in portable testing device 100 on display 116.

Display 116 is connected to electronic assembly 152 with interface circuitry. Information that is inputted into display 116 will be communicated to electronic assembly 152 using the interface circuitry. Electronic assembly 152 includes hardware, firmware, and software to control the operations of portable testing device 100, including a microprocessor. Electronic assembly 152 will indicate what testing is to be run in portable testing device 100 and communicates this information throughout the device. Data that is collected in portable testing device 100 during testing will also be communicated to electronic assembly 152. Electronic assembly 152 can process this data and transmit it to display 116 to be displayed. Electronic assembly 152 further stores this data for retrieval or transfer at a later time.

Electronic assembly 152 is connected to power supply 150 with interface circuitry. Power supply 150 includes components that are capable of powering portable testing device 100, including a battery, a power board, a power switch, and a power jack that can be connected to a power source for recharging. Power from power supply 150 is sent to electronic assembly 152 through the interface circuitry so that portable testing device 100 can operate.

Portable testing device 100 can further include machine readable code reader 154. When a sample holder containing a machine readable code is placed in portable testing device 100, machine readable code reader 154 can read the machine readable code on the sample holder. A machine readable code can also be provided separate from the sample holder. The machine readable code can contain all of the parameters for the testing protocol and the assay traceability information for the test that is to be run. Alternatively, the machine readable code can indicate what test is to be run. This is advantageous, as it allows a user to insert a sample into portable testing device 100 and portable testing device 100 will automatically select a test protocol and begin testing.

Electronic assembly 152 includes a microprocessor, associated memory, and interface circuitry for interfacing with display 116 and optical assembly 156. Input that is received in electronic assembly 152 from display 116 can be processed in electronic assembly 152. This information can be used to control optical assembly 156. Optical assembly 156 conducts testing of the biological sample that is placed in portable testing device 100. As the testing is being completed, data that is collected in optical assembly 156 can be communicated to electronic assembly 152. Electronic assembly 152 processes this data and can transmit the data to display 116 so that the user can monitor the test results. Electronic assembly 152 can also transmit the data to an external device with any suitable data transfer means, including wireless transfer or transfer through a USB port, microUSB port, SD card, or microSD card.

Optical assembly 156 includes heat block 160, light-emitting diodes 162, and photodetectors 164 to conduct testing of the biological samples that are placed in portable testing device 100. Optical assembly 156 will amplify the biological sample using heat and will then excite the biological sample with radiation to detect the presence of a specific fluorescent marker. Biological samples that are placed in portable testing device 100 will be mixed with a reaction mixture that contains one or more fluorescent dyes. When the biological sample is placed in portable testing device 100, heat block 160 will amplify the biological sample with heat. Heat block 160 is positioned underneath receptacle 122 in portable testing device 100 so that when a sample holder containing a biological sample is placed in portable testing device 100, the sample holder will be positioned in heat block 160. As the biological sample is amplified it can be analyzed using light-emitting diodes 162 and photodetectors 164. Light-emitting diodes 162 transmit radiation to the biological sample to excite the biological sample. A plurality of light-emitting diodes 162 can be used in portable testing device 100 to excite the biological sample at a predetermined cycle rate. In the embodiment shown, the plurality of light-emitting diodes 162 cycle on and off at 1.54 kHz. In alternate embodiments, light-emitting diodes 162 can cycle at any predetermined cycle rate. When the biological sample is excited at the predetermined cycle rate, it will emit radiation at the same predetermined cycle rate and the corresponding wavelengths of the fluorescent dyes that were added to the biological sample. This radiation can be received by photodetectors 164. A plurality of photodetectors 164 can be used in portable testing device 100 to read the emitted radiation from the biological sample at different radiation wavelengths. The signals produced by photodetectors 164 can then be transmitted to electronic assembly 152 for processing and analysis, and displayed on display 116 as data collected during testing.

Portable testing device 100 is advantageous, as it is an all-in-one device. Portable testing device 100 includes optical assembly 156 to conduct testing of biological samples in the field. Portable testing device 100 further includes electronic assembly 152 and display 116 to specify what testing to run and to process and display data that is collected during testing. Portable testing device 100 further includes power supply 150, including a battery, so that portable testing device 100 can be used in the field. Portable testing device 100 includes every component that is necessary to conduct testing of a biological sample, and does so in a compact device that can be easily used in the field. Using portable testing device 100 in the field prevents concerns about contamination or degradation of biological samples and allows a user to quickly react to test results in the field.

Figure 6A:
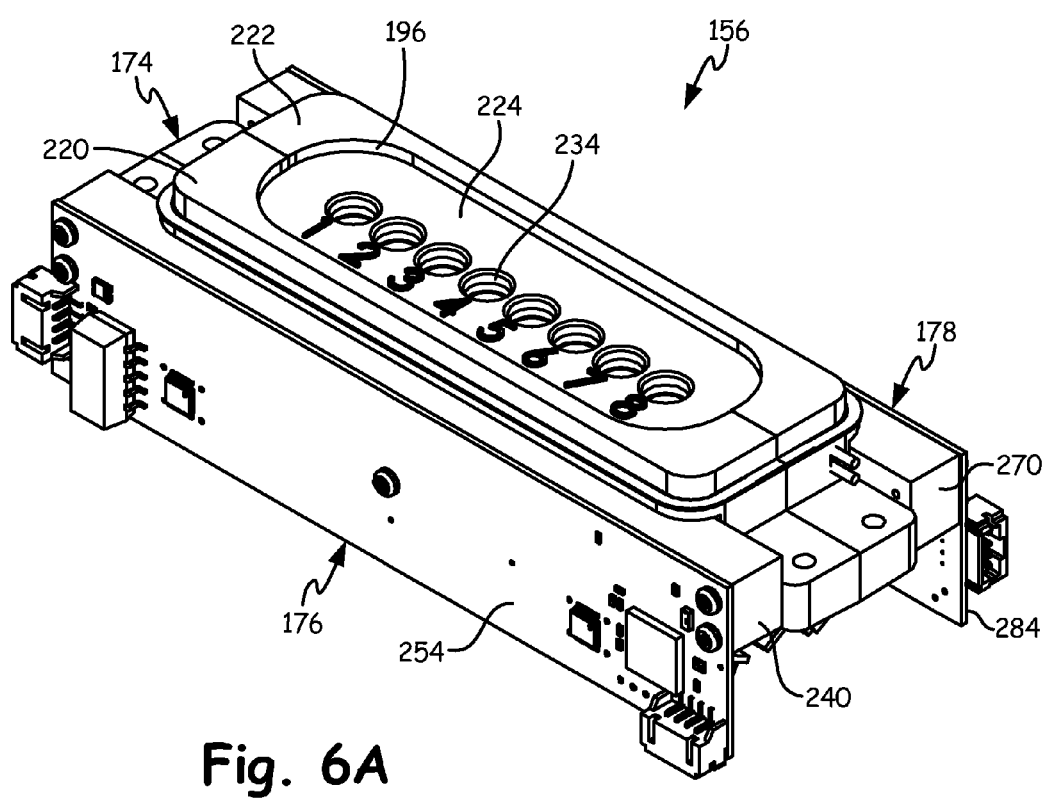
FIG. 6A is a perspective view of an optical assembly.
Figure 6B:
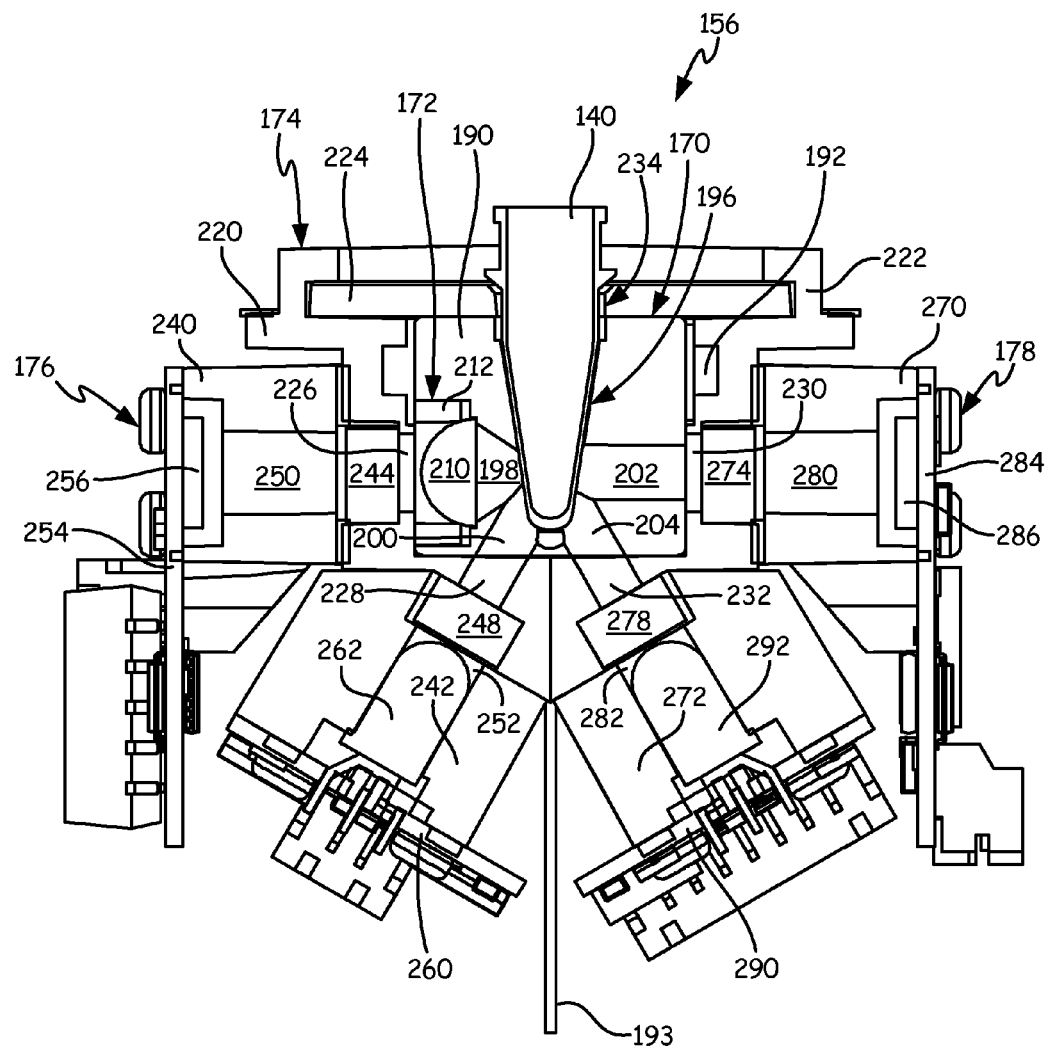
FIG. 6B is a cross-sectional view of the optical assembly.

FIG. 6A is a perspective view of optical assembly 156. FIG. 6B is a cross-sectional view of optical assembly 156. Optical assembly 156 includes heating portion 170 (not shown in FIG. 6A), lens portion 172 (not shown in FIG. 6A), housing portion 174, first optical mounting portion 176, and second optical mounting portion 178. Also shown in FIG. 6B is tube array 140.

Optical assembly 156 includes heating portion 170 to heat the biological sample and reagent mixture in tube array 140. Positioned in heating portion 170 is lens portion 172 to direct radiation through optical assembly 156. Housing portion 174 is positioned around heating portion 170 and forms the main body portion of optical assembly 156. First optical mounting portion 176 is positioned on a first side of housing portion 174 and second optical mounting portion 178 is positioned on a second side of housing portion 174. Both first optical mounting portion 176 and second optical mounting portion 178 mount light-emitting diodes to optical assembly 156 to excite the biological sample and reagent mixture in tube array 140. Further, both first optical mounting portion 176 and second optical mounting portion 178 mount photodetectors to optical assembly 156 to detect a signal from the biological sample and reagent mixture in tube array 140.

Figure 7:
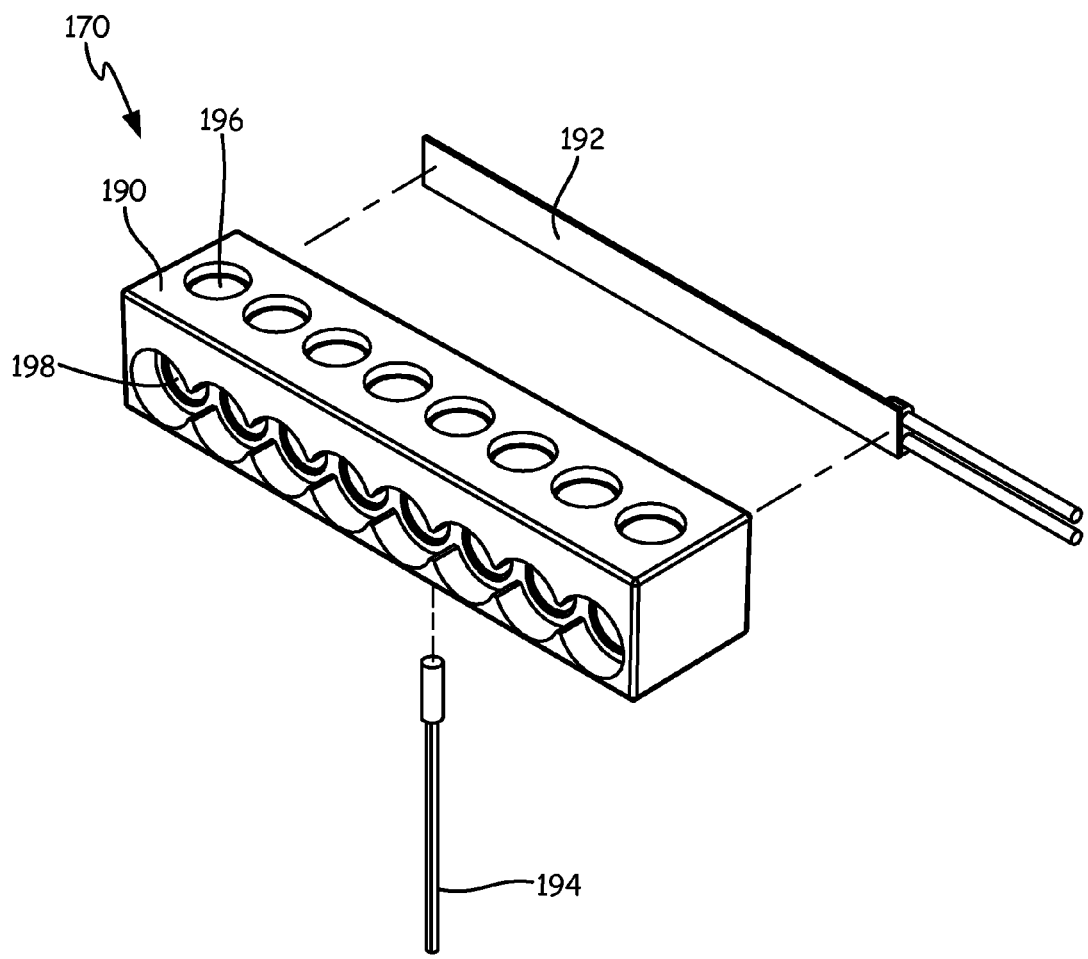
FIG. 7 is an exploded view of a heating portion of the optical assembly.

FIG. 7 is an exploded view of heating portion 170 of optical assembly 156. As seen in FIGS. 6B and 7, heating portion 170 includes sample block 190, heating component 192, temperature sensor 194, wells 196, passages 198, passages 200, passages 202, and passages 204.

Heating portion 170 includes sample block 190 that forms the main body portion of heating portion 170. Heating component 192 is attached to a second side of sample block 190. Heating component 192 is a flat polyimide heater in the embodiment shown, but can be any suitable heater in alternate embodiments. Temperature sensor 194 is placed in a bottom portion of sample block 190 to sense the temperature of sample block 190. Further, in alternate embodiments, a thermal cut out switch, such as a PEPI switch, can be placed in series with a lead on heating component 192.

Sample block 190 includes wells 196 on a top side of sample block 190. Each well 196 is sized to receive one tube in tube array 140. In the embodiment shown in FIG. 7, heating component 192 heats each of wells 196 at a constant temperature so that portable testing device 100 can be used with isothermal amplification chemistries. In alternate embodiments, heating component 192 can heat each well 196 at a different temperature across a gradient, or there can be a plurality of heating components so that each well is heated by a different heating component to a different temperature. This allows a user to conduct a preliminary test to determine what temperature should be used to analyze a particular biological sample. In further alternate embodiments, heating component 192 can include a thermal cycler that is capable of cycling heating potion 170 through different temperatures so that portable testing device 100 can be used with non-isothermal polymerase chain reaction (PCR) chemistries.

Sample block 190 further includes passages 198, passages 200, passages 202, and passages 204. Passages 198 extend from a first side of sample block 190 to wells 196. Passages 200 extending from a bottom side of sample block 190 to wells 196. Passages 202 extend from the second side of sample block 190 to wells 196. Passages 204 extend from a bottom side of sample block 190 to wells 196. Passages 198, passages 200, passages 202, and passages 204 extend through sample block 190 to direct radiation into and out of the biological sample and reagent mixture in tube array 140 in wells 196.

Figure 8:
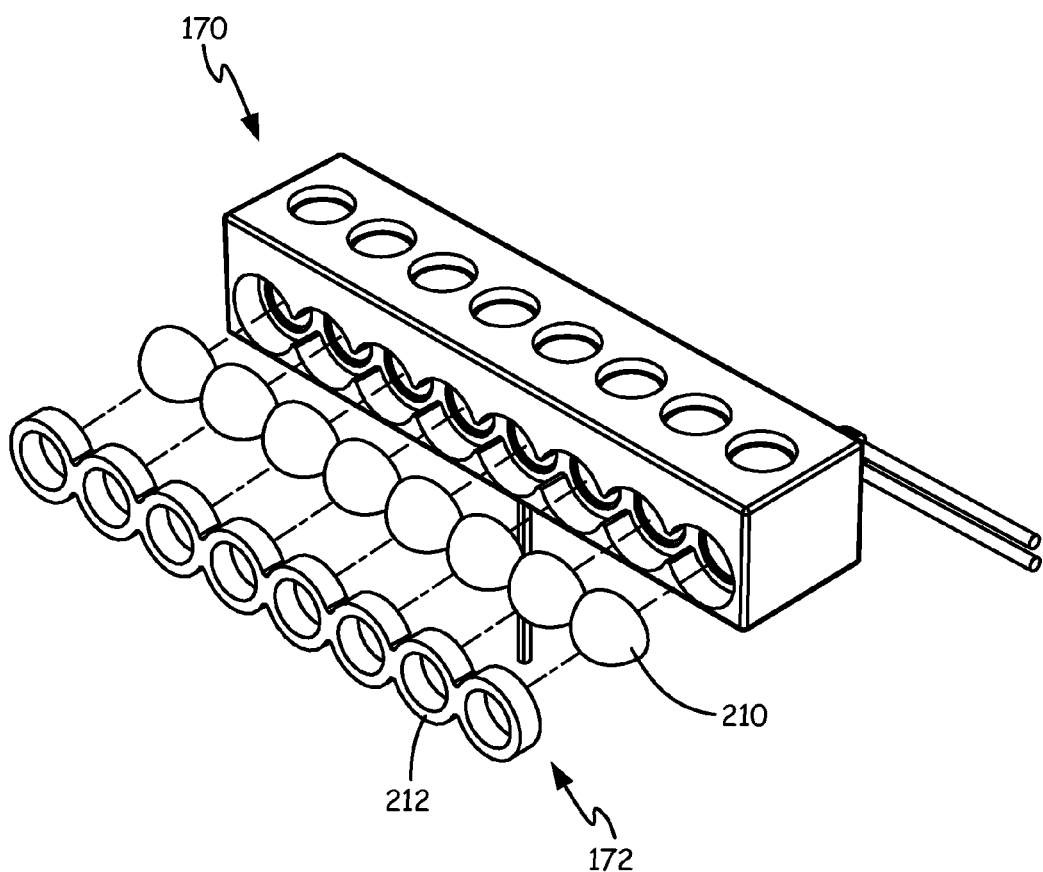
FIG. 8 is an exploded view of a lens portion of the optical assembly.

FIG. 8 is an exploded view of lens portion 172 of optical assembly 156. As seen in FIGS. 6B and 8, lens portion 172 includes lenses 210 and lens retainer 212.

Lens portion 172 includes lenses 210 that are positioned in sample block 190 of heating portion 170. Passages 198 in sample block 190 are sized to receive lenses 210 on the first side of sample block 190. One lens 210 is positioned in each passage 198 of sample block 190. Lenses 210 are held in passages 198 with lens retainer 212. Lens retainer 212 has a plurality of apertures so that radiation can pass through lens retainer 212 to pass through lenses 210.

Figure 9:
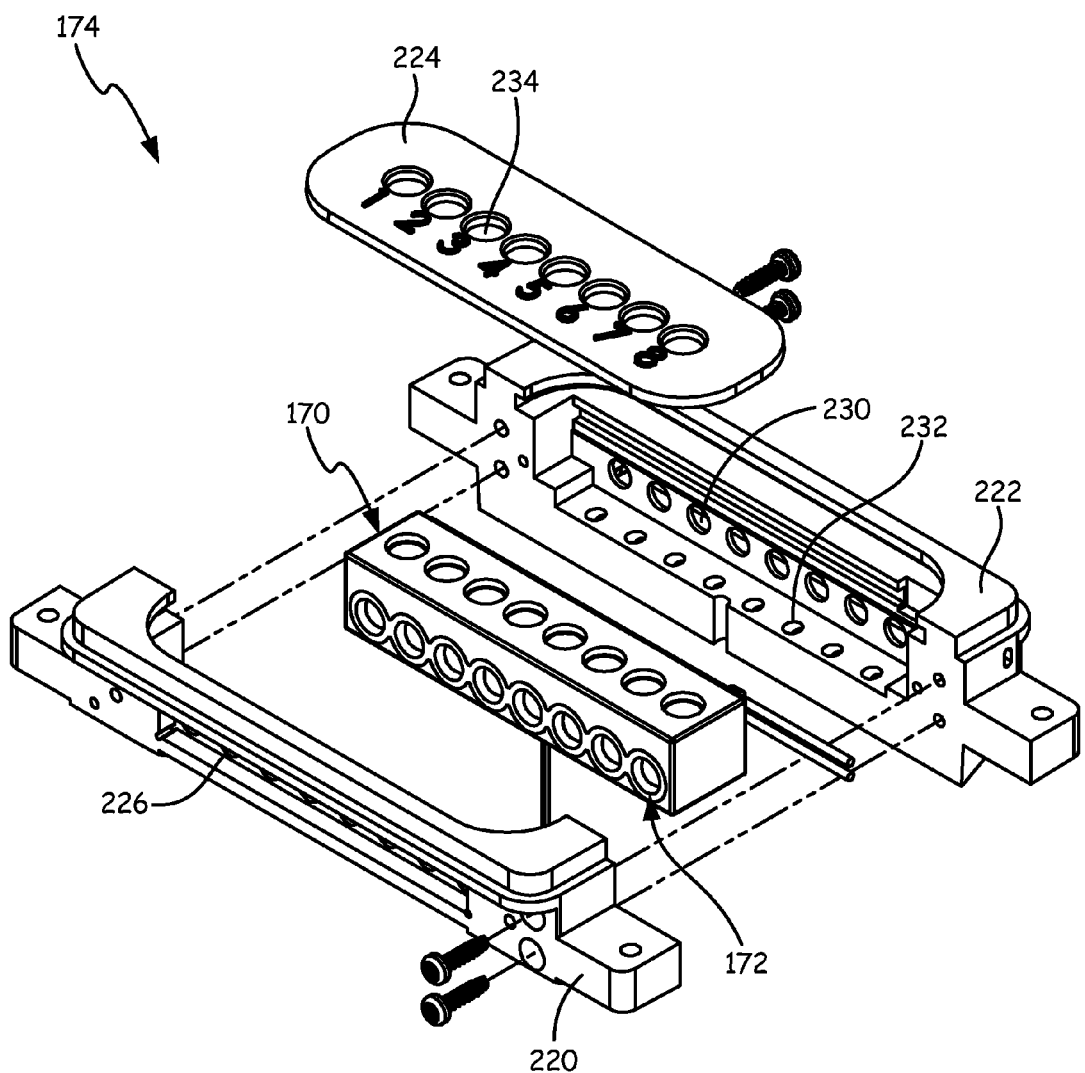
FIG. 9 is an exploded view of a housing portion of the optical assembly.

FIG. 9 is an exploded view of housing portion 174 of optical assembly 156. As seen in FIGS. 6A-6B and 9, housing portion 174 includes first housing 220, second housing 222, heat shield 224, passages 226, passages 228, passages 230, passages 232, and apertures 234.

Housing portion 174 includes first housing 220 positioned on a first side of heating portion 170 and second housing 222 positioned on a second side of heating portion 170. First housing 220 and second housing 222 form a main body portion of housing portion 174. Heat shield 224 is positioned between first housing 220 and second housing 222 on a top side of heating portion 170.

First housing 220 includes passages 226 and passages 228. Passages 226 extend from a first side of first housing 220 to an interior side of first housing 220 adjacent sample block 190. Each passage 226 in first housing 220 is aligned with one passage 198 in sample block 190. Passages 228 extend from a bottom side of first housing 220 to an interior side of first housing 220 adjacent sample block 190. Each passage 228 in first housing 220 is aligned with one passage 200 in sample block 190. Passages 226 and 228 extend through first housing 220 to direct radiation into and out of the biological sample and reagent mixture in tube array 140 in wells 196 of sample block 190.

Second housing 222 includes passages 230 and passages 232. Passages 230 extend from a second side of second housing 222 to an interior side of second housing 222 adjacent sample block 190. Each passage 230 in second housing 222 is aligned with one passage 202 in sample block 190. Passages 232 extend from a bottom side of second housing 222 to an interior side of second housing 222 adjacent sample block 190. Each passage 232 in second housing 222 is aligned with one passage 204 in sample block 190. Passages 230 and 232 extend through second housing 222 to direct radiation into and out of the biological sample and reagent mixture in tube array 140 in wells 196 of sample block 190.

Heat shield 224 is positioned over sample block 190 and held between first housing 220 and second housing 222. Apertures 234 extend from a top side to a bottom side of heat shield 224. Each aperture 234 in heat shield 224 is aligned with one well 196 in sample block 190. This allows tube array 140 to be positioned in wells 196 in sample block 190 through apertures 234 in heat shield 224. Heat shield 224 is positioned over sample block 190 to prevent heat from escaping out of the top side of sample block 190. Heat shield 224 further provides an insulated surface to protect the user from the top side of sample block 190 when sample block 190 is hot.

Figure 10A:
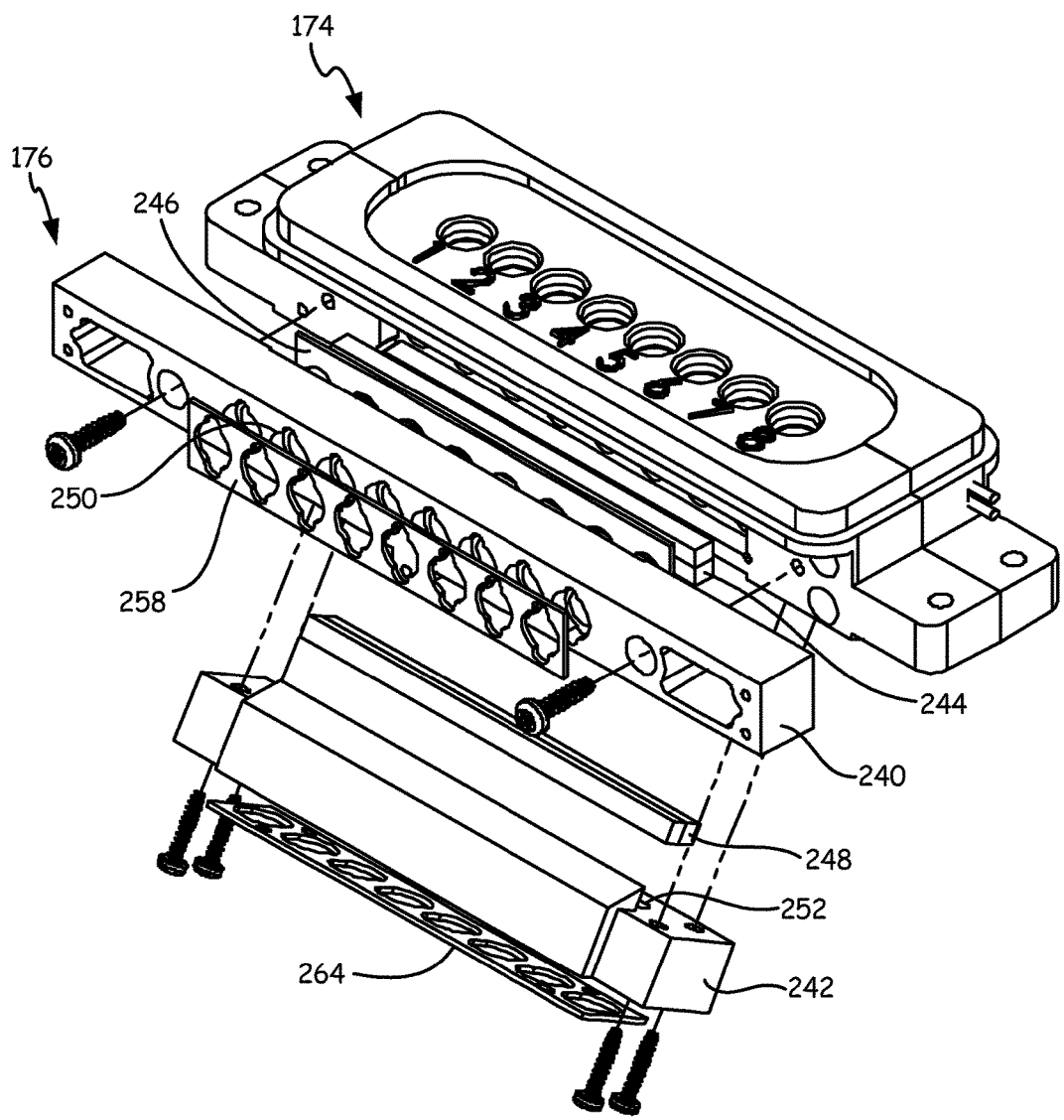
FIG. 10A is a partially exploded view of a first optical mounting portion of the optical assembly.
Figure 10B:
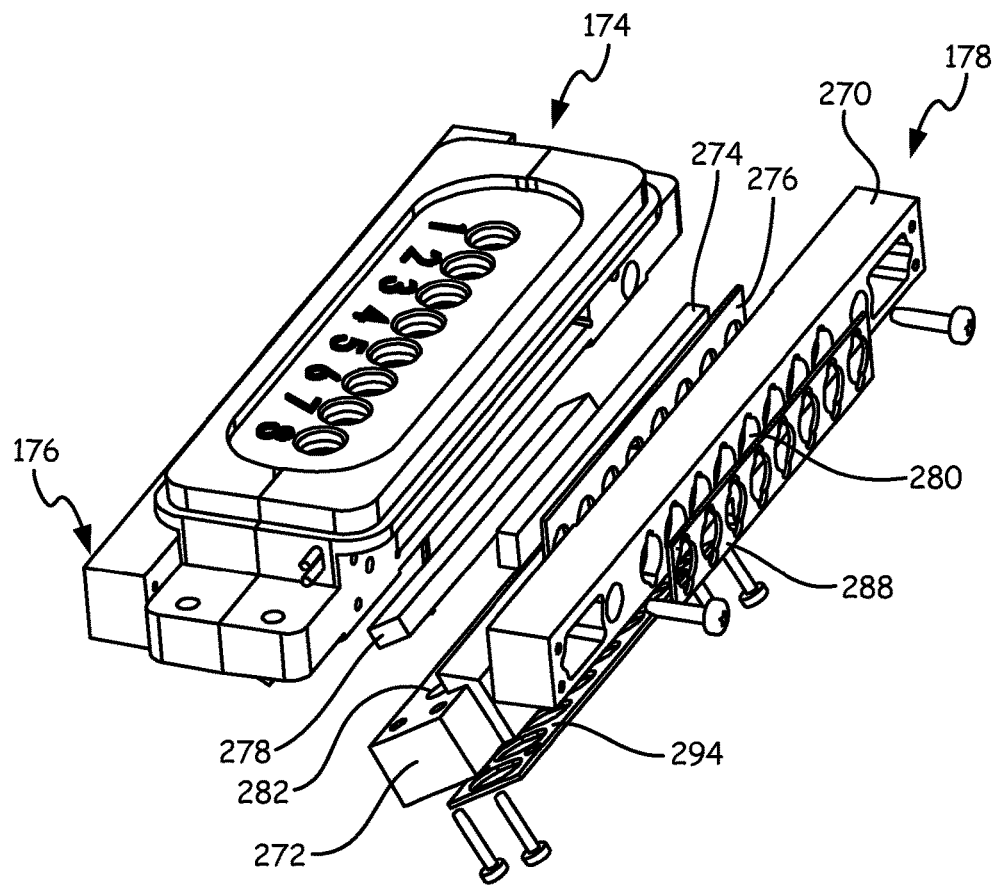
FIG. 10B is a partially exploded view of a second optical mounting portion of the optical assembly.
Figure 10C:
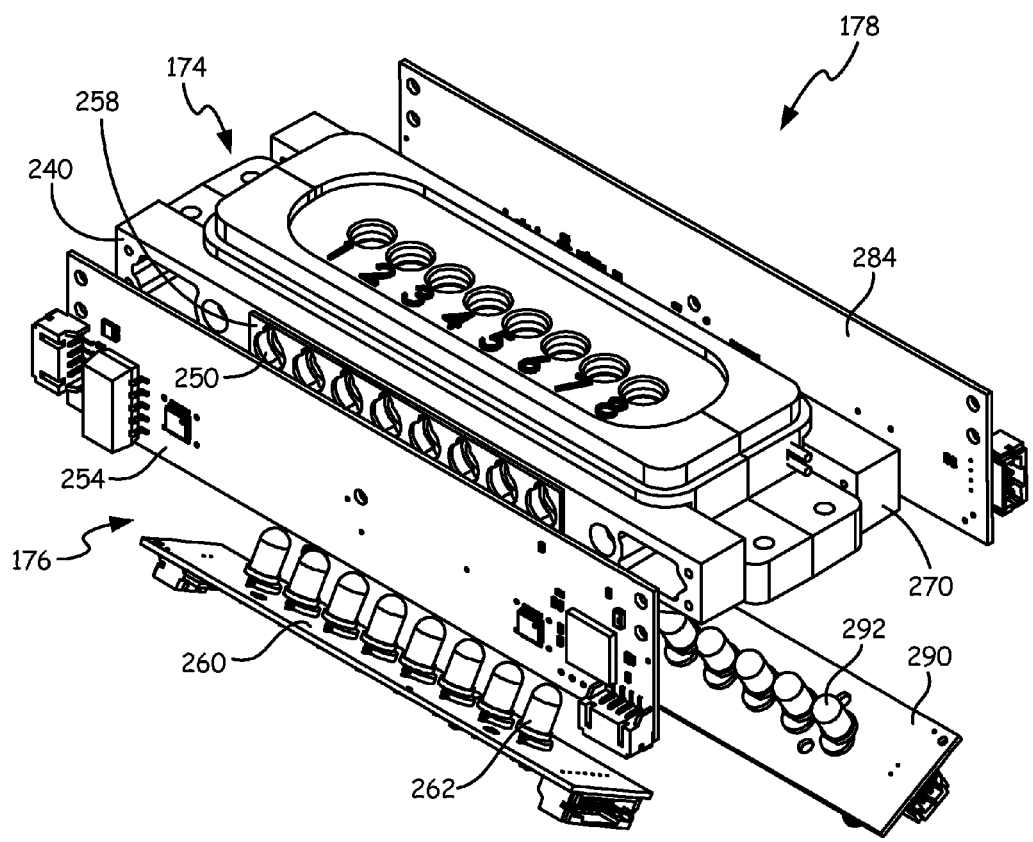
FIG. 10C is a partially exploded view of the first optical mounting portion and the second optical mounting portion of the optical assembly.

FIG. 10A is a partially exploded view of first optical mounting portion 176 of optical assembly 156. FIG. 10B is a partially exploded view of second optical mounting portion 178 of optical assembly 156. FIG. 10C is a partially exploded view of first optical mounting portion 176 and second optical mounting portion 178 of optical assembly 156. As seen in FIGS. 6A-6B, 10A, and 10C, first optical mounting portion 176 includes housing 240, housing 242, emission filter 244, gasket 246, excitation filter 248, passages 250, passages 252, photodetectors mounting board 254, photodetectors 256, gasket 258, light-emitting diodes mounting board 260, light-emitting diodes 262, and gasket 264. As seen in FIGS. 6A-6B and 10B-10C, second optical mounting portion 178 includes housing 270, housing 272, emission filter 274, gasket 276, excitation filter 278, passages 280, passages 282, photodetectors mounting board 284, photodetectors 286, gasket 288, light-emitting diodes mounting board 290, light-emitting diodes 292, and gasket 294.

First optical mounting portion 176 is positioned on a first side of housing portion 174. First optical mounting portion 176 includes housing 240 and housing 242 that form a main body portion of first optical mounting portion 176. Housing 240 is attached to a first side of first housing 220 of housing portion 174. Emission filter 244 is positioned between housing 240 and first housing 220 in a groove on the first side of first housing 220. Gasket 246 is positioned between emission filter 244 and housing 240. Housing 242 is attached to a bottom side of first housing 220 of housing portion 174. Excitation filter 248 is positioned between housing 242 and first housing 220 in a groove on the bottom side of first housing 220.

Housing 240 includes passages 250. Passages 250 extend from a first side of housing 240 to an interior side of housing 240 adjacent first housing 220. Each passage 250 in housing 240 is aligned with one passage 226 in first housing 220. Housing 242 includes passages 252. Passages 252 extend from a bottom side of housing 252 to an interior side of housing 242 adjacent first housing 220. Each passage 252 in housing 242 is aligned with one passage 228 in first housing 220.

Photodetectors mounting board 254 is connected to a first side of housing 240. Photodetectors mounting board 254 is an electronic board that includes photodetectors 256. Each photodetector 256 on photodetectors mounting board 254 is positioned in one passage 250 in housing 240. Gasket 258 is positioned between photodetectors mounting board 254 and housing 240. Light-emitting diodes mounting board 260 is attached to a bottom side of housing 242. Light-emitting diodes mounting board 260 is an electronic board that includes light-emitting diodes 262. Each light-emitting diode 262 on light-emitting diodes mounting board 260 is positioned in one passage 252 in housing 242. Gasket 264 is positioned between light-emitting diodes mounting board 260 and housing 242.

Second optical mounting portion 178 is positioned on a second side of housing portion 174. Second optical mounting portion 178 includes housing 270 and housing 272 that form a main body portion of second optical mounting portion 178. Housing 270 is attached to a second side of second housing 222 of housing portion 174. Emission filter 274 is positioned between housing 270 and second housing 222 in a groove on the second side of second housing 222. Gasket 276 is positioned between emission filter 274 and housing 270. Housing 272 is attached to a bottom side of second housing 222 of housing portion 174. Excitation filter 278 is positioned between housing 272 and second housing 222 in a groove on the bottom side of second housing 222.

Housing 270 includes passages 280. Passages 280 extend from a second side of housing 270 to an interior side of housing 270 adjacent second housing 222. Each passage 280 in housing 270 is aligned with one passage 230 in second housing 222. Housing 272 includes passages 282. Passages 282 extend from a bottom side of housing 282 to an interior side of housing 282 adjacent second housing 222. Each passage 282 in housing 272 is aligned with one passage 232 in second housing 222.

Photodetectors mounting board 284 is connected to a first side of housing 270. Photodetectors mounting board 284 is an electronic board that includes photodetectors 286. Each photodetector 286 on photodetectors mounting board 284 is positioned in one passage 280 in housing 270. Gasket 288 is positioned between photodetectors mounting board 284 and housing 270. Light-emitting diodes mounting board 290 is attached to a bottom side of housing 272. Light-emitting diodes mounting board 290 is an electronic board that includes light-emitting diodes 292. Each light-emitting diode 292 on light-emitting diodes mounting board 290 is positioned in one passage 282 in housing 272. Gasket 294 is positioned between light-emitting diodes mounting board 290 and housing 272.

As seen in FIGS. 6A-10C, optical assembly 156 can excite and detect emissions from a biological sample and reagent mixture in tube array 140 that is positioned in optical assembly 156. Light-emitting diodes 262 are bi-color light-emitting diodes that can emit radiation at two different wavelengths. In the embodiment shown, light-emitting diodes 262 are blue and amber bi-color light-emitting diodes to excite Fluorescein amidite (FAM) fluorescence dye and 6-Carboxyl-X-Rhodamine (ROX) fluorescence dye, respectively. Further, light-emitting diodes 262 emit radiation at a predetermine cycle rate of 1.54 kHz. Radiation from light-emitting diodes 262 can pass through passages 252, excitation filter 248, passages 228, and passages 200 into the biological sample and reagent mixture in tube array 140 that is held in wells 196. Excitation filter 248 is a dual bandpass excitation filter that is capable of passing either of the wavelengths emitted by light-emitting diodes 262. Excitation filter 248 is a single filter that extends across the entire length of tube array 140, thus excitation filter 248 extends between adjacent passages 228 in first housing 220. Radiation from light-emitting didoes 262 can excite a fluorescent dye in the biological sample and reagent mixture. This excitation of the fluorescent dye will emit a signal from the biological sample and reagent mixture and the emission can pass through passages 198, passages 226, emission filter 244, and passages 250 to be detected by photodetectors 256. Emission filter 244 is a dual bandpass emission filter in the embodiment shown. Emission filter 244 is a single filter that extends across the entire length of tube array 140, thus emission filter 244 extends between adjacent passages 226 in first housing 220.

Light-emitting diodes 292 are light-emitting diodes that can emit radiation at a single wavelength. In the embodiment shown, light-emitting diodes 292 are green light-emitting diodes to excite 6-carboxy-X-hexachlorofluorescein (HEX) fluorescence dye. Further, light-emitting diodes 292 emit radiation at a predetermine cycle rate of 1.54 kHz. Radiation from light-emitting diodes 292 can pass through passages 282, excitation filter 278, passages 232, and passages 204 into the biological sample and reagent mixture in tube array 140 that is held in wells 196. Excitation filter 278 is a single bandpass filter that is capable of passing the wavelength emitted by light-emitting diodes 292. Excitation filter 278 is a single filter that extends across the entire length of tube array 140, thus excitation filter 278 extends between adjacent passages 232 in second housing 222. Radiation from light-emitting didoes 292 can excite a fluorescent dye in the biological sample and reagent mixture. This excitation of the fluorescent dye will emit a signal from the biological sample and reagent mixture and the emission can pass through passages 202, passages 230, emission filter 274, and passages 280 to be detected by photodetectors 286. Emission filter 274 is a single bandpass filter in the embodiment shown. Emission filter 274 is a single filter that extends across the entire length of tube array 140, thus emission filter 274 extends between adjacent passages 230 in second housing 222.

In an alternate embodiment, light-emitting diodes 292 can be bi-color light-emitting diodes that can emit radiation at two different wavelengths. Further, excitation filter 278 can be a dual bandpass filter that is capable of passing both of the wavelengths emitted by light-emitting diodes 292, and emission filter 274 can also be a dual bandpass filter. This would result in portable testing device 100 being capable of testing four different fluorescent dyes that can be mixed in with the biological sample and reagent mixture.

Light-emitting diodes 262 and light-emitting diodes 292 emit radiation in the form of light that is cycled at a predetermined rate of 1.54 kHz. This causes emissions from the biological sample and reagent mixture at the same predetermined rate. Photodetectors 256 and photodetectors 286 thus receive the emissions from the biological sample and reagent mixture at a rate of 1.54 kHz as well. The electronic circuitry connected to photodetectors 256 and photodetectors 286 is designed to electronically filter out all other frequencies except for 1.54 kHz. This will negate any ambient light or other radiation sources in portable testing device 100 that may interfere with the accuracy of the testing.

Having a single filter for emission filter 244, excitation filter 248, emission filter 274, and excitation filter 278 simplifies the design of portable testing device 100. This simplified design makes portable testing device 100 more suitable for use in the field. If one of emission filter 244, excitation filter 248, emission filter 274, or excitation filter 278 had to be replaced, it would be easy to replace the entire filter instead of a number of different individual filters. Further, using one filter for each of emission filter 244, excitation filter 248, emission filter 274, or excitation filter 278 reduces the cost of portable testing device 100.

Figure 11A:
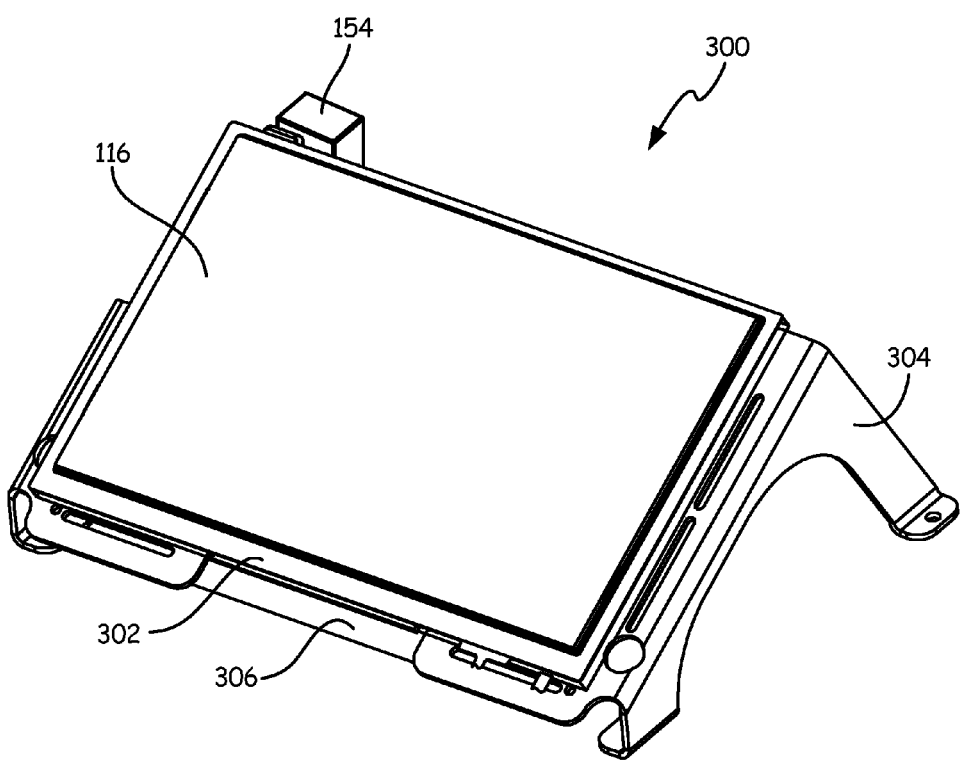
FIG. 11A is a perspective view of a screen assembly.
Figure 11B:
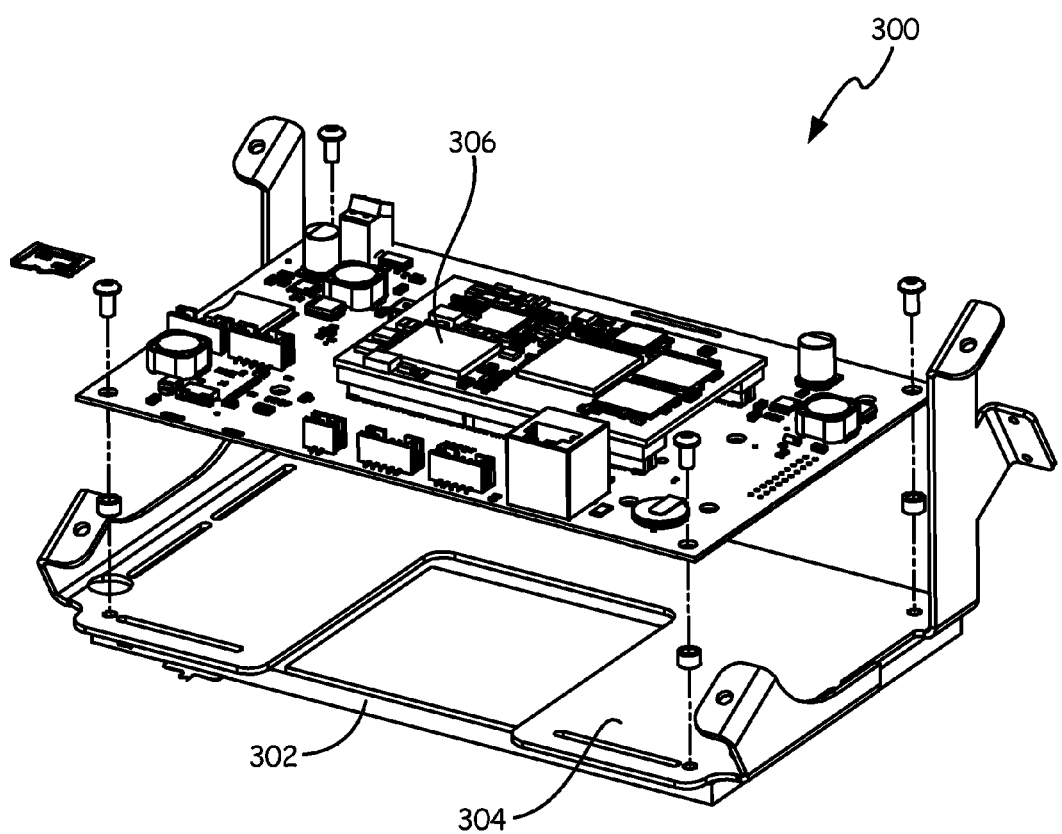
FIG. 11B is a partially exploded view of the screen assembly.
Figure 11C:
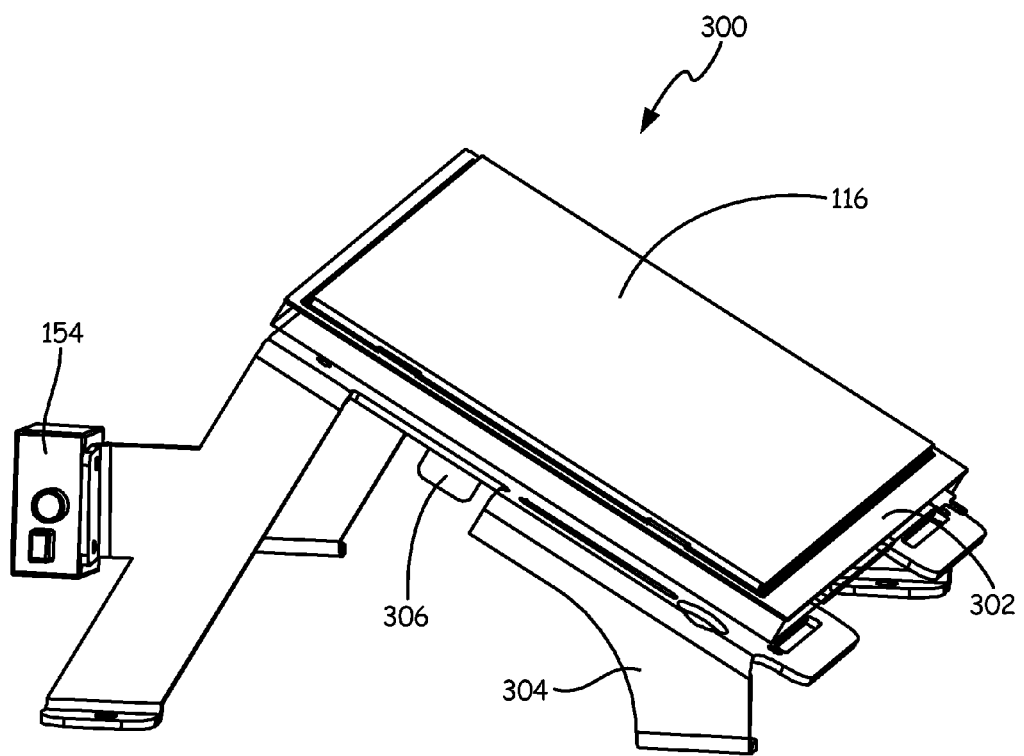
FIG. 11C is a partially exploded view of a machine readable code reader attached to the screen assembly.

FIG. 11A is a perspective view of screen assembly 300. FIG. 11B is a partially exploded view of screen assembly 300. FIG. 11C is a partially exploded view of machine readable code reader 154 attached to screen assembly 300. Screen assembly 300 includes screen 302, screen mount 304, and circuit board 306. Screen 302 includes display 116. FIGS. 11A and 11C further shown machine readable code reader 154.

Screen assembly 300 includes screen 302 mounted to screen mount 304. Screen 302 includes display 116 on a first side of screen 302. A second side of screen 302 is mounted to a first side of screen mount 304 with a fastener. In the embodiment shown, screen 302 is mounted to screen mount 304 with an adhesive fastener, but screen 302 can be mounted to screen mount 304 with any suitable fastener in alternate embodiments.

Circuit board 306 is attached to a second side of screen mount 304 with fasteners. In the embodiment shown, circuit board 306 is attached to screen mount 304 with screw fasteners, but circuit board 306 can be attached to screen mount 304 with any suitable fastener in alternate embodiments. Circuit board 306 is a part of electronic assembly 152 that communicates with screen 302 and that contains a system computer for portable testing device 100. Circuit board 306 can further communicate with other electronic components of electronic assembly 152 in portable testing device 100.

Machine readable code reader 154 is also attached to screen mount 304 with fasteners. In the embodiment shown, machine readable code reader 154 is attached to screen mount 304 with screw fasteners, but machine readable code reader 154 can be attached to screen mount 304 with any suitable fastener in alternate embodiments. Machine readable code reader 154 is connected to electronic assembly 152 with interface circuitry. When machine readable code reader 154 is used to scan a code, the code information can be communicated to electronic assembly 152 to indicate to portable testing device 100 what test protocol is to be run.

Figure 12:
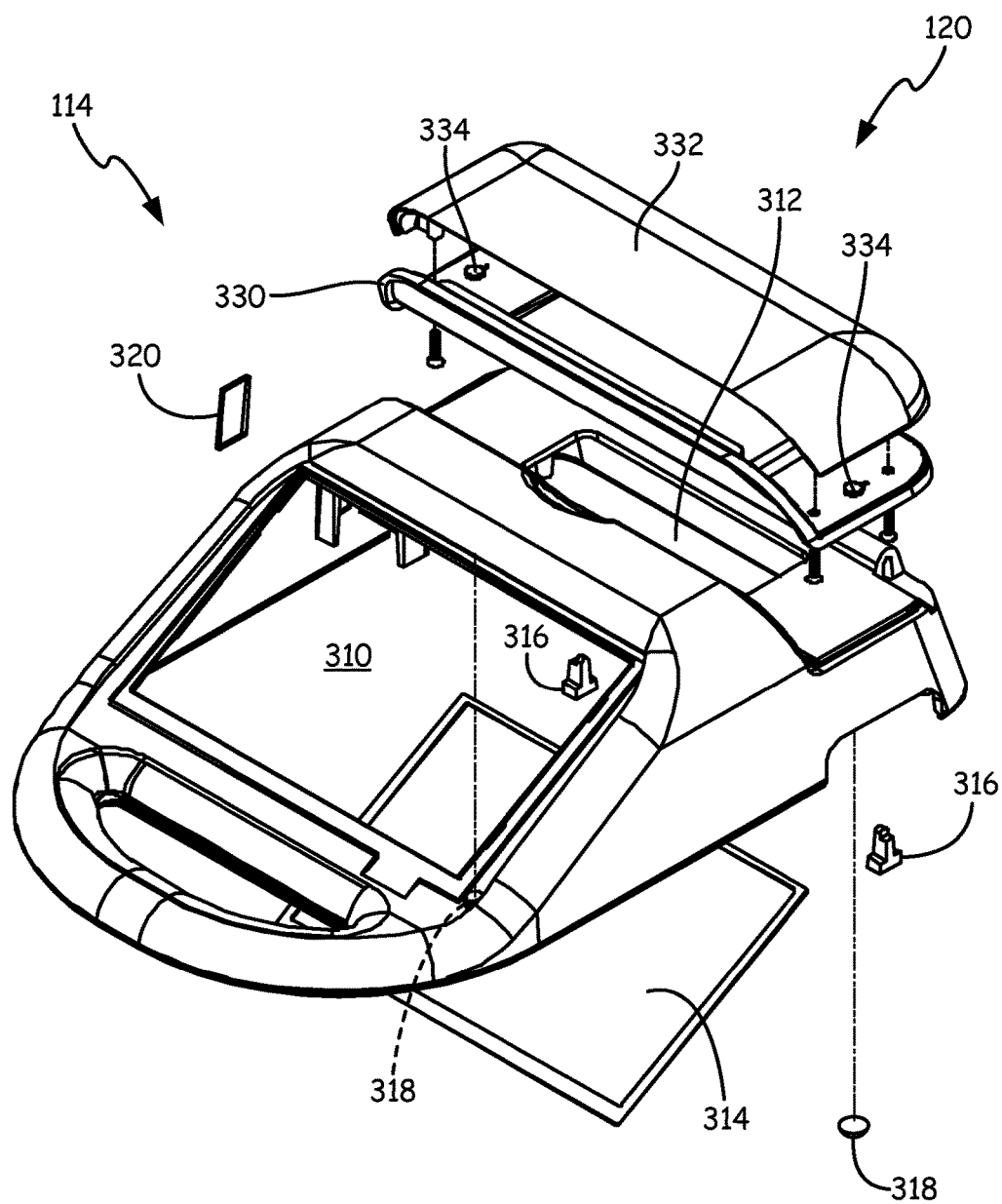
FIG. 12 is an exploded view of a second housing portion and a lid of the portable testing device.

FIG. 12 is an exploded view of second housing portion 114 and lid 120 of portable testing device 100. Second housing portion 114 includes opening 310, opening 312, gasket 314, hinge inserts 316, magnets 318, and window 320. Lid 120 includes first lid portion 330, second lid portion 332, and magnets 334.

Second housing portion 114 includes opening 310 and opening 312. Opening 310 is an opening on a top side of second housing portion 114 in which screen 302 of screen assembly 300 can be positioned. Gasket 314 is provided to form a seal between opening 310 in second housing portion 114 and screen 302. Positioning screen 302 of screen assembly 300 in opening 310 allows display 116 of screen 302 to be accessed through opening 310. Opening 312 is an opening on a top side of second housing portion 114 in which optical assembly 156 can be positioned. Positioned optical assembly 156 in opening 312 allows a user to place and remove tube array 140 from optical assembly 156 for analysis. Lid 116 is positioned over opening 312.

Hinge inserts 316 are positioned on second housing portion 114 to hinge lid 116 to second housing portion 114. Magnets 318 are positioned on second housing portion 114 to hold lid 116 in place over opening 312 when the lid is in a closed position. Both hinge inserts 316 and magnets 318 are positioned adjacent opening 312 on the top side of second housing portion 114. Window 320 is also provided on a side of second housing portion 114. Machine readable code reader 154 is positioned adjacent to window 320 in portable testing device 100 so that a code can be read by machine readable code reader 154 through window 320.

Lid 116 is attached to second housing portion 114 with hinge inserts 316. Lid 116 includes first lid portion 330 and second lid portion 332. First lid portion 330 includes hinge pins that mate with hinge inserts 316 to hold lid 116 on portable testing device 100. First lid portion 330 further includes a smooth surface on an interior surface to interface with tube array 140 when tube array 140 is placed in portable testing device 100. The smooth surface of lid portion 330 that interfaces with tube array 140 can be easily cleaned and decontaminated after a test is completed in portable testing device 100. Magnets 334 are positioned on first lid portion 330 and are aligned with magnets 318 on second housing portion 114. Magnets 334 and magnets 318 will hold lid 116 on second housing portion 114.

Second lid portion 332 is connected to a top of first lid portion 330 with a space provided in between. This space can be left open or it can be filled with an insulating material so that lid 116 can act as an insulator over receptacle 122 of portable testing device 100. This will contain the heat from heating component 192 in portable testing device 100. Further, in alternate embodiments, a heating component can be attached to lid 116 to come into contact with the top of tube array 140. This can further heat an area surrounding tube array 140 and prevent condensation on a cap portion of tube array 140.

Figure 13A:
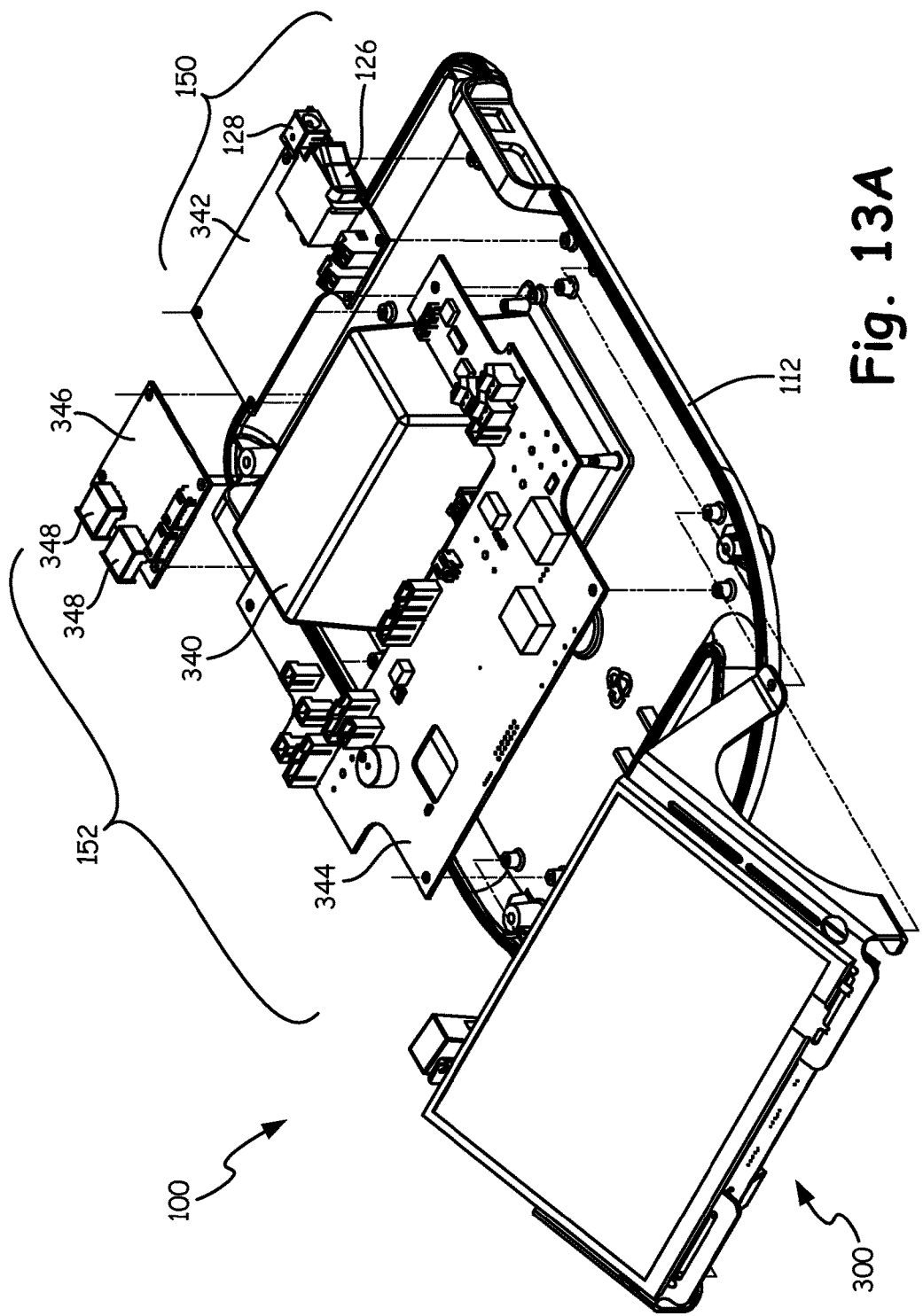
FIG. 13A is an exploded view of the screen assembly and a first housing portion of the portable testing device.
Figure 13B:
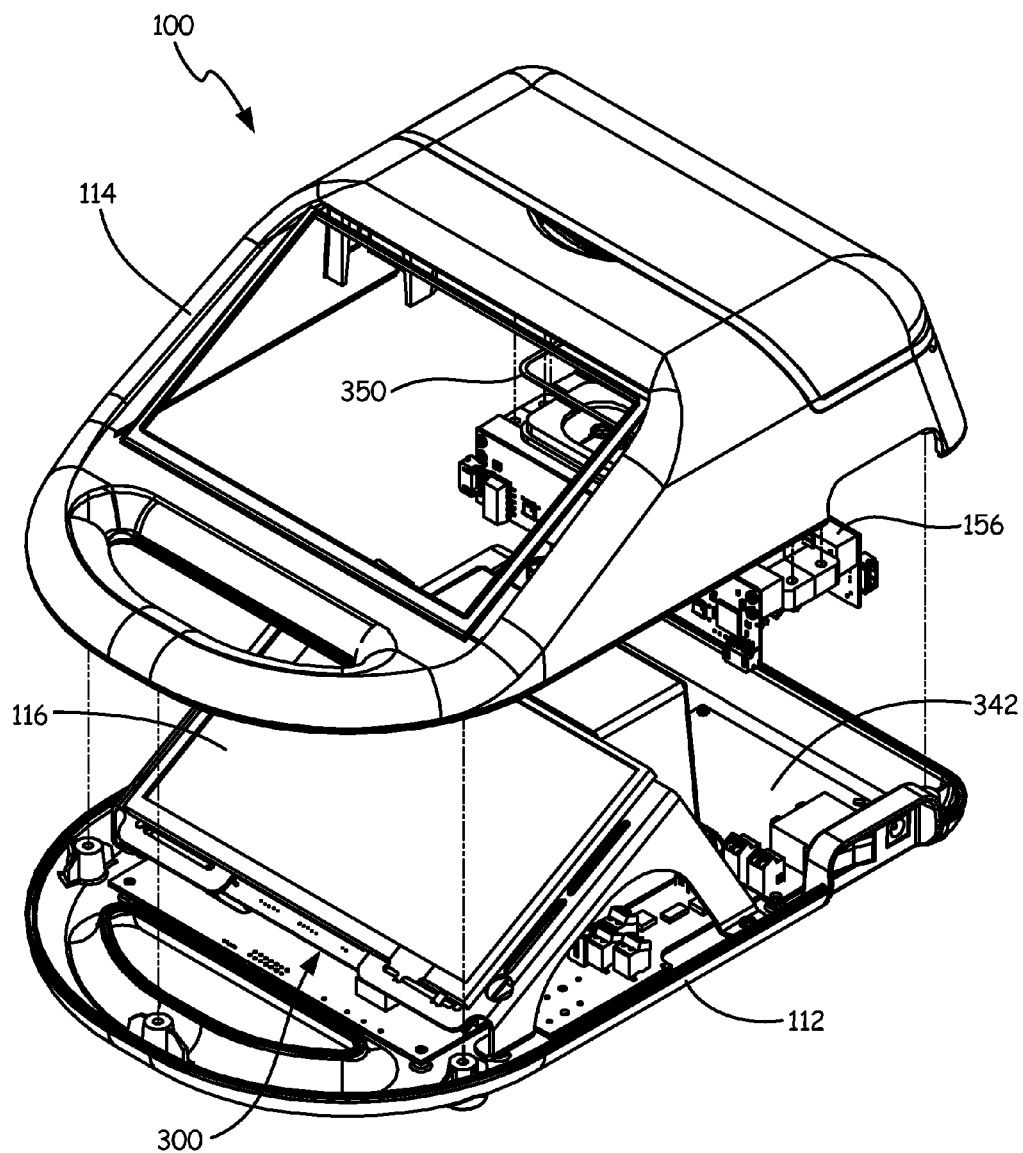
FIG. 13B is a partially exploded view of the screen assembly, the optical assembly, the first housing portion, and the second housing portion in the portable testing device.
Figure 13C:
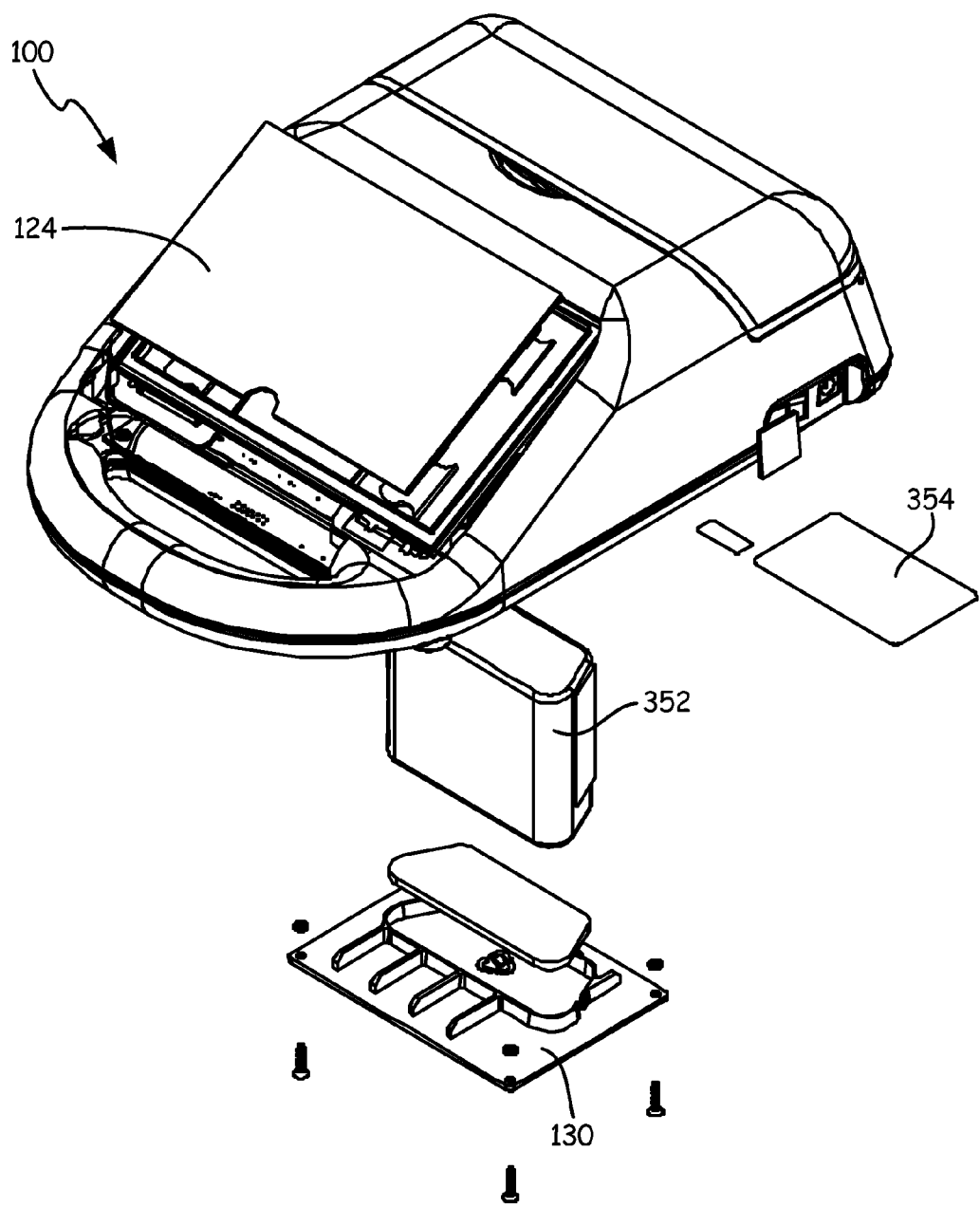
FIG. 13C is a partially exploded view of the portable testing device.

FIG. 13A is an exploded view of screen assembly 300 and first housing portion 112 of portable testing device 100. FIG. 13B is a partially exploded view of screen assembly 300, optical assembly 156, first housing portion 112, and second housing portion 114 of portable testing device 100. FIG. 13C is a partially exploded view of portable testing device 100. Portable testing device includes first housing portion 112, second housing portion 114, power supply 150, electronic assembly 152, optical assembly 156, screen assembly 300, battery housing 340, gasket 350, and serial tag 354. Power supply 150 includes power switch 126, power jack 128, power board 342, and battery 352. Electronic assembly 152 includes electronic board 344, communications board 346, and USB ports 348. Electronic board 344 is an input output controller board.

As seen in FIG. 13A, power supply 150, electronic assembly 152, and screen assembly 300 are positioned in first housing portion 112. Battery housing 340 is also positioned over battery 352 in first housing portion 112.

Power supply 150 includes power switch 126 and power jack 128 attached to power board 342. Power board 342 is positioned adjacent a back side of first housing portion 112. Power board 342 is further connected to battery 352 that is covered by battery housing 340 through interface circuitry. Power supply 150 powers portable testing device 100.

Electronic assembly 152 includes electronic board 344, communication board 346, and USB ports 348. Electronic board 344 is positioned in a center of first housing portion 112. Screen assembly 300 is positioned adjacent to a front side of first housing portion 112, positioned partially over electronic board 344. Circuit board 306 of screen assembly 300 can be connected to circuit board 300 with interface circuitry. Communication board 346 is positioned adjacent the back side of first housing portion 112. Positioned on communication board 346 are two USB ports 348. In alternate embodiments, USB ports 348 can be any ports that allow portable testing device 100 to be connected to other electronic devices, including Bluetooth or wireless communication capabilities. Communications board 346 is connected to electronic board 344 with interface circuitry. A global positioning capability is also implemented in communications board 346. This allows portable testing device 100 to log the location of portable testing device 100 when tests are run. This allows a user to track the location of pathogens that are detected when testing is completed in the field.

As seen in FIG. 13B, optical assembly 156 is positioned over power board 342 and communications board 346 adjacent to the back side of portable testing device 100. Second housing portion 114 can be placed over the components held in first housing portion 112 of portable testing device 100. Screen 302 of screen assembly 300 extends through opening 310 of second housing portion 114 so that display 116 on screen 302 can be accessed by a user. Optical assembly 156 is positioned adjacent to opening 312 of second housing portion 314 so that a sample holder can be placed in optical assembly 156 through opening 312. Gasket 350 is positioned between a perimeter of opening 312 and optical assembly 156 to form a seal between second housing portion 114 and optical assembly 156.

As seen in FIG. 13C, battery 352 is inserted into portable testing device 100 through a bottom side of first housing portion 112. When battery 352 is placed in portable testing device 100 it will be positioned in battery housing 340 (as seen in FIG. 13A). Battery lid 130 can then be placed over battery 352 and fastened to first housing portion 112 to hold battery 352 in portable testing device 100. Cover 124 can also be positioned over display 116 of portable testing device 100 to protect display 116 from damage. Serial tag 354 can be affixed to a bottom side of first housing portion 112 using any suitable fastening means.

Figure 14:
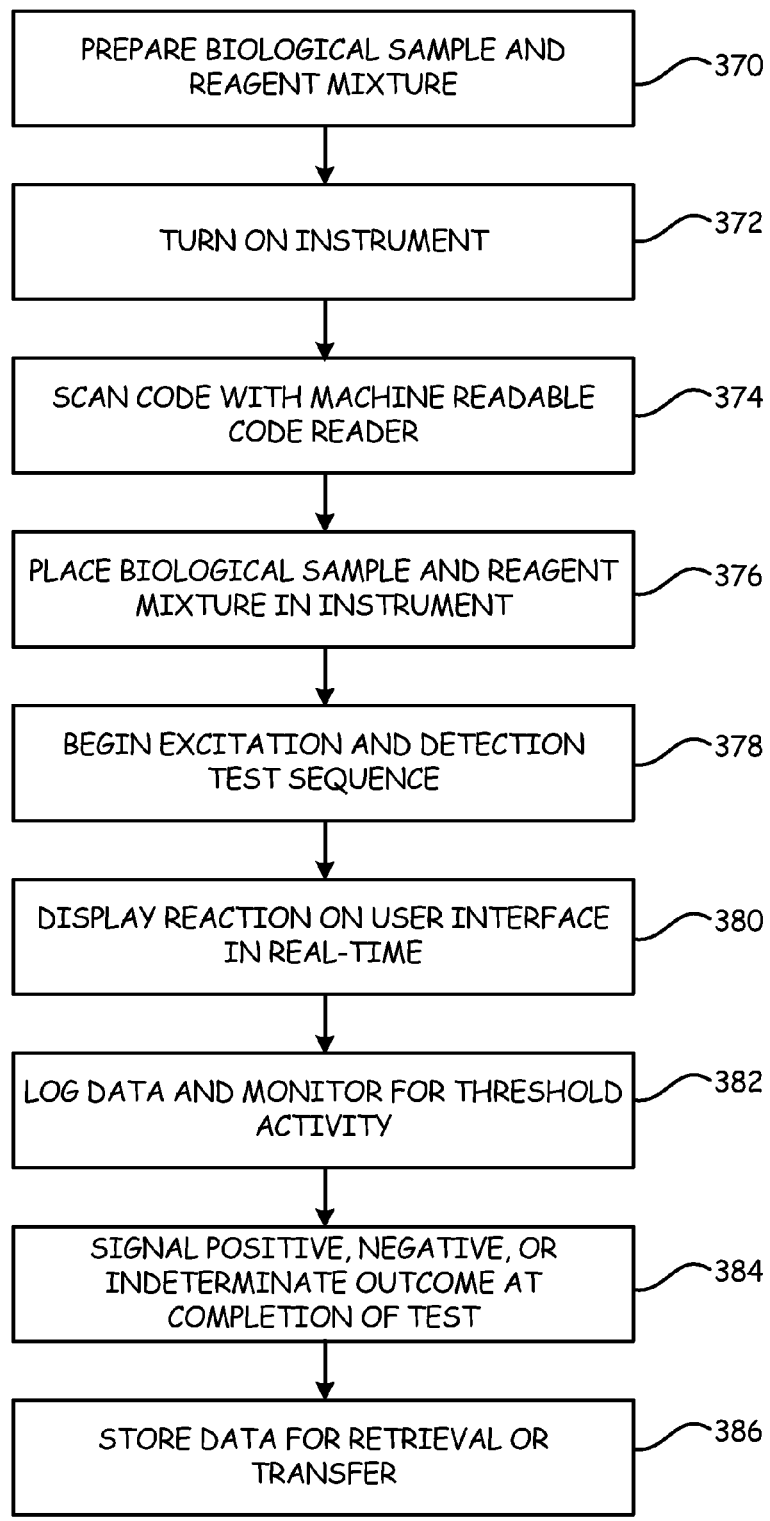
FIG. 14 is a flowchart showing steps for operating the portable testing device.

FIG. 14 is a flowchart showing steps for operating portable testing device 100. The flowchart includes steps 370-386. The process begins with step 370, which is preparing a biological sample and reagent mixture for testing. The reagent mixture can contain the master mix necessary for the desired assay, including fluorescent dyes or markers such as FAM or ROX, necessary for detecting the desired analyte in portable testing device 100. Once a user acquires a biological sample from the field, the biological sample can then be mixed with a reagent to form a biological sample and reagent mixture. More specifically, the biological sample is first mixed with a reaction buffer. Next, a portion of the biological sample and reaction buffer mixture is transferred to a sample holder containing a dried down master mix. This forms the biological sample and reagent mixture for testing.

In step 372, portable testing device 100 is turned on using power switch 126. In step 374, a code is scanned with machine readable code reader 154. The code will contain information about what test protocol is to be run and what parameters should be used. This information can be communicated through portable testing device 100 so that heating assembly 170 can begin heating to required temperature for the desired test protocol. In step 376, the user interface on display 116 will visually and audibly notify the user that portable testing device 100 is ready for testing. The user then opens lid 116 and places the sample holder with the biological sample and reagent mixture into heating assembly 170 in portable testing device 100.

In step 378, the user begins the excitation and detection sequence for the desired assay using the user interface on display 116. Optical assembly 156 begins the excitation and detection sequence. During the excitation and detection sequence, portable testing device 100 transmits emission data to electronic assembly 152 and display 116. Step 380 includes displaying the real time reaction data received from portable testing device 100 on the user interface on display 116. During step 382, electronic assembly 152 and display 116 logs the data received from portable testing device 100 and monitors the data for threshold activity. Once the assay is complete, during step 384, display 116 signals a positive, negative, or indeterminate outcome to the user. Finally, during step 386, electronic assembly 152 stores the data obtained for retrieval or transfer.

In general, the present invention relates to a portable testing device for analyzing biological samples. The portable testing device can be taken into the field to test biological samples as they are collected. This is advantageous over prior art systems, as it allows a user to test biological samples as the user is collecting them. This can prevent problems with contamination and degradation of biological samples due to transportation to a laboratory for testing, later discovery that not enough sample was taken, or later discovery that the collected biological sample is otherwise unsuitable for use. Allowing a user to test the biological sample in the field can save time, money, and resources. Testing in the field also provides the ability for rapid safety response if test results indicate a pathogen or toxin that may be harmful.

In the embodiment described below, the portable testing device is capable of testing biological samples with EnviroLogix's DNAble® chemistry, which employs an isothermal amplification process. This eliminates the need for thermocycling as a means to amplify nucleic acid products for endpoint detection. This allows a user to obtain data from the sample while the test is being run. In alternate embodiments, the portable testing device can be used to test biological samples with other isothermal amplification chemistries. The portable testing device displays this data so that a user can view the results of the test in the field. Allowing a user to view the results of the test in the field is advantageous, as the user can then make an informed decision of whether additional tests are needed. In alternate embodiments, the portable testing device is also capable of incorporating a thermocycler to allow for the use of non-isothermal polymerase chain reaction (PCR) chemistries and result in qPCR and end-point analysis.

Portable Testing Device 400 with Optical Assembly 418

Figure 15A:
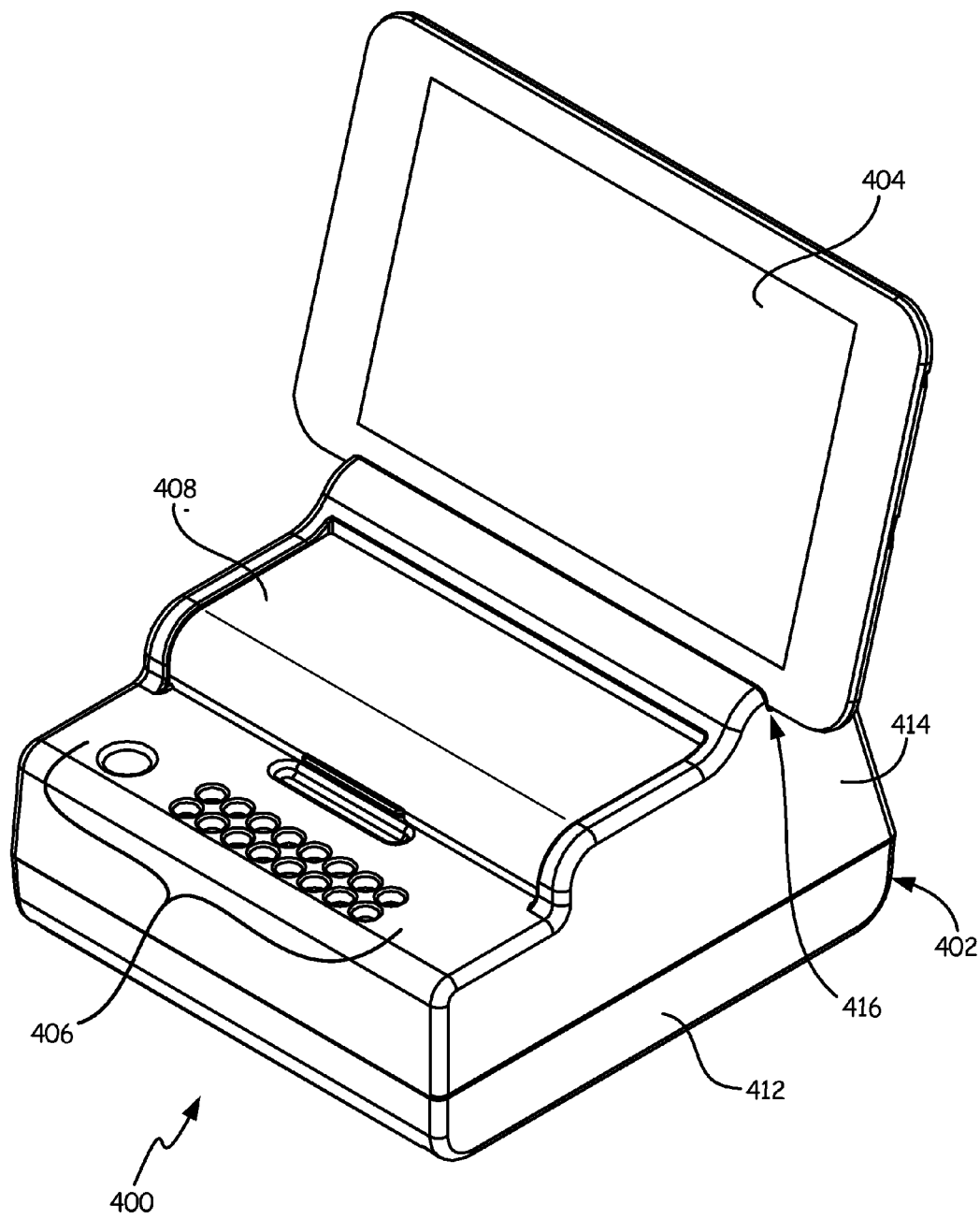
FIG. 15A is a perspective view of a portable testing device with a tablet computer positioned on the portable testing device.
Figure 15B:
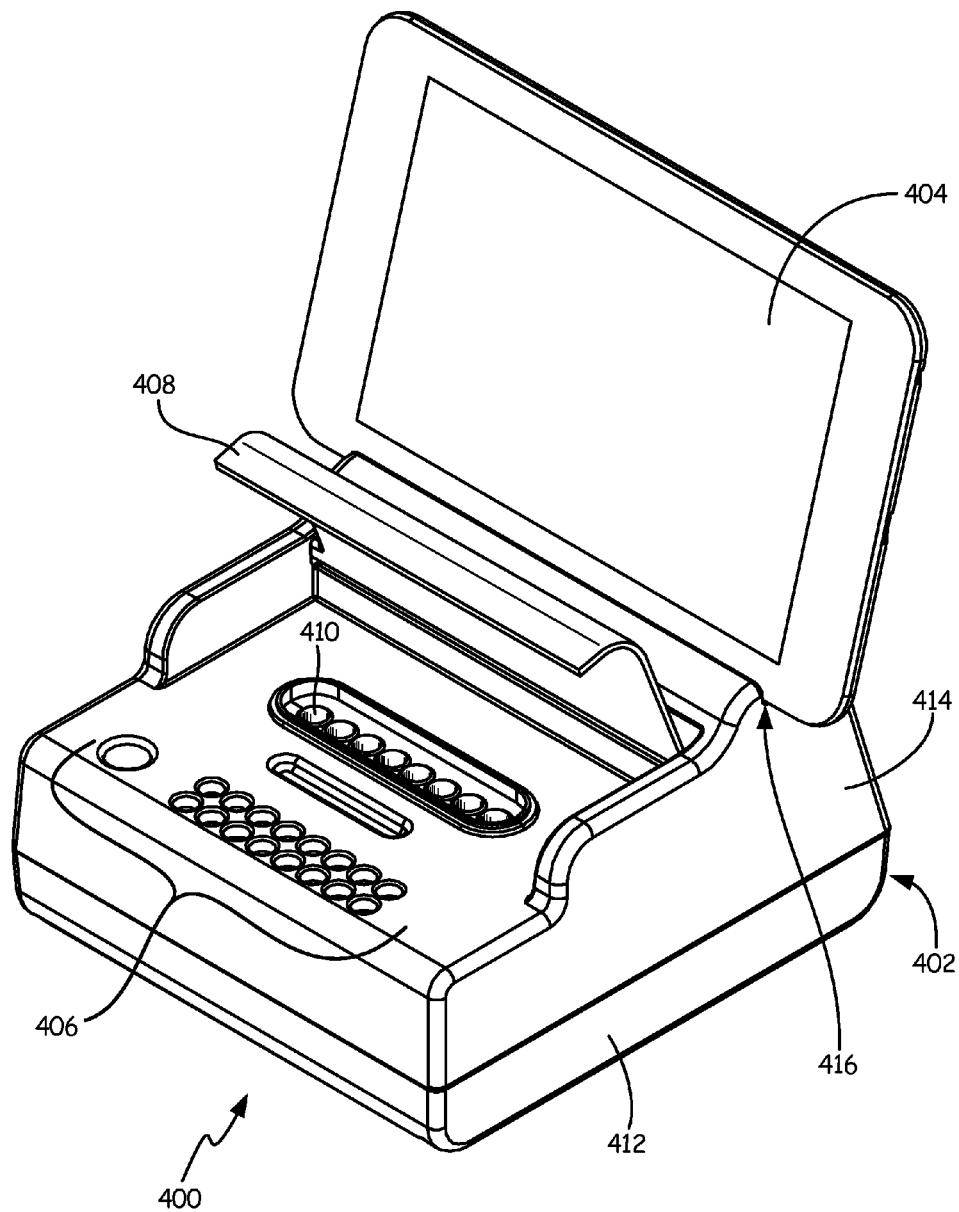
FIG. 15B is a perspective view of the portable testing device seen in FIG. 15A when an optical lid is opened.

FIG. 15A is a perspective view of portable testing device 400 with tablet computer 404 positioned on portable testing device 400. FIG. 15B is a perspective view of portable testing device 400, as seen in FIG. 15A, when optical lid 408 is opened. Portable testing device 400 includes housing 402 and tablet computer 404. Housing 402 includes sample preparation area 406, optical lid 408, housing opening 410, first housing portion 412, second housing portion 414, and cradle 416. Also included in portable testing device 400, but not shown in FIGS. 15A-15B, are an optical assembly and a power assembly.

Portable testing device 400 is an all-in-one device for sampling and testing biological samples in the field. Portable testing device 400 includes housing 402 and tablet computer 404. Housing 402 contains an optical assembly and a power assembly, not shown in FIGS. 15A-15B. The power assembly powers portable testing device 400 and is capable of being connected to tablet computer 102 to provide power to tablet computer 102. Tablet computer 102 communicates with portable testing device 400 using Bluetooth technology or other suitable wireless technology. The optical assembly is used to heat biological samples for isothermal nucleic acid amplification and to analyze biological samples once they are placed in portable testing device 400. The data collected during testing is transmitted to tablet computer 404, where it is displayed in real time. In the embodiment shown, the data is transferred wirelessly from portable testing device 400 to tablet computer 404, but in alternate embodiments a direct connection can be used.

Housing 402 includes sample preparation area 406, where biological samples can be prepared for testing. Sample preparation area 406 is positioned on a top surface of housing 402 of portable testing device 400. Sample preparation area 406 includes a plurality of apertures in housing 402 that can be used to prepare a biological sample for testing in portable testing device 400. Housing 402 also includes optical lid 408 that covers opening 410. Optical lid 408 can be opened so biological samples can be placed in opening 410 of housing 402 for testing. Once the biological samples are positioned in portable testing device 400, optical lid 408 is closed. The biological sample can then be tested using the optical assembly. Housing 402 also includes cradle 416 in which tablet computer 102 can be positioned.

Portable testing device 400 is advantageous, as it allows a user to test biological samples as they are collecting them in the field. This can prevent issues with contamination of the biological sample, as the biological sample is tested as it is collected. This can also prevent issues with biological samples that are collected and then later determined to be unsuitable for testing. Testing in the field allows a user to determine in real-time whether a biological sample is suitable for testing and prevents users from having to recollect samples, saving time and money. Data collected in the field can be stored on portable testing device 400 and downloaded or accessed later. Further, the data can be transmitted to a remote site via a telephone connection, an internet connection, or other suitable means. The data can also be transmitted using cloud computing for access later or immediately by another person for rapid evaluation and, if desired, closed-loop response.

Additionally, GPS capabilities can be incorporated to allow a user to track specific sampling locations and to verify that the testing was done at the correct location. A sampling location can be prescribed and plotted using the GPS mapping capabilities. As an example, a map of a corn field can be laid-out on the monitor and sample points predetermined (e.g., a location of a specific corn plant) either graphically or with GPS coordinates. The user can observe the monitor and utilize the GPS coordinates to arrive at the proper sample point.

Figure 16A:
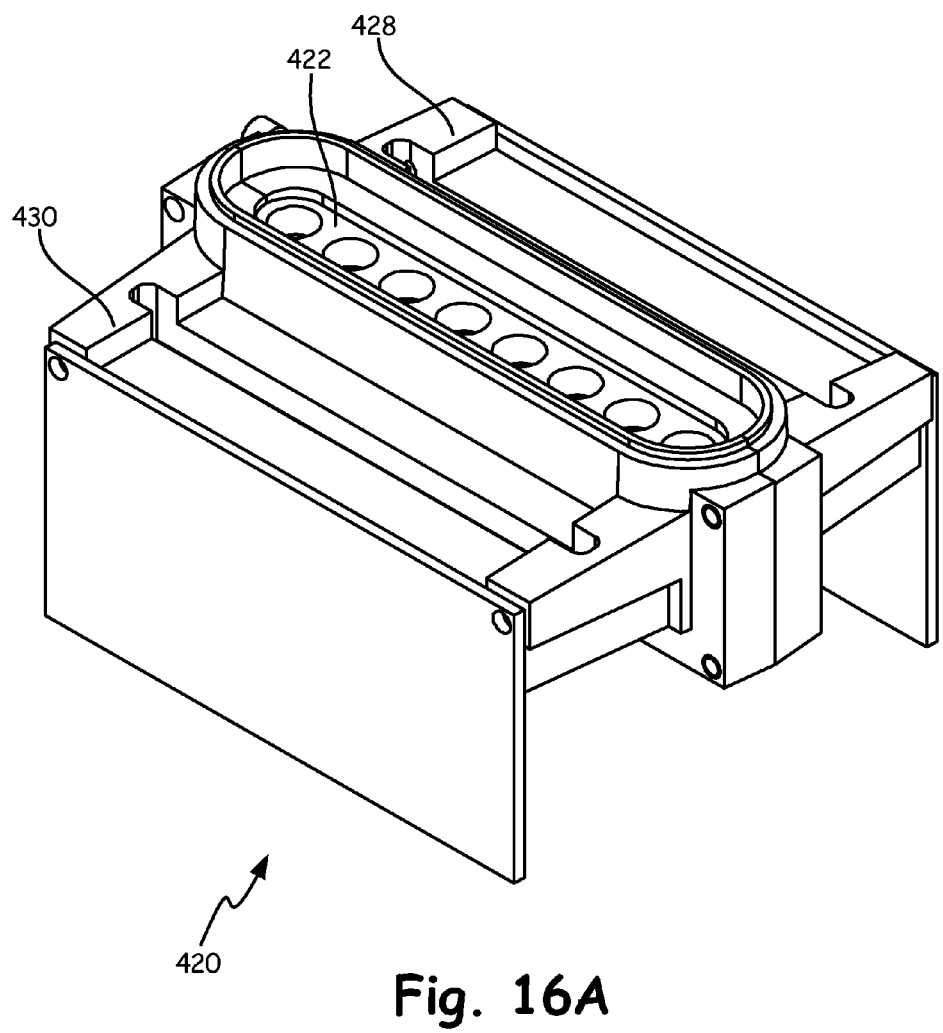
FIG. 16A is a perspective view of an upper optical assembly.
Figure 16B:
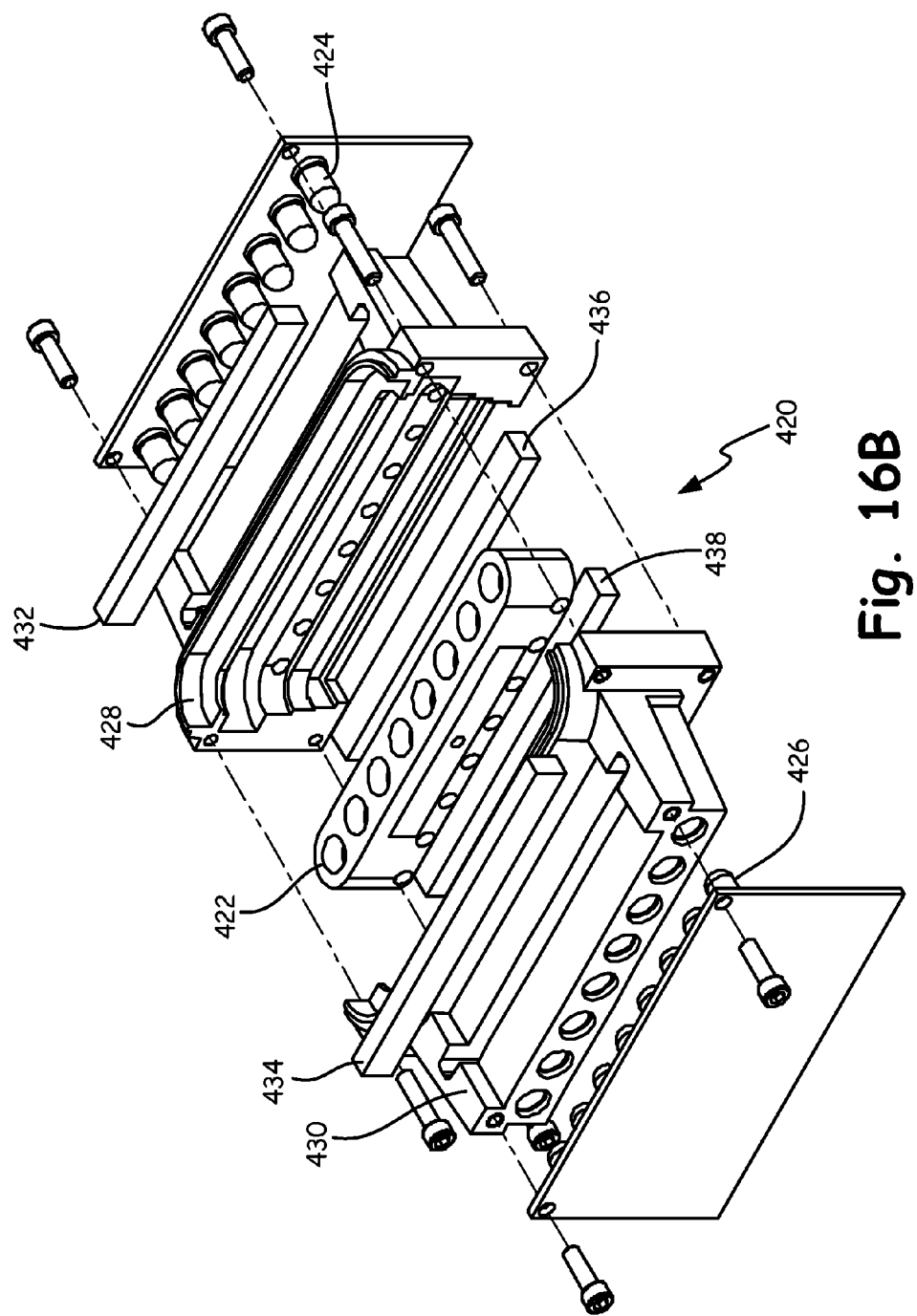
FIG. 16B is an exploded view of the upper optical assembly seen in FIG. 16A.

FIG. 16A is a perspective view of upper optical assembly 420. FIG. 16B is an exploded view of upper optical assembly 420, as seen in FIG. 16A. Upper optical assembly 420 includes heating component 422, first plurality of light-emitting diodes 424, second plurality of light-emitting diodes 426, first structural component 428, second structural component 430, first filter 432, second filter 434, third filter 436, and fourth filter 438.

Upper optical assembly 420 is one of two parts that form the optical system for portable testing device 400. Upper optical assembly 420 includes first plurality of light-emitting diodes 424 and second plurality of light-emitting diodes 426 that are used to excite a biological sample when it is placed in portable testing device 400 for testing. First plurality of light-emitting diodes 424 are located on a first side of upper optical assembly 420. In the embodiment shown, first plurality of light-emitting diodes 424 are blue light-emitting diodes to excite Fluorescein amidite (FAM) fluorescence dye. Second plurality of light-emitting diodes 426 are located on a second side of upper optical assembly 420. In the embodiment shown, second plurality of light-emitting diodes 426 are amber light-emitting diodes to excite 6-Carboxyl-X-Rhodamine (ROX) fluorescence dye. In alternate embodiments, first plurality of light-emitting diodes 424 and second plurality of light-emitting diodes 426 can be any color light-emitting diodes corresponding to the dye or marker used in testing a biological sample.

Upper optical assembly also includes heating component 422. Heating component 422 is a heat block in the embodiment shown, but can be any suitable heating component in alternate embodiments. Heating component 422 is capable of heating from an ambient temperature to a temperature of about 95 degrees Celsius. Heating component 422 has a plurality of apertures running from a top side of heating component 422 to a bottom side of heating component 422 in which an array of tubes can be placed. The array of tubes will extend completely through and beyond the plurality of apertures in heating component 422. This allows first plurality of light-emitting diodes 424 and second plurality of light-emitting diodes 426 to pass light to the array of tubes to excite the biological sample in the array of tubes.

First structural component 428 and second structural component 430 form a structural basis for upper optical assembly 420. First structural component 428 is positioned between first plurality of light-emitting diodes 424 and the first side of heating component 422. First plurality of light-emitting diodes are positioned so that they extend into first structural component 428. Second structural component 430 is positioned between second plurality of light-emitting diodes 426 and the second side of heating component 422. Second plurality of light-emitting diodes are positioned so that they extend into second structural component 430. First structural component 428 and second structural component 430 further act as heat insulators and prevent heat from escaping heating component 422. This improves the effectiveness and reliability of heating component 422. First structural component 428 and second structural component 430 provide a path through which light from first plurality of light-emitting diodes 424 and second plurality of light-emitting diodes 426 can travel. This prevents light from being lost and increases the effectiveness of first plurality of light-emitting diodes 424 and second plurality of light-emitting diodes 426 exciting the biological sample that is placed in heating component 422.

First structural component 428 and second structural component 430 further include a cut out portion in which first filter 432 and second filter 434 can each be placed, respectively. First filter 432 and second filter 434 are both excitation filters to filter light from light-emitting diodes as it passes through to excite a biological sample. Light from first plurality of light-emitting diodes 424 passes through first filter 432 that is placed in first structural component 428 before the light passes into the biological sample in heating component 422. First filter 432 is a 490 nanometer filter in the embodiment shown to align with FAM excitation. Light from second plurality of light-emitting diodes 426 passes through second filter 434 that is placed in second structural component 430 before the light passes into the biological sample in heating component 422. Second filter 434 is a 580 nanometer filter in the embodiment shown to align with ROX excitation. In alternate embodiments, first filter 432 and second filter 434 can be any filters to align with different fluorescent dyes or markers.

Upper optical assembly 420 also includes third filter 436 and fourth filter 438. Third filter 436 and fourth filter 438 are both emission filters that filter light to photodiodes 142 and 144, respectively (shown in FIG. 3B). Photodiodes 142 and 144 are positioned underneath heating component 422 in a lower optical assembly, described in relation to FIGS. 3A-3B below. Third filter 436 is positioned between a first plurality of photodiodes and heating component 422. Third filter 436 is a 610 nanometer filter in the embodiment shown to align with ROX emission. Fourth filter 438 is positioned between a second plurality of photodiodes and heating component 422. Fourth filter 438 is a 520 nanometer filter in the embodiment shown to align with FAM emission. In alternate embodiments, third filter 436 and fourth filter 438 can be any filters to align with different fluorescent dyes or markers.

Upper optical assembly 420 is designed to excite biological samples that are placed in portable testing device 400 for testing. Upper optical assembly 420 is advantageous, as it contains light from first plurality of light-emitting diodes 424 and second plurality of light-emitting diodes 426. This prevents light from escaping and ensures accurate and reliable results every time portable testing device 400 is used to analyze biological samples.

Figure 17A:
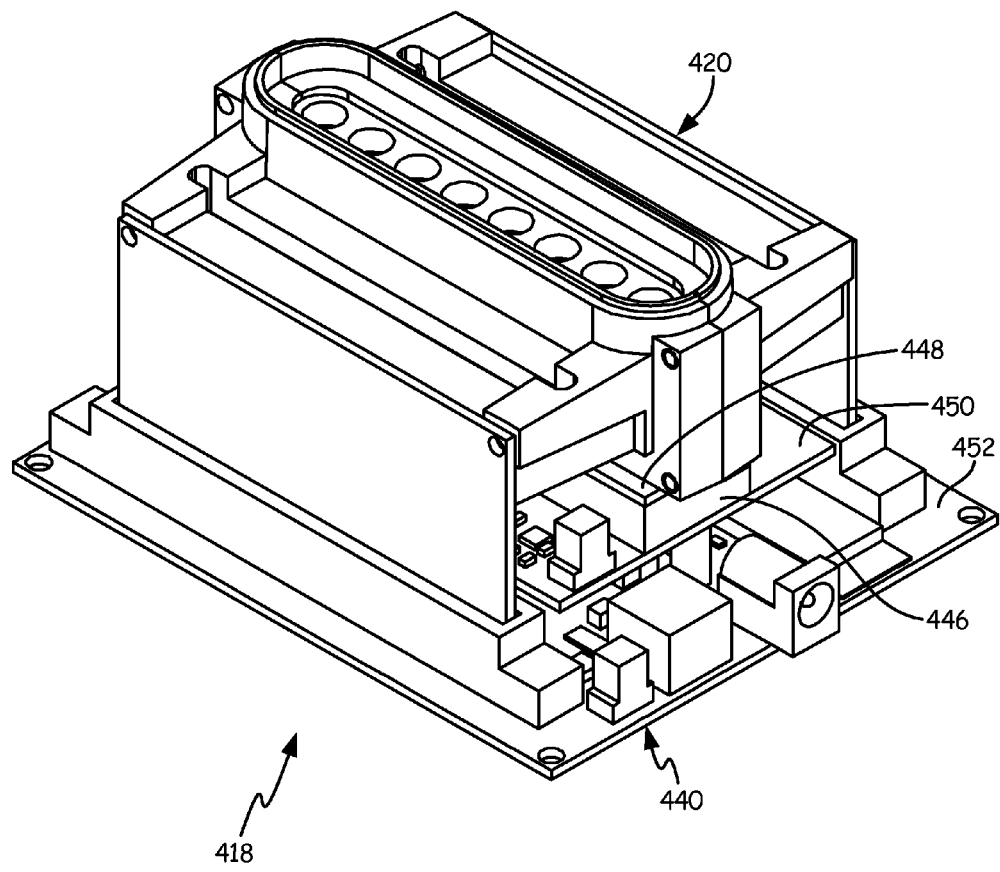
FIG. 17A is a perspective view of an optical assembly, including the upper optical assembly seen in FIGS. 16A-16B and a lower optical assembly.
Figure 17B:
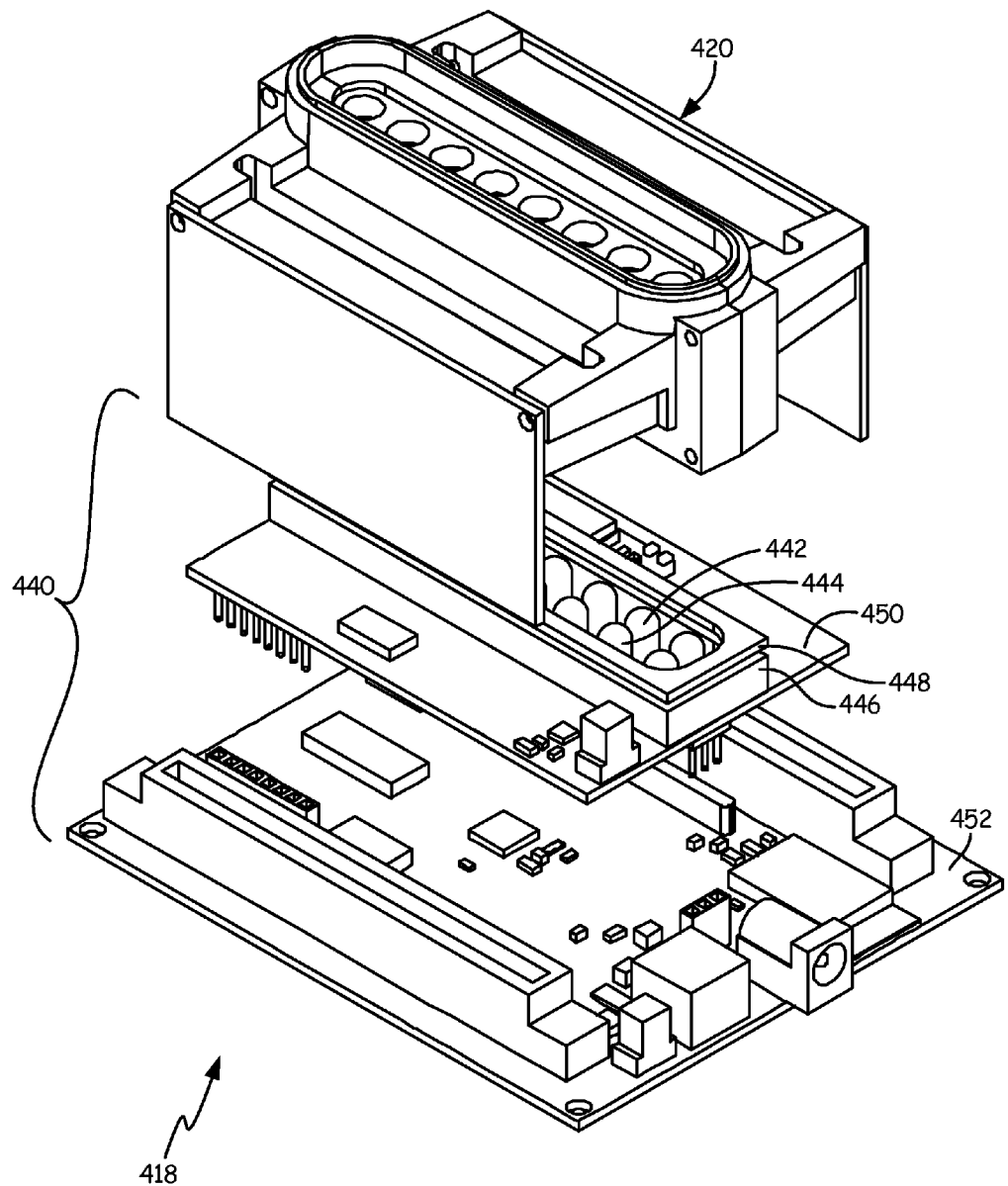
FIG. 17B is an exploded view of the optical assembly seen in FIG. 17A.

FIG. 17A is a perspective view of optical assembly 418, including upper optical assembly 420, as seen in FIGS. 16A-16B, and lower optical assembly 440. FIG. 17B is an exploded view of optical assembly 418, as seen in FIG. 17A. Upper optical assembly 420 is described above in relation to FIGS. 16A-16B. Lower optical assembly 440 includes first plurality of photodiodes 442, second plurality of photodiodes 444, spacer 446, gasket 448, upper board 450, and lower board 452. Also include in lower optical assembly 440 are electronic components for controlling optical assembly 418, including electronic components to control heating of heating component 422.

Lower optical assembly 440 is positioned below upper optical assembly 420 to form optical assembly 418. Lower optical assembly 440 includes first plurality of photodiodes 442 and second plurality of photodiodes 444. First plurality of photodiodes 442 are positioned in a first row on upper board 450. Second plurality of photodiodes 444 are positioned in a second row on upper board 450. Upper board 450 is placed under upper optical assembly 420 so that first plurality of photodiodes 442 and second plurality of photodiodes 444 are positioned under heating component 422 of upper optical assembly 420. This allows first plurality of photodiodes 442 and second plurality of photodiodes 444 to detect fluorescent emissions from biological samples that are placed in the array of tubes in heating component 422. In the embodiment shown, first plurality of photodiodes 442 are selected to align with ROX emission and second plurality of photodiodes 444 are selected to align with FAM emission. In alternate embodiments, first plurality of photodiodes 442 and second plurality of photodiodes 444 can be selected to align with different fluorescent dyes or markers.

Lower optical assembly 440 also includes spacer 446 and gasket 448. Spacer 446 extends between upper board 450 to a bottom side of first structural component 428 and second structural component 430 of upper optical assembly 420. Spacer 446 is placed around first plurality of photodiodes 442 and second plurality of photodiodes 444. This contains light from first plurality of photodiodes 442 and second plurality of photodiodes 444 and directs the light to the bottom of the array of tubes that are placed in upper optical assembly 420. Gasket 448 is positioned on top of spacer 446 to form a seal between spacer 446 and upper optical assembly 420.

First plurality of photodiodes 442, second plurality of photodiodes 444, spacer 446, and gasket 448 are all positioned on upper board 450. Upper board 450 is then positioned on lower board 452 to form lower optical assembly 156. Electrical components are placed on upper board 450 and lower board 452 to run optical assembly 418, including heating of heating component 422.

Optical assembly 418, including both upper optical assembly 420 and lower optical assembly 440, is capable of performing both excitation and detection of biological samples that are placed in portable testing device 400. Optical assembly 418 is designed to be compact to allow it to be used in portable testing device 400. Being compact is advantageous, as it allows excitation and detection of biological samples to occur in the field as biological samples are collected. Optical assembly 418 can additionally include a light barrier around optical assembly 418 to prevent light from escaping optical assembly 418. In a first embodiment, the light barrier can include surrounding optical assembly 418 with light proofing tape. In an alternate embodiment, the light barrier can include a housing around optical assembly 418 to prevent light from escaping.

In the embodiment seen in FIGS. 17A-17B, optical assembly 418 is designed to be compatible with EnviroLogix's DNAble® chemistry, which employs an isothermal amplification process. The reaction proceeds at a single, elevated temperature, usually 56 degrees Celsius. DNAble® chemistry allows amplification to be completed in less than ten minutes. In alternative embodiments, optical assembly 418 may be used for other chemistries such as assays relating to *Salmonella*, soy lectin, genetically modified organisms, *E. coli*, and influenza.

Figure 18A:
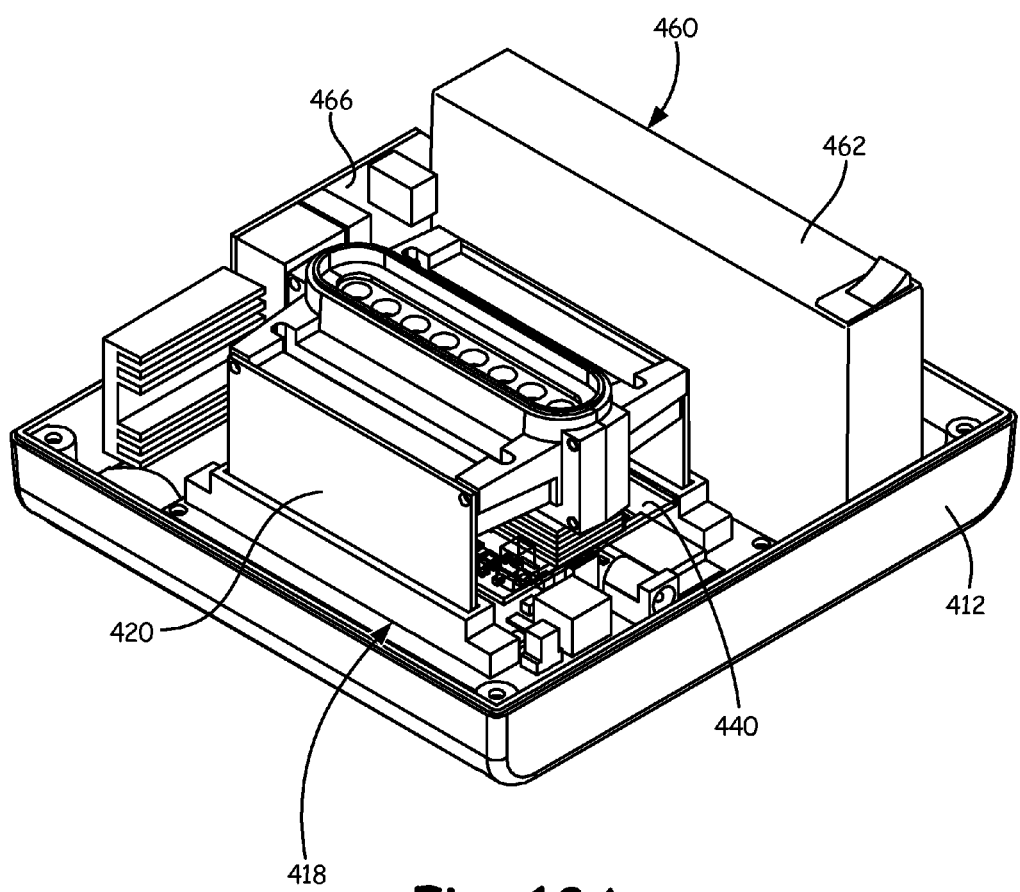
FIG. 18A is a perspective view of a lower portion of the portable testing device, including the optical assembly seen in FIGS. 16A-16B and a power assembly.
Figure 18B:
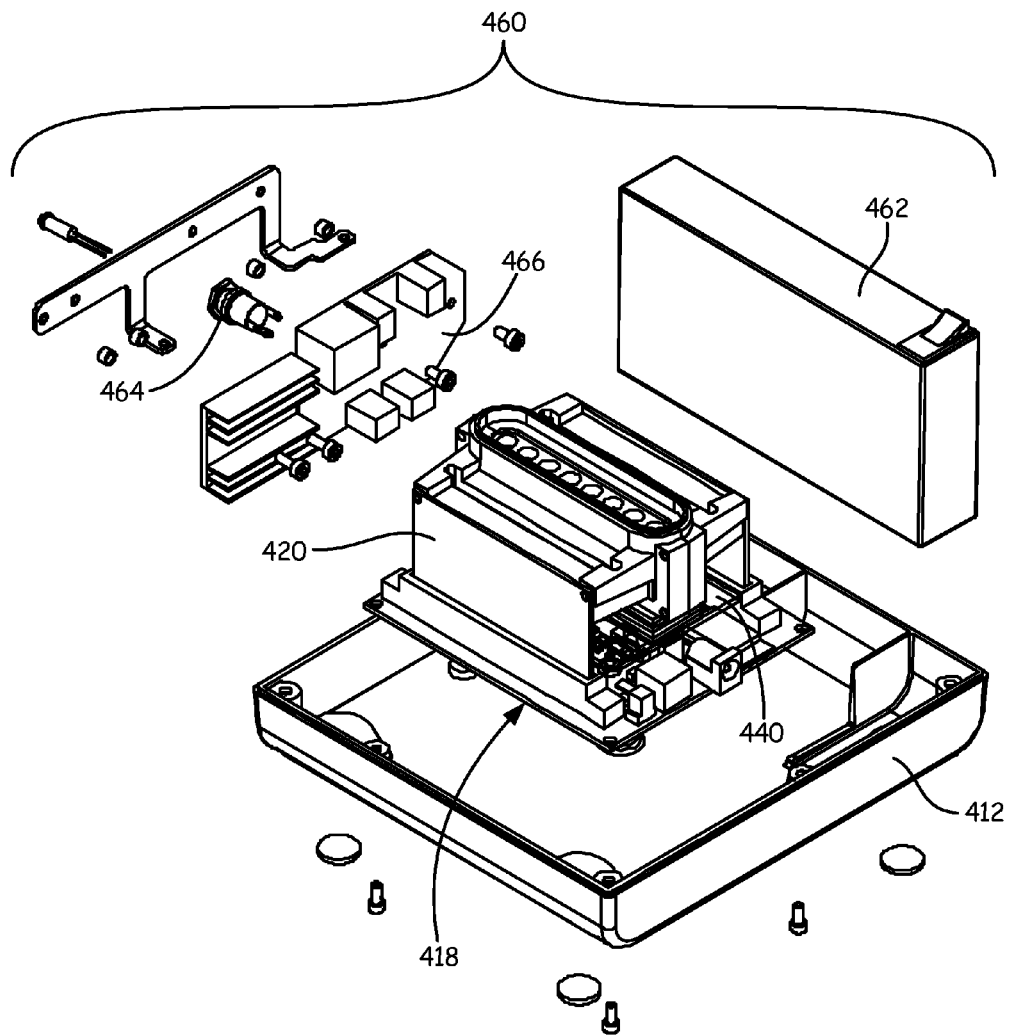
FIG. 18B is an exploded view of the lower portion of the portable testing device seen in FIG. 18A.

FIG. 18A is a perspective view of a lower portion of portable testing device 400, including optical assembly 418, as seen in FIGS. 17A-17B, and power assembly 460. FIG. 18B is an exploded view of the lower portion of portable testing device 400, as seen in FIG. 18A. The lower portion of portable testing device 400 including first housing portion 412, optical assembly 418, and power assembly 460. Optical assembly 418 includes upper optical assembly 420 and lower optical assembly 440. Power assembly 460 includes battery 462, power jack 464, and power board 466.

Portable testing device 400 includes first housing portion 412 that acts as a base for portable testing device 400. Optical assembly 418 and power assembly 460 are placed in first housing portion 412. Optical assembly 418 includes upper optical assembly 420 for excitation that is attached to lower optical assembly 440 for detection. Optical assembly 418 is positioned in first housing portion 412 so heating component 422 of upper optical assembly 420 aligns with the opening in portable device 100 to receive the biological sample. Power assembly 460 is positioned in first housing portion 112 around optical assembly 418 to utilize all of the space in first housing portion 412. This allows portable testing device 400 to be as compact as possible for use as a hand-held device.

Power assembly 460 includes battery 462. Battery 462 powers portable testing device 400 so that portable testing device 400 can be used in the field. Battery 462 is also capable of powering tablet computer 404, shown in FIGS. 15A-15B. Tablet computer 404 can be connected to power assembly 460 with a pigtail connection and powered through battery 462 or AC power.

Power assembly 460 further includes power board 466. Power board 466 consolidates and distributes power throughout portable testing device 400. Power jack 464 is also included in power assembly 460 so that power assembly 460 can be connected to a power source to recharge battery 462 and tablet computer 404. Including power assembly 460 on portable testing device 400 is advantageous, as it allows portable testing device to be used in the field. In alternate embodiments, portable testing device 400 can utilize solar cells, wind generators, manual electrical generators, or other suitable means to provide power to the unit. These alternate embodiments allow portable testing device 400 to be used in remote areas where power is not available or where batteries are not available or affordable.

Figure 19A:
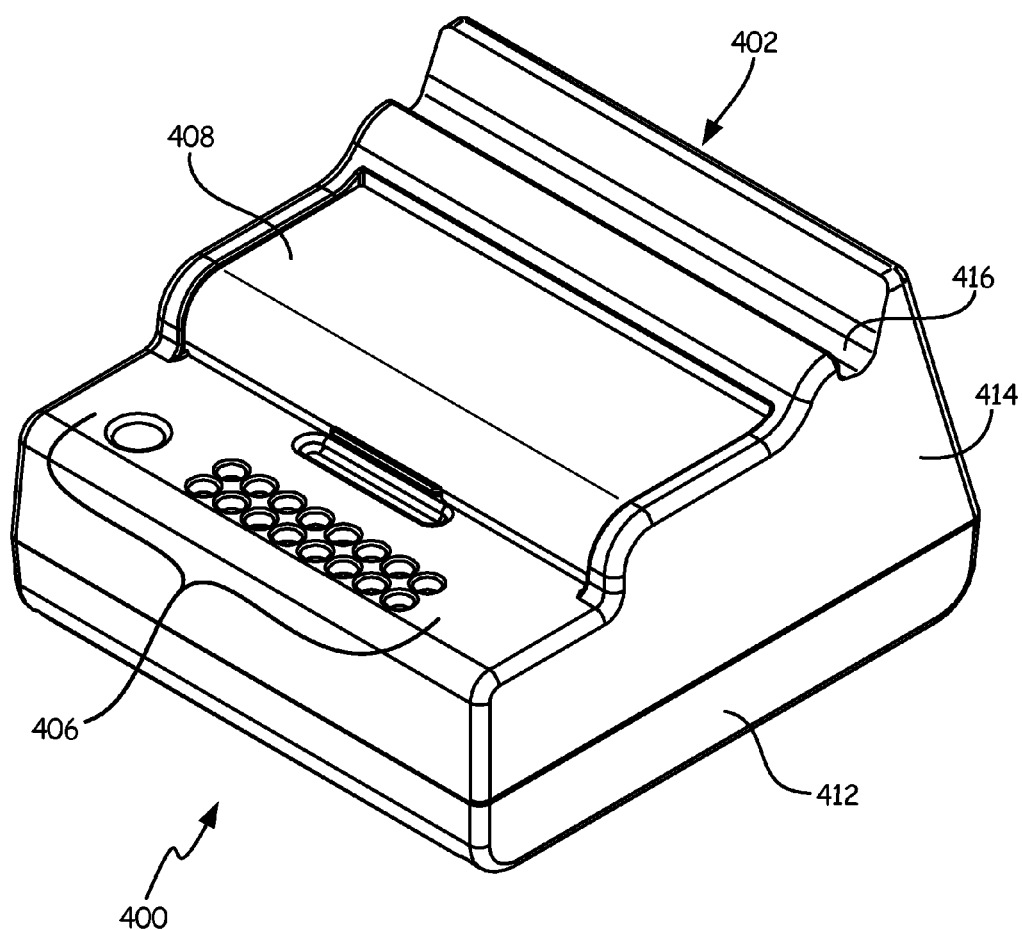
FIG. 19A is a perspective view of the portable testing device.
Figure 19B:
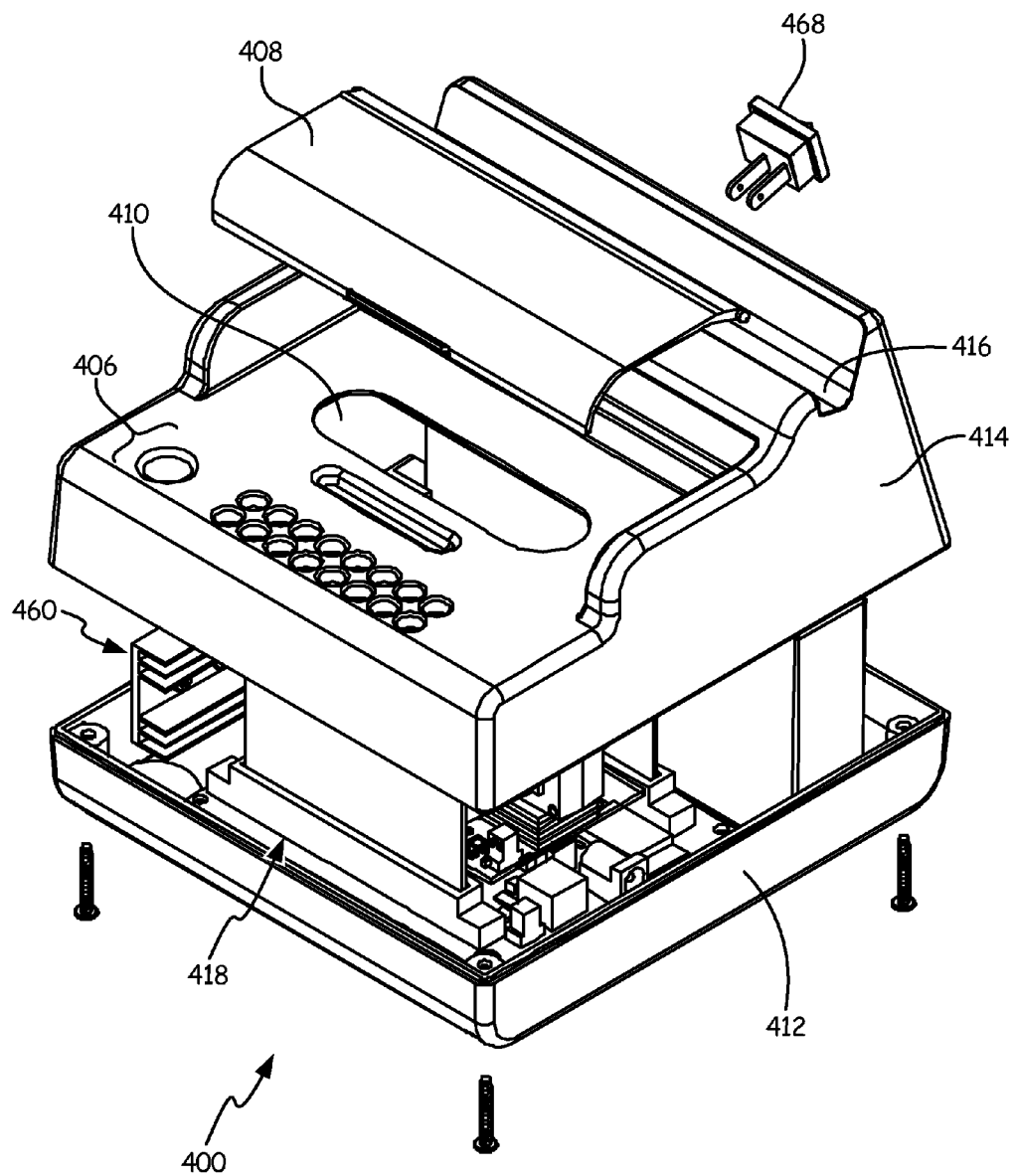
FIG. 19B is an exploded view of the portable testing device seen in FIG. 19A.

FIG. 19A is a perspective view of portable testing device 400. FIG. 19B is an exploded view of portable testing device 400, as seen in FIG. 19A. Portable testing device 400 includes housing 402, sample preparation area 406, optical lid 408, opening 410, cradle 416, optical assembly 418, power assembly 460, and power switch 468. Housing 402 includes first housing portion 412 and second housing portion 414.

First housing portion 412 forms a base for portable testing device 400, and second housing portion 414 is positioned on top of first housing portion 412. First housing portion 412 and second housing portion 414 are held together with fasteners in the embodiment shown, but can be held together with any suitable means in alternate embodiments.

Housing 402 contains optical assembly 418 and power assembly 460. Optical assembly 418 tests biological samples that are placed in portable testing device 400. Power assembly 460 powers portable testing device and is capable of powering a tablet computer that can be positioned on portable testing device 400. Power switch 468 extends between power assembly 460 and an outside of housing 402. Power switch 468 allows a user to easily turn portable testing device 400 on and off. Cradle 416 is a groove that extends from a first side to a second side of portable testing device 400 on a top side of housing 402. A tablet computer can be placed in cradle 416 when to set up the assay protocol, receive data from portable testing device 400, and display the results of the test in real-time.

Sample preparation area 406 is on a top side of housing 402. Sample preparation area 406 is used to prepare a biological sample for testing. Opening 410 is on a top side of housing 402. Opening 410 is positioned over optical assembly 418 so that an array of tubes containing a biological sample can be placed through opening 410 and into optical assembly 418 for testing. Optical lid 408 is positioned over opening 410 and is connected to housing 402 along a hinge. Optical lid 408 can be opened so that biological samples can be placed in opening 410 and then closed during testing.

Figure 20A:
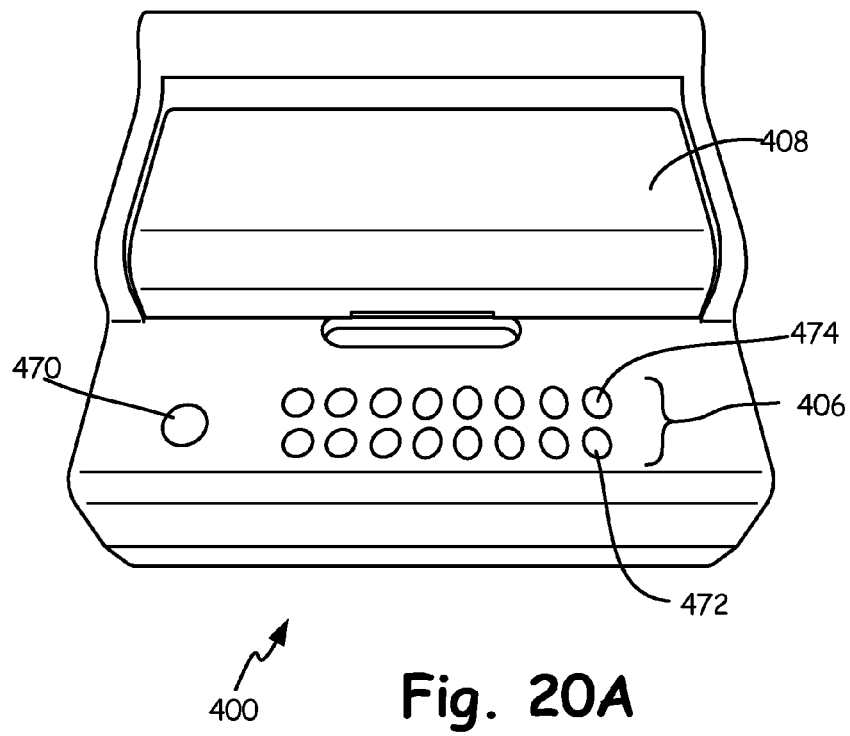
FIG. 20A is a perspective view of a sample preparation area on the portable testing device.
Figure 20B:
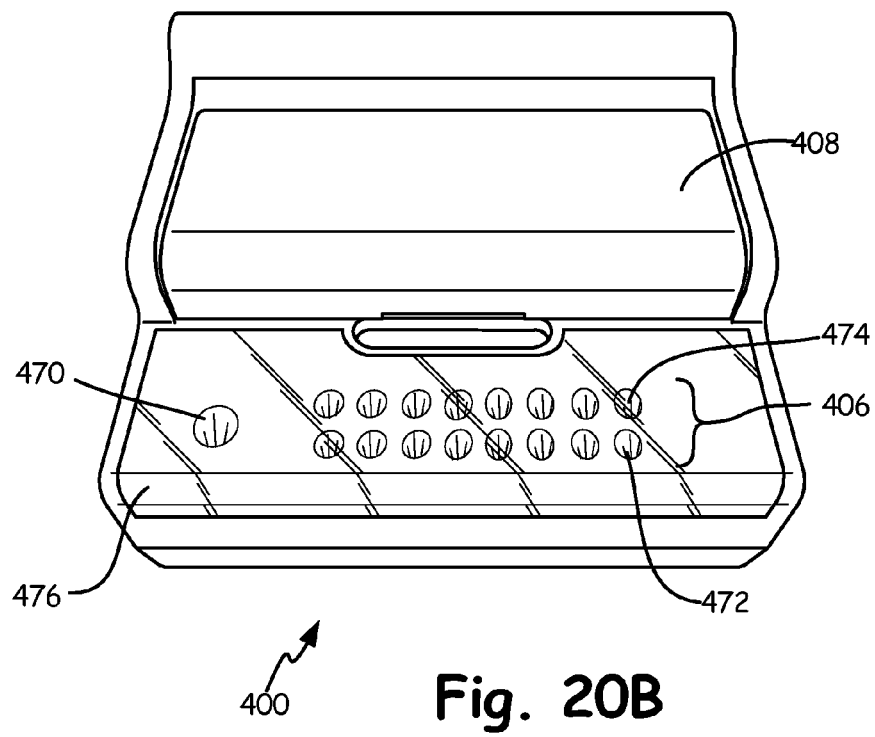
FIG. 20B is a perspective view of a film cover over the sample preparation area on the portable testing device.
Figure 20C:
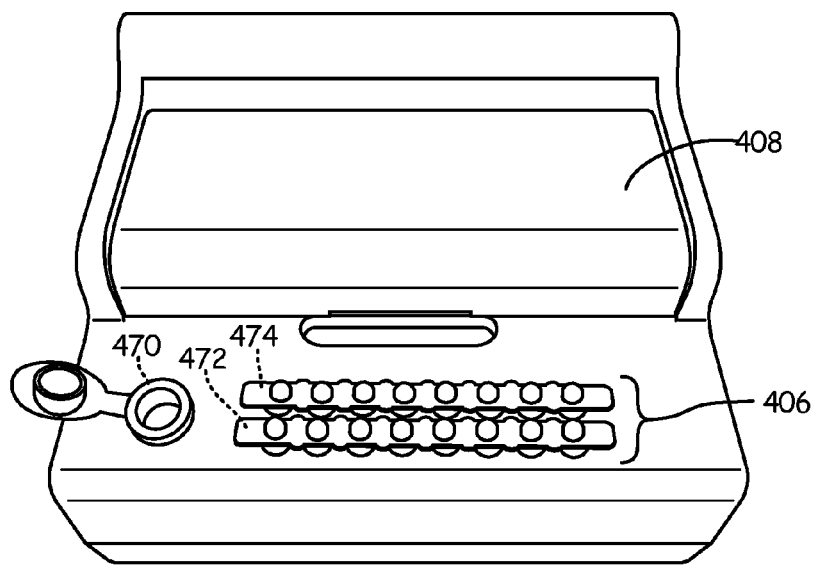
FIG. 20C is a perspective view of the sample preparation area seen in FIG. 20A, when sample arrays are positioned in the sample preparation area.
Figure 20D:
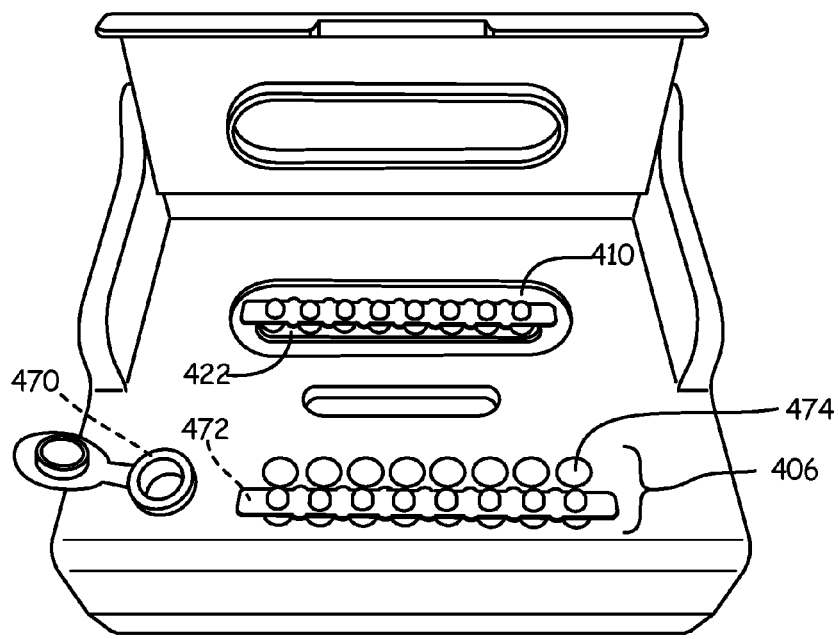
FIG. 20D is a perspective view of the sample preparation area seen in FIG. 20A when a sample array has been positioned in the portable testing device.

FIG. 20A is a perspective view of sample preparation area 406 on portable testing device 400. FIG. 20B is a perspective view of film cover 476 over sample preparation area 406 on portable testing device 400. FIG. 20C is a perspective view of sample preparation area 406 seen in FIG. 20A, when sample arrays are positioned in sample preparation area 406. FIG. 20D is a perspective view of sample preparation area 406 seen in FIG. 20A when a sample array has been positioned in portable testing device 400. Portable testing device 400 includes sample preparation area 406, optical lid 408, opening 410, and heating component 422. Sample preparation area 406 includes tube receptacle 470, first plurality of tube receptacles 472, and second plurality of tube receptacles 474. Also shown in FIG. 20B is film cover 476.

Sample preparation area 406 includes tube receptacle 470 located on a first side of sample preparation area 406, first plurality of tube receptacles 472 located in a row on a front side of sample preparation area 406, and second plurality of tube receptacles 474 located in a row on a back side of sample preparation area 406. In the embodiment seen in FIGS. 20A-20D, a single tube containing a biological sample can be placed in tube receptacle 470, an array of tubes containing a reaction buffer can be placed in first plurality of tube receptacles 472, and an array of tubes containing a master mix can be placed in second plurality of tube receptacles 474. In alternate embodiments, sample preparation area 406 can include a plurality of tube receptacles 170 to contain a plurality of biological samples. In further alternate embodiments, sample preparation area 406 can include one or more heating components positioned in tube receptacle 470, first plurality of tube receptacles 472, or second plurality of tube receptacles 474. Placing heating components in sample preparation area 406 allows the biological sample, reaction buffer, and/or master mix to be heated during preparation of the biological sample. Heating the biological sample, reaction buffer, and/or master mix while preparing the biological sample will help to lyse the biological sample collected in the field to prepare the biological sample for testing. In alternate embodiments, sample preparation area 406 can be provided separate from portable testing device 400 and can include additional receptacles and heating components.

As seen in FIG. 20B, film cover 476 can be positioned over sample preparation area 406. Film cover 476 is a preformed film structure with a flat portion that can be placed against the top surface of sample preparation area 406 and a plurality of sleeves that can be positioned in each of tube receptacle 470, first plurality of tube receptacles 472, and second plurality of tube receptacles 474. Film cover 476 can be placed on sample preparation area 406 before each test and removed from sample preparation area 406 after each test to prevent contamination between tests. In an alternate embodiment, film cover 476 can be made of a high-temperature film and extended to cover heating component 422.

As seen in FIG. 20C, the biological sample can be prepared for testing on sample preparation area 406 by distributing the biological sample from the single tube in tube receptacle 470 into the array of tube containing the reaction buffer in first plurality of tube receptacles 472. The mixture of the reaction buffer and biological sample can then be transferred from the array of tubes in first plurality of tube receptacles 472 into the array of tubes in second plurality of tube receptacles 474. This will mix the biological sample and reaction buffer with the master mix containing the necessary reagents to carry out a desired assay, including fluorescent dyes or markers, such as ROX or FAM. In alternate embodiments, the steps for preparing the sample can vary and different solutions can be used.

When the biological sample is prepared for testing, optical lid 408 can be opened to reveal opening 410 and heating component 422. The array of tubes in second plurality of tube receptacles 474 can then be placed through opening 410 in the apertures in heating component 422, as seen in FIG. 20D. This will position the array of tubes for testing with the optical system in portable testing device 400.

Preparing biological samples on sample preparation area 406 is advantageous, as it allows a user to collect a sample, prepare the sample, and test the sample all in one hand-held device. This allows a user to easily prepare and test the sample in the field, without having to take the sample back to a laboratory to prepare it. It also allows a user to avoid having to carry multiple devices along when the user is testing biological samples in the field, because a separate sample preparation device is not needed.

Figure 21:
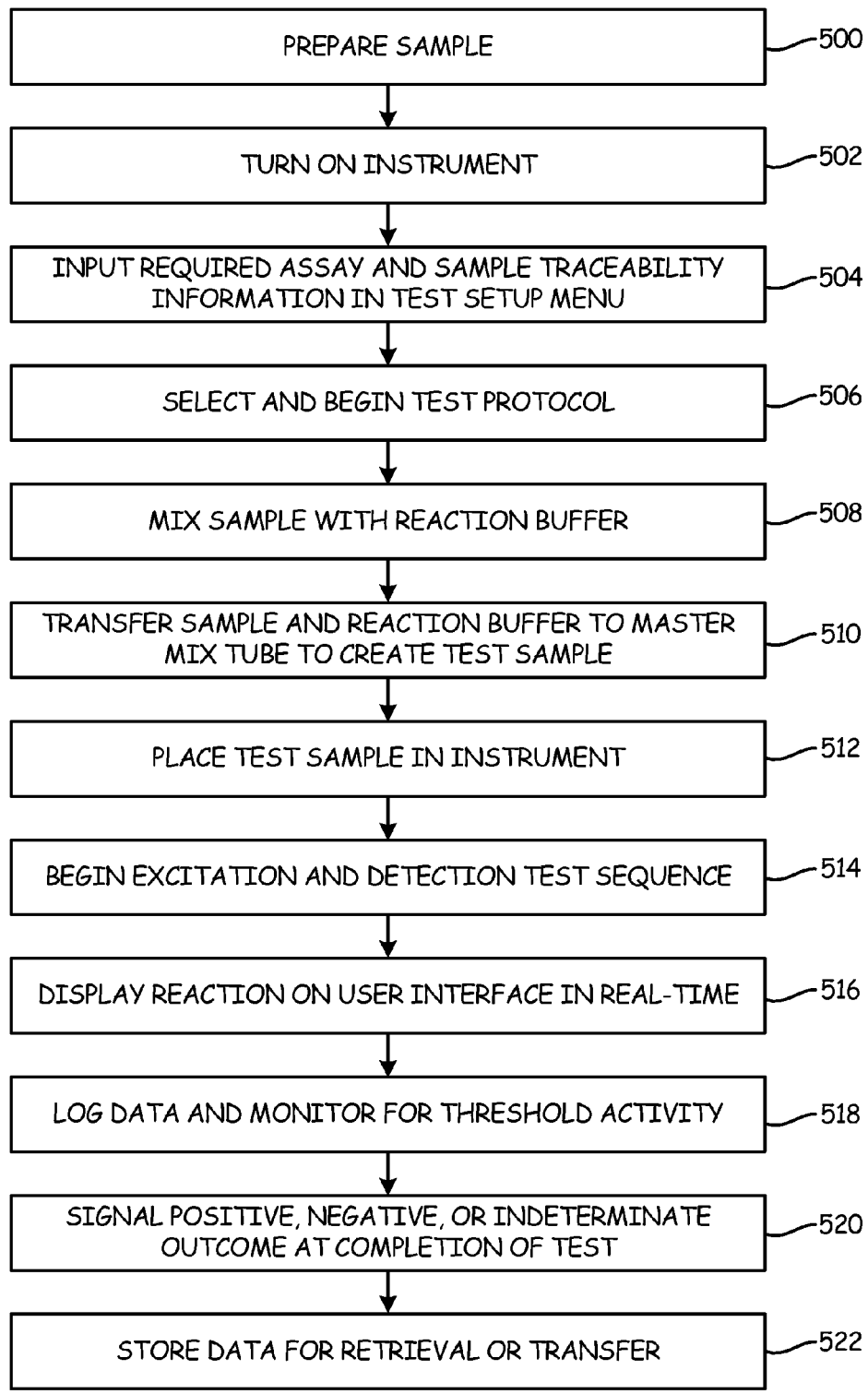
FIG. 21 is a flowchart showing steps for operating the portable testing device.

FIG. 21 is a flowchart showing steps for operating portable testing device 400. The flowchart includes steps 500-522. The process begins with step 500, sample preparation. Once a user acquires a sample from the field, it can be inserted into tube receptacle 470 in sample preparation area 406 of portable testing device 400. The field sample may be heated in sample preparation area 406 to aid in the release of a biological sample from the field sample. In step 502, portable testing device 400 is turned on using power switch 468. In step 504, the user then inputs a required assay and sample traceability information in the test setup menu on tablet computer 404, which sits in cradle 416 of housing 402 of portable testing device 400. In step 506, the user then selects and begins the test protocol for the desired assay. When the test protocol is initiated, heating component 422 begins to heat to the required temperature for the desired assay.

While heating component 422 is heating up, in step 508, in an array of tubes in first plurality of tube receptacles 472, the user mixes the biological sample from tube receptacle 470 with reaction buffer necessary for the desired assay. In step 510, the user transfers the sample and reaction buffer mixture from the array of tubes in first plurality of tube receptacles 472 to a corresponding array of tubes in second plurality of tube receptacles 474. The array of tubes in second plurality of tube receptacles 474 contains a master mix required for the desired assay, including fluorescent dyes or markers such as FAM or ROX, necessary for detecting the desired analyte in portable testing device 400. The master mix can be liquid or lyophilized. The user mixes the sample and buffer mixture with the master mix in the array of tubes in the second plurality of tube receptacles 474. In step 512, the user interface on tablet computer 404 will visually and audibly notify the user that portable testing device 400 is ready for testing. The user then seals the array of tubes in second plurality of tube receptacles 474, opens lid 108 and transfers the array of tubes through opening 410 into the plurality of apertures in heating component 422.

In step 514, the user begins the excitation and detection sequence for the desired assay on tablet computer 404. Optical system 118 begins the excitation and detection sequence. During the excitation and detection sequence, portable testing device 400 transmits emission data to tablet computer 404. Step 516 includes displaying the real time reaction data received from portable testing device 400 on the user interface on tablet computer 404. During step 518, tablet computer 404 logs the data received from portable testing device 400 and monitors the data for threshold activity. Once the assay is complete, during step 520, tablet computer 404 signals a positive or negative outcome to the user. Finally, during step 522, tablet computer 404 may store the data obtained for retrieval or transfer.

In general, the present invention relates to a portable testing device for analyzing biological samples. The portable testing device can be taken into the field to test biological samples as they are collected. This is advantageous over prior art systems, as it allows a user to test biological samples as the user is collecting them. This can prevent problems with contamination and degradation of biological samples due to transportation to a laboratory for testing, later discovery that not enough sample was taken, or later discovery that the collected biological sample is otherwise unsuitable for use. Allowing a user to test the biological sample in the field can save time, money, and resources. Testing in the field also provides the ability for rapid safety response if test results indicate a pathogen or toxin that may be harmful.

In the embodiment described below, the portable testing device is capable of testing biological samples with EnviroLogix's DNAble® chemistry, which employs an isothermal amplification process. This eliminates the need for thermocycling as a means to amplify nucleic acid products for endpoint detection. This allows a user to obtain data from the sample while the test is being run. In alternate embodiments, the portable testing device can be used to test biological samples with other isothermal amplification chemistries. The portable testing device displays this data on a screen on the device so that a user can view the results of the test in the field. Allowing a user to view the results of the test in the field is advantageous, as the user can then make an informed decision of whether additional tests are needed. In alternate embodiments, the portable testing device is also capable of incorporating a thermocycler to allow for the use of non-isothermal polymerase chain reaction (PCR) chemistries and result in qPCR and end-point analysis.

Optical Assembly 600

Figure 22A:
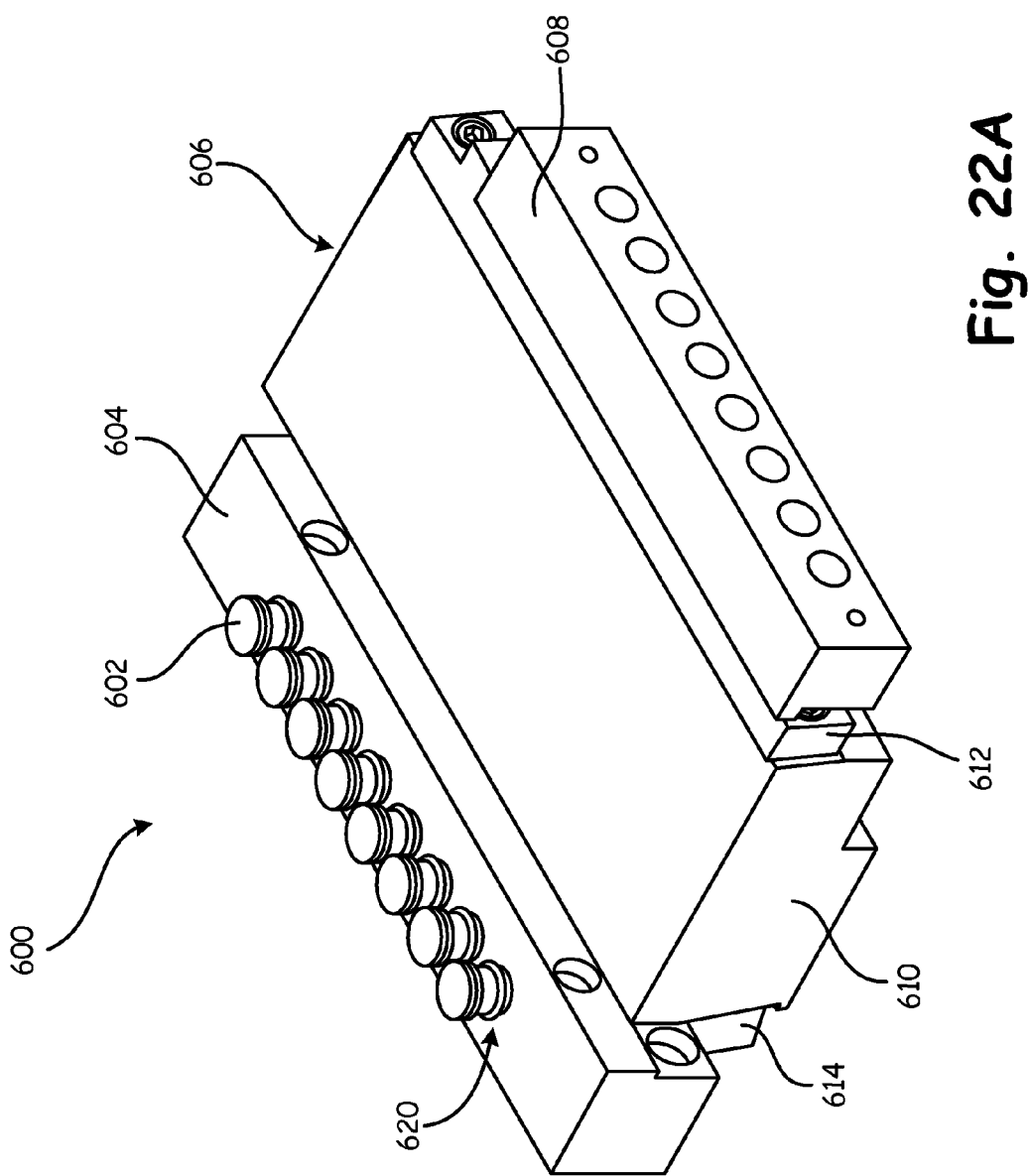
FIG. 22A is a perspective view of an optical assembly.
Figure 22B:
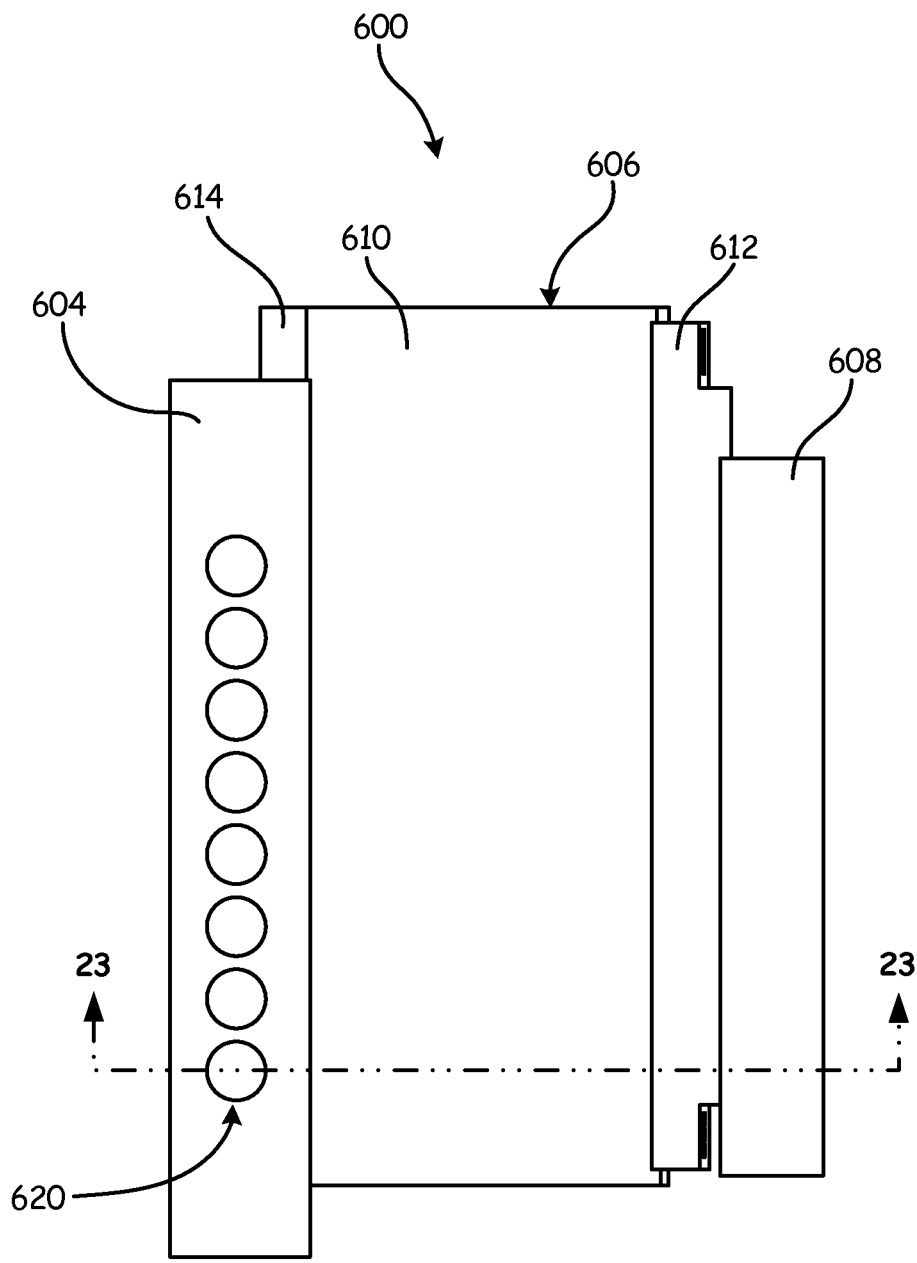
FIG. 22B is a top view of the optical assembly.

FIG. 22A is a perspective view of optical assembly 600. FIG. 22B is a top view of optical assembly 600. Optical assembly 600 includes tube array 602, sample block 604, movable housing 606, and stationary housing 608. Sample block 604 includes wells 620. Movable housing 606 includes body portion 610, detection portion 612, and excitation portion 614.

Sample block 604, movable housing 606, and stationary housing 608 form the body of optical assembly 600. Optical assembly 600 is also capable of receiving tube array 602 in sample block 604. Sample block 604 has a plurality of wells 620 located in a top side of sample block 604 that are configured to receive tube array 602 in the embodiment shown. In alternate embodiments, wells 620 can be configured to receive a card or any other suitable sample holder. Sample block 604 contains a heating component to heat the biological material in tube array 602.

Movable housing 606 includes body portion 610, detection portion 612, and excitation portion 614. Body portion 610 has a rectangular body shape. Sample block 604 is positioned on a first side of body portion 610. A first side of detection portion 612 is attached to a second side of body portion 610. Stationary housing 608 is positioned on a second side of detection portion 612. Detection portion 612 is capable of holding emission filters. Stationary housing 608 is capable of holding photodetectors to detect emissions from the biological sample in optical assembly 600. Excitation portion 614 is attached to the first side of body portion 206 below sample block 604. Excitation portion 614 is capable of holding light-emitting diodes and excitation filters to excite the biological samples in optical assembly 600. Body portion 610, detection portion 612, stationary housing 608, and excitation portion 614 all have a plurality of paths running through them so radiation can travel through movable housing 606 and into the biological samples in sample block 604.

Movable housing 606 includes a plurality of detection modules that can excite and detect biological materials at different radiation wavelengths. This allows optical assembly 600 to be compatible with a number of different fluorescent dyes that are used during testing of biological samples. Each fluorescent dye is excited and detected at a different radiation wavelength. In order to ensure that each well 620 in sample block 604 is read with each detection module, movable housing 606 is capable of moving. Movable housing 606 will move between a first position, a second position, and a third position in the embodiment shown, but can move between any number of positions in alternate embodiments. Sample block 604 and stationary housing 608 are stationary parts and movable housing 606 will slide between sample block 604 and stationary housing 608. As movable housing 606 moves, different detection modules will be aligned with different wells 620. This will allow each well 620 to be read with different detection modules. Movable housing 606 can be moved with an actuator or other suitable means.

Providing movable housing 606 in optical assembly 600 is advantageous, as the ability of movable housing 606 to move allows optical assembly 600 to test a plurality of radiation wavelengths. Optical assembly 600 is designed to be used in a portable testing device. A portable testing device need to be designed as compact as possible, so that it can be easily transported and used in the field. Without a moving optical assembly 600, more space would be required for placement of multiple detection modules that can read at different radiation wavelengths. Because movable housing 606 moves in optical assembly 600, the different detection modules can be easily repositioned to read from each of wells 620 in sample block 604. This saves significant space in the portable testing device, as the number of detection modules needed to test each of wells 620 is greatly reduced.

Figure 23:
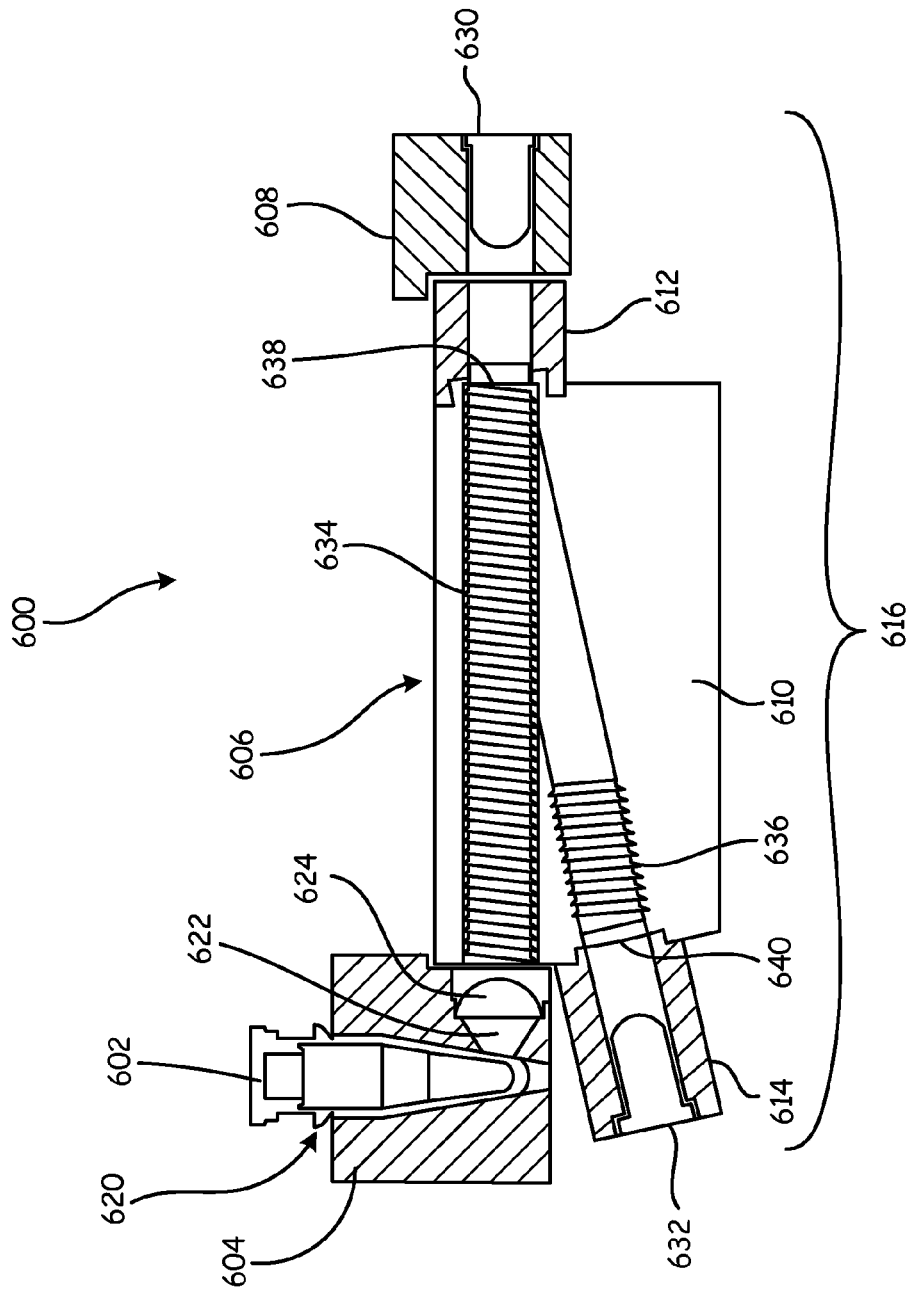
FIG. 23 is a cross-sectional side view of the optical assembly taken along line 23-23 of FIG. 22B.

FIG. 23 is a cross-sectional side view of optical assembly 600 taken along line 23-23 of FIG. 22B. Optical assembly 600 includes tube array 602, sample block 604, movable housing 606, stationary housing 608, and detection modules 616. Sample block 604 includes wells 620, apertures 622, and lenses 624. Movable housing 606 includes body portion 610, detection portion 612, and excitation portion 614. Each detection module 616 includes light-emitting diode 632, first path 634, second path 636, emission filter 638, and excitation filter 640. Stationary housing 608 includes photodetector 630.

Sample block 604 and movable housing 606 form the body of optical assembly 600. Sample block 604 includes a plurality of wells 620 that are configured to receive tube array 602. Tube array 602 includes a plurality of tubes, where each tube contains a biological sample that is to be tested. Sample block 604 further includes a plurality of apertures 622 that extend from a first side of sample block 604 to wells 620. Each well 620 will have a corresponding aperture 622. Lenses 624 can also be positioned in apertures 622 between the first side of sample block 604 and wells 620. Lenses 624 can direct radiation in optical assembly 600 into wells 620 and sample tubes 202.

Movable housing 606 is capable of moving and can be situated in three different positions relative to sample block 604. Movable housing 606 includes a plurality of detection modules 616 that are aligned with wells 620 in sample block 604. Each detection module 616 is capable of exciting and detecting emissions from a biological sample in one of wells 620. Each detection module 616 includes one light-emitting diode 632, one first path 634, one second path 636, one emission filter 638, and one excitation filter 640.

Stationary housing 608 is positioned on a second side of movable housing 606. Stationary housing 608 includes photodetector 630. As movable housing 606 moves between three different positions, stationary housing 608 will remain stationary. This will align each of the different photodetector 630 in stationary housing 608 with a different detection module 616.

Movable housing 606 includes body portion 610 that forms the base of movable housing 606. Detection portion 612 is attached to a first side of body portion 610 of movable housing 606, and excitation portion 614 is attached to a second side of body portion 610 of movable housing 606. First path 634 extends horizontally through body portion 610 of movable housing 606 from detection portion 612 to sample block 604. Second path 636 extends at an angle through body portion 610 of movable housing 606 from excitation portion 614 to detection portion 612. First path 634 and second path 636 converge at detection portion 612. First path 634 and second path 636 are both capable of transmitting radiation through movable housing 606. First path 634 and second path 636 are shown as threaded paths in the embodiment shown, but can be smooth paths in alternate embodiments. Threading first path 634 and second path 636 can prevent stray radiation from traveling through movable housing 606, as it will be reflected when it diverges from the main course.

Detection portion 612 of movable housing 606 has a plurality of apertures that are capable of receiving emission filters 638. Emission filters 638 are positioned in the apertures in detection portion 612 between a first side of detection portion 612 and a second side of detection portion 612.

Stationary housing 608 has a plurality of apertures that are capable of receiving photodetector 630. Photodetector 630 are positioned on a second side of stationary housing 608 and extend a distance into stationary housing 608.

Excitation portion 614 of movable housing 606 has a plurality of apertures that are capable of receiving light-emitting diodes 632 and excitation filters 640. Light-emitting diodes 632 are positioned on a first side of excitation portion 614 and extend a distance into excitation portion 614. Excitation filters 640 are positioned in excitation portion 614 between light-emitting diodes 632 and a second side of excitation portion 614.

Each detection module 616 works as follows. To excite a biological sample positioned in well 620, radiation is emitted from light-emitting diode 632. The radiation that is emitted from light-emitting diode 632 will be filtered by excitation filter 640. The filtered radiation will then travel from a first end to a second end of second path 636. At the second end of second path 636, the radiation will be reflected off of emission filter 638. The reflected radiation will be directed into a first end of first path 634. The radiation will then travel from the first end to a second end of first path 634. At the second end of first path 634, the radiation will travel through aperture 622 and lens 624 in sample block 604 and into wells 620. Once in wells 620, the radiation can excite the biological sample in one of the tubes of tube array 602.

After the biological sample is excited it will emit radiation corresponding with fluorescent labels that are mixed with the biological sample. The radiation emitted from the biological sample can then travel from well 620 through lens 624 and aperture 622 into second end of first path 634. The radiation will then travel from second end to first end of first path 634. At the first end of first path 634, the radiation will reach and pass through emission filter 638. Radiation that is filtered through emission filter 638 can then travel through the aperture in detection portion 612 and into the aperture in stationary housing 608. Photodetector 630 positioned in stationary housing 608 can then receive the radiation.

Different fluorescent dyes can be used to test biological samples during nucleic acid amplification. To provide an instrument that is capable of reading different fluorescent dyes, movable housing 606 can move in relation to sample block 604 so that a different detection module 616 is aligned with each well 620, depending on what fluorescent dyes have been added to the biological sample in each well 620. If multiple fluorescent dyes are added to the biological sample in each well 620, movable housing 606 can move between positions to ensure that the different fluorescence of each well 620 are being read.

Optical assembly 600 is advantageous for use in a portable testing device, as optical assembly 600 can read fluorescence at a plurality of different radiation wavelengths with a compact design. A suitable portable testing device needs to be compact so that it can be easily transported and used in the field. To design a compact portable testing device, optical assembly 600 also needs to be compact. In previous optical assemblies, being compact equated to only being able to test at one or two different radiation wavelengths. Optical assembly 600 eliminates this issue, as optical assembly 600 can move to position different detection modules 616 with different wells 620 in sample block 604. This allows more than two radiation wavelengths to be tested without sacrificing compactness of optical assembly 600. Optical assembly 600 is advantageous for this reason and is suitable for use in portable testing devices.

Figure 24A:
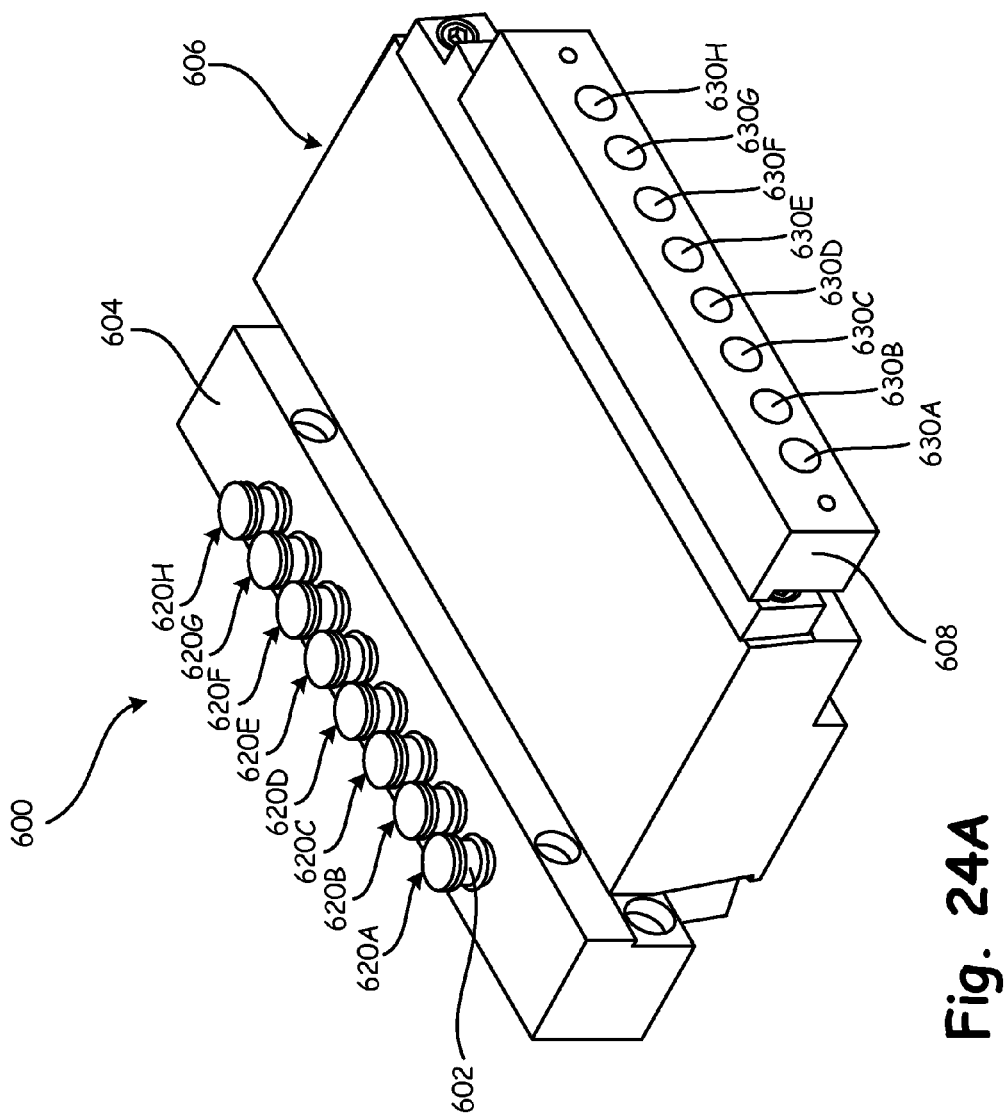
FIG. 24A is a perspective view of the optical assembly in a first position.
Figure 24B:
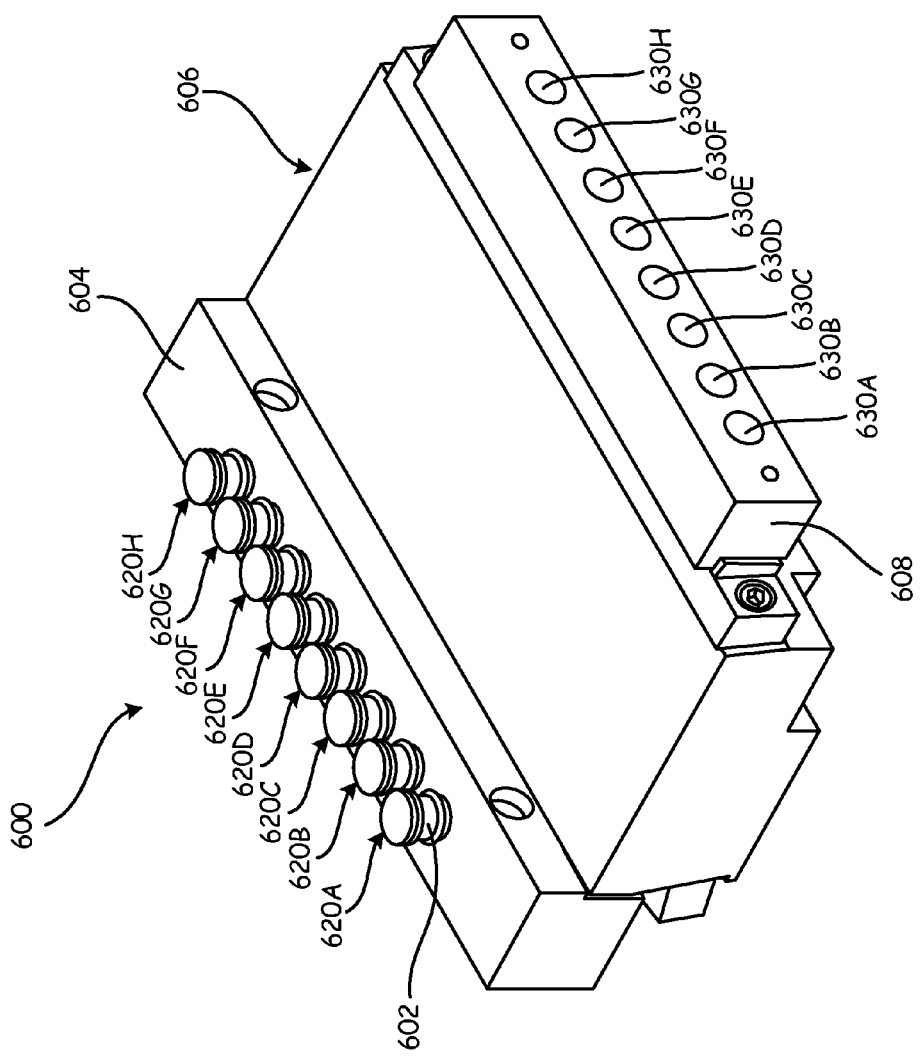
FIG. 24B is a perspective view of the optical assembly in a second position.
Figure 24C:
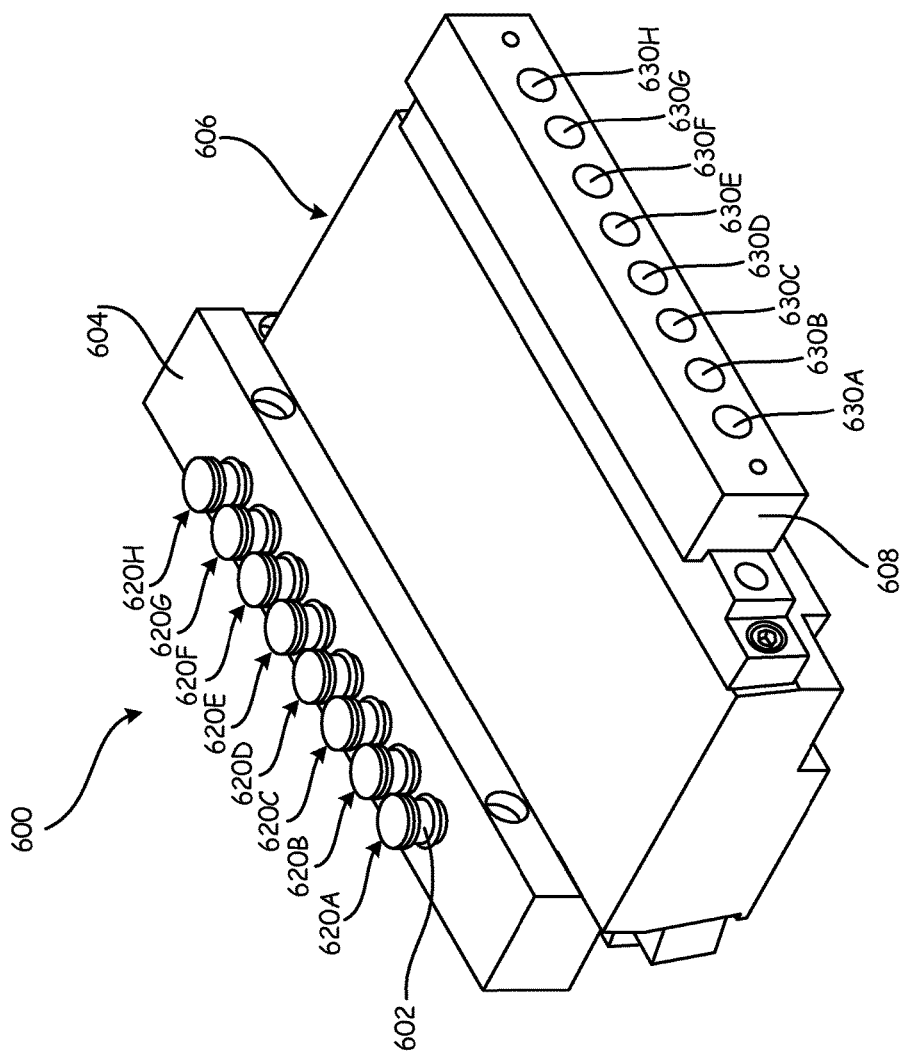
FIG. 24C is a perspective view of the optical assembly in a third position.

FIG. 24A is a perspective view of optical assembly 600 in a first position. FIG. 24B is a perspective view of optical assembly 600 in a second position. FIG. 24C is a perspective view of optical assembly 600 in a third position. Optical assembly 600 includes tube array 602, sample block 604, movable housing 606, stationary housing 608, and detection modules 616 (including detection module 616A, detection module 616B, detection module 616C, detection module 616D, detection module 616E, detection module 616F, detection module 616G, detection module 616H, detection module 616I, and detection module 616J). Sample block 604 includes wells 620 (including well 620A, well 620B, well 620C, well 620D, well 620E, well 620F, well 620G, and well 620H). Stationary housing 608 includes photodetector 630 (including photodetector 630A, photodetector 630B, photodetector 630C, photodetector 630D, photodetector 630E, photodetector 630F, photodetector 630G, and photodetector 630H).

Sample block 604, movable housing 606, and stationary housing 608 form the body of optical assembly 600. Sample block 604 is a stationary part with a plurality of wells 620. Tube array 602 can be positioned in wells 620. Tube array 602 includes a plurality of individual tubes that each contain a biological sample and a reaction mixture with fluorescent dyes. Each tube in tube array 602 is positioned in one well 620. Stationary housing 608 is also a stationary part with a plurality of photodetector 630. One photodetector 630 in stationary housing 608 is aligned with one well 620 in sample block 604. Photodetector 630A is aligned with well 620A; photodetector 630B is aligned with well 620B; photodetector 630C is aligned with well 620C; photodetector 630D is aligned with well 620D; photodetector 630E is aligned with well 620E; photodetector 630F is aligned with well 620F; photodetector 630G is aligned with well 620G; and photodetector 630H is aligned with well 620H.

In the embodiment shown, movable housing 606 is a moving part that can move between a first position, a second position, and a third position with respect to sample block 604 and stationary housing 608. In alternate embodiments, movable housing 606 can move between any number of positions. Movable housing 606 includes a plurality of detection modules 616. As movable housing 606 moves, each detection module 616 will be aligned with one well 620 and one photodetector 630. Each detection module 616 includes a light-emitting diode to excite a biological sample. To detect a plurality of different fluorescent dyes, the light-emitting diodes that are positioned in each detection module can vary. The embodiment shown in FIGS. 24A-24C includes eight wells 620, eight photodetector 630, and ten detection modules 616. This allows three different fluorescent dyes to be tested, as movable housing 606 can be positioned in three different positions. In each different position, each well 620 and photodetector 630 will be aligned with a different detection module 616 to read different fluorescent dyes from each well 620.

In the embodiment shown in FIGS. 24A-24C, optical assembly 600 can detect a first fluorescent dye, a second fluorescent dye, and a third fluorescent dye. Detection module 616A is configured to detect the first fluorescent dye; detection module 616B is configured to detect the second fluorescent dye; detection module 616C is configured to detect the third fluorescent dye; detection module 616D is configured to detect the first fluorescent dye; detection module 616E is configured to detect the second fluorescent dye; detection module 616F is configured to detect the third fluorescent dye; detection module 616G is configured to detect the first fluorescent dye; detection module 616H is configured to detect the second fluorescent dye; detection module 616I is configured to detect the third fluorescent dye; and detection module 616J is configured to detect the first fluorescent dye. As movable housing 606 moves between a first position, a second position, and a third position, each well 620 will be excited and detected for each of the first fluorescent dye, the second fluorescent dye, and the third fluorescent dye.

In a first position, well 620A is aligned with detection module 616A to detect the first fluorescent dye; well 620B is aligned with detection module 616B to detect the second fluorescent dye; well 620C is aligned with detection module 616C to detect the third fluorescent dye; well 620D is aligned with detection module 616D to detect the first fluorescent dye; well 620E is aligned with detection module 616E to detect the second fluorescent dye; well 620F is aligned with detection module 616F to detect the third fluorescent dye; well 620G is aligned with detection module 616G to detect the first fluorescent dye; and well 620H is aligned with detection module 616H to detect the second fluorescent dye.

In a second position, well 620A is aligned with detection module 616B to detect the second fluorescent dye; well 620B is aligned with detection module 616C to detect the third fluorescent dye; well 620C is aligned with detection module 616D to detect the first fluorescent dye; well 620D is aligned with detection module 616E to detect the second fluorescent dye; well 620E is aligned with detection module 616F to detect the third fluorescent dye; well 620F is aligned with detection module 616G to detect the first fluorescent dye; well 620G is aligned with detection module 616H to detect the second fluorescent dye; and well 620H is aligned with detection module 616I to detect the third fluorescent dye.

In a third position, well 620A is aligned with detection module 616C to detect the third fluorescent dye; well 620B is aligned with detection module 616D to detect the first fluorescent dye; well 620C is aligned with detection module 616E to detect the second fluorescent dye; well 620D is aligned with detection module 616F to detect the third fluorescent dye; well 620E is aligned with detection module 616G to detect the first fluorescent dye; well 620F is aligned with detection module 616H to detect the second fluorescent dye; well 620G is aligned with detection module 616I to detect the third fluorescent dye; and well 620H is aligned with detection module 616J to detect the first fluorescent dye.

As seen from this, as movable housing 606 moves between a first position, a second position, and a third position, each well 620 will be excited and detected for each of the first fluorescent dye, the second fluorescent dye, and the third fluorescent dye. Movable housing 606 can be repositioned any number of times during a test to repeat excitation and detection of each of wells 620 until satisfactory test results are obtained. Further, in alternate embodiments, movable housing 606 can include more detection modules to read additional fluorescent dyes. This will increase the number of positions that movable housing 606 will move to so that each well 620 is excited and detected at each different fluorescence wavelength.

Optical assembly 600 is advantageous, as it can excite and detect at a plurality of different radiation wavelengths with a compact and streamlined design. This makes optical assembly 600 suitable for use in a portable testing device, as the compactness of optical assembly 600 will reduce the overall size of a portable testing device. Further, optical assembly 600 allows a portable testing device to test at a number of radiation wavelengths that was not feasible with previous designs.

Optical Assembly 700

Figure 25:
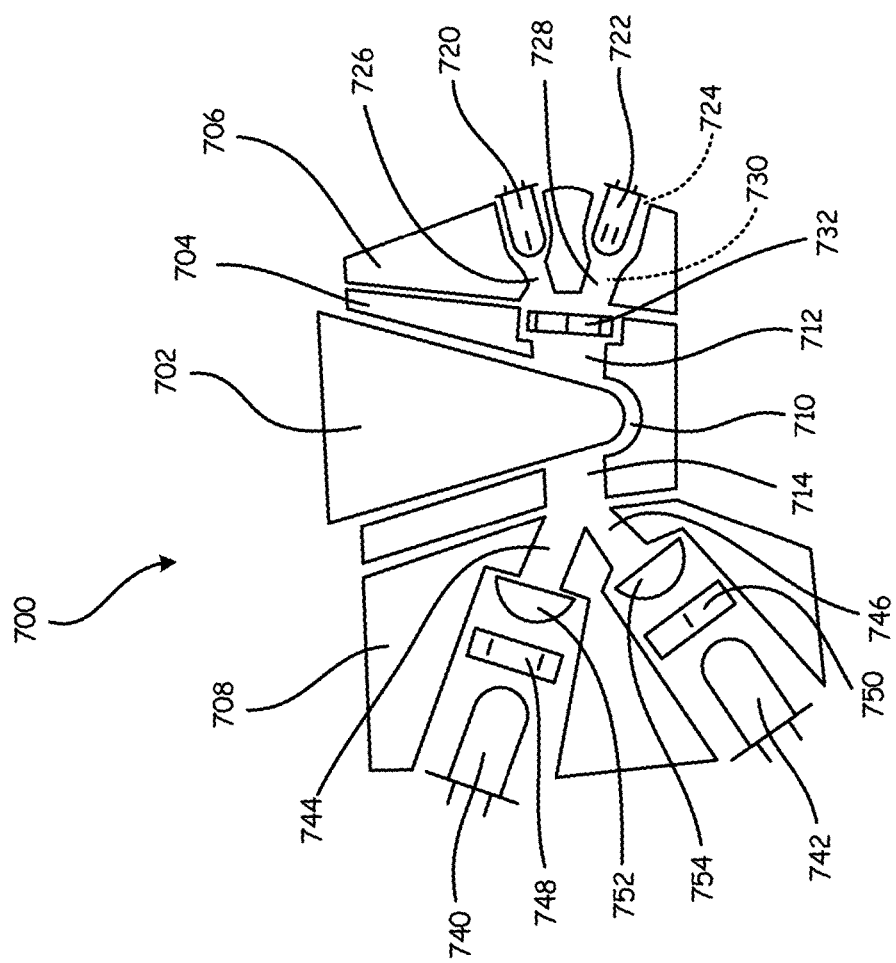
FIG. 25 is a cross-sectional side view of an optical assembly.

FIG. 25 is a cross-sectional side view of optical assembly 700. Optical assembly 700 includes tube array 702, sample block 704, first housing 706, second housing 708, well 710, first aperture 712, second aperture 714, first light-emitting diode 720, second light-emitting diode 722, third light-emitting diode 724, first excitation path 726, second excitation path 728, third excitation path 730, excitation filter 732, first photodetector 740, second photodetector 742, first detection path 744, second detection path 746, first emission filter 748, second emission filter 750, first lens 752, and second lens 754.

Sample block 704, first housing 706, and second housing 708 form the body of optical assembly 700. Sample block 704 includes a plurality of wells 710. Wells 710 are capable of receiving tube array 702. Sample block 704 also includes a heating component to heat a biological sample in tube array 702. Sample block 704 includes first apertures 712 that extend from a first side of sample block 704 into wells 710. Sample block 704 also includes second apertures 714 that extend from a second side of sample block 704 into wells 710. First housing 706 is located on a first side of sample block 704 and second housing 708 is located on a second side of sample block 704.

First housing 706 and second housing 708 are both capable of holding light-emitting diodes and photodetectors to excite and detect emissions from the biological samples in tube array 702. In the embodiment shown in FIG. 8, light-emitting diodes are located in first housing 706 and photodetectors are located in second housing 708. In alternate embodiments, photodetectors can be located in first housing 706 and light-emitting diodes can be located in second housing 708, or a mix of light-emitting diodes and photodetectors can be alternated in both first housing 706 and second housing 708. In each arrangement, one light-emitting diode is positioned on one side of well 710 and one photodetector is positioned on the opposite side of well 710.

As seen in FIG. 25, first light-emitting diode 720, second light-emitting diodes 722, and third light-emitting diode 724 are positioned in first housing 706. First light-emitting diode 720, second light-emitting diodes 722, and third light-emitting diode 724 are located in a triangular configuration. Each light-emitting diode is capable of exciting a different fluorescent dye in the biological sample by emitting radiation at a different wavelength. First light-emitting diode 720 excites a first fluorescent dye, second light-emitting diodes 722 excites a second fluorescent dye, and third light-emitting diode 724 excites a third fluorescent dye in the embodiment shown. First light-emitting diode 720 is positioned in first path 726 that runs from first light-emitting diode 720 to sample block 704. Second light-emitting diodes 722 is positioned in second path 728 that runs from second light-emitting diodes 722 to sample block 704. Third light-emitting diode 724 is positioned in third path 730 that runs from third-light emitting diode 724 to sample block 704. Excitation filter 732 is positioned in sample block 704 to filter light from first light-emitting diode 720, second light-emitting diodes 722, and third light-emitting diode 724. Excitation filter 732 is a triple bandpass filter that is capable of filtering radiation at wavelengths for the first fluorescent dye, the second fluorescent dye, and the third fluorescent dye. In alternate embodiments, separate excitation filters can be used for each light-emitting diode.

First photodetector 740 and second photodetector 742 are positioned in second housing 708. First photodetector 740 is capable of detecting both the first fluorescent dye and the third fluorescent dye. Second photodetector 742 is capable of detection the second fluorescent dye. First photodetector 740 is positioned in first path 744 that extends from first photodetector 740 to sample block 704. Second photodetector 742 is positioned in second path 346 that extends from second photodetector 742 to sample block 704. First emission filter 748 is positioned in first path 744 between first photodetector 740 and sample block 704. First emission filter 748 is a dual bandpass filter that is capable of filtering radiation at wavelengths for the first fluorescent dye and the third fluorescent dye. Second emission filter 750 is positioned in second path 746 between second photodetector 742 and sample block 704. Second emission filter 750 is a single bandpass filter that is capable of filtering radiation at wavelengths for the second fluorescent dye. Also positioned in first path 744 is first lens 752. Also positioned in second path 746 is second lens 754. First lens 752 and second lens 754 will direct emitted radiation from the biological sample in tube 702 into first photodetector 740 and second photodetector 742, respectively.

Optical assembly 700 is designed so that biological samples can be excited and detected at three different radiation wavelengths. Detecting and exciting at three different radiation wavelengths is advantageous, as each biological sample can be tested for each of the first fluorescent dye, the second fluorescent dye, and the third fluorescent dye. Using first photodetectors 740 and second photodetectors 742 is also advantageous, as it will limit crosstalk between detection channels to improve detection performance. The design of optical assembly 700 with clustering of light-emitting diodes and photodetectors is also advantageous, as it allows optical assembly 700 to be designed with a compact configuration. Being compact allows optical assembly 700 to be used in a portable testing device. Portable testing devices need to be compact so that they can be easily transported and used in the field.

FIG. 26A is a side view of a first side of optical assembly 700 according to a first configuration. FIG. 26B is a side view of a second side of optical assembly 700 according to the first configuration. Optical assembly 700 includes first housing 706, second housing 708, first light-emitting diodes 720 (including first light-emitting diode 720A, first light-emitting diode 720B, first light-emitting diode 720C, first light-emitting diode 720D, first light-emitting diode 720E, first light-emitting diode 720F, first light-emitting diode 720G, and first light-emitting diode 720H), second light-emitting diodes 722 (including second light-emitting diodes 722A, second light-emitting diodes 722B, second light-emitting diodes 722C, second light-emitting diodes 722D, second light-emitting diodes 722E, second light-emitting diodes 722F, second light-emitting diodes 722G, and second light-emitting diodes 722H), third light-emitting diodes 724

(including third light-emitting diode 724A, third light-emitting diode 724B, third light-emitting diode 724C, third light-emitting diode 724D, third light-emitting diode 724E, third light-emitting diode 724F, third light-emitting diode 724G, and third light-emitting diode 724H), first photodetectors 740 (including first photodetector 740A, first photodetector 740B, first photodetector 740C, first photodetector 740D, first photodetector 740E, first photodetector 740F, first photodetector 740G, and first photodetector 740H), and second photodetectors 742 (including second photodetector 742A, second photodetector 742B, second photodetector 742C, second photodetector 742D, second photodetector 742E, second photodetector 742F, second photodetector 742G, and second photodetector 742H).

First light-emitting diodes 720, second light-emitting diodes 722, and third light-emitting diodes 724 are positioned in first housing 706. First light-emitting diodes 720 are capable of exciting a first fluorescent dye. Second light-emitting diodes 722 are capable of exciting a second fluorescent dye. Third light-emitting diodes 724 are capable of exciting a third fluorescent dye. First light-emitting diodes 720, second light-emitting diodes 722, and third light-emitting diodes 724 are arranged in a triangular configuration in first housing 706. As an exemplary explanation, this configuration can be seen with first light-emitting diode 720A, second light-emitting diodes 722A, and third light-emitting diode 724A which are arranged in a triangular configuration. This triangular configuration is repeated in an alternating fashion throughout first housing 706 to provide a compact configuration.

First photodetectors 740 and second photodetectors 742 are positioned in second housing 708. First photodetectors 740 are capable of detecting emissions from the first fluorescent dye and the third fluorescent dye. Second photodetectors 742 are capable of detecting emissions from the second fluorescent dye. First photodetectors 740 and second photodetectors 742 are stacked one on top of the other in second housing 708. As an exemplary explanation, this configuration can be seen with first photodetector 740A and second photodetector 742A which are stacked one on top of the other. This stacked configuration is repeated throughout second housing 708.

In the configuration seen in FIGS. 26A-26B, light-emitting diodes are positioned in first housing 706 on a first side of a sample block and photodetectors are positioned in second housing 708 on a second side of a sample block. First light-emitting diodes 720 and third light-emitting diodes 724 are located opposite of first photodetectors 740. Second light-emitting diodes 722 are located opposite of second photodetectors 742. When first light-emitting diodes 720 or third light-emitting diodes 724 are activated, first photodetectors 740 will read emissions from the biological sample. When second light-emitting diodes 722 are activated, second photodetectors 742 will read emissions from the biological sample.

The first configuration of light-emitting diodes and photodetectors seen in FIGS. 26A-26B is advantageous, as it provides a compact arrangement that is capable of exciting and detecting at three different radiation wavelengths. This makes optical assembly 700 suitable for use in a portable testing device.

FIG. 27A is a side view of a first side of optical assembly 700 according to a second configuration. FIG. 27B is a side view of a second side of optical assembly 700 according to a second configuration. Optical assembly 700 includes first housing 706, second housing 708, first light-emitting diodes 720 (including first light-emitting diode 720A, first light-emitting diode 720B, first light-emitting diode 720C, first light-emitting diode 720D, first light-emitting diode 720E, first light-emitting diode 720F, first light-emitting diode 720G, and first light-emitting diode 720H), second light-emitting diodes 722 (including second light-emitting diodes 722A, second light-emitting diodes 722B, second light-emitting diodes 722C, second light-emitting diodes 722D, second light-emitting diodes 722E, second light-emitting diodes 722F, second light-emitting diodes 722G, and second light-emitting diodes 722H), third light-emitting diodes 724 (including third light-emitting diode 724A, third light-emitting diode 724B, third light-emitting diode 724C, third light-emitting diode 724D, third light-emitting diode 724E, third light-emitting diode 724F, third light-emitting diode 724G, and third light-emitting diode 724H), first photodetectors 740 (including first photodetector 740A, first photodetector 740B, first photodetector 740C, first photodetector 740D, first photodetector 740E, first photodetector 740F, first photodetector 740G, and first photodetector 740H), and second photodetectors 742 (including second photodetector 742A, second photodetector 742B, second photodetector 742C, second photodetector 742D, second photodetector 742E, second photodetector 742F, second photodetector 742G, and second photodetector 742H).

First light-emitting diodes 720, second light-emitting diodes 722, third light-emitting diodes 724, first photodetectors 740, and second photodetectors 742 are positioned in alternating patterns in first housing 706 and second housing 708. First light-emitting diodes 720 are capable of exciting a first fluorescent dye. Second light-emitting diodes 722 are capable of exciting a second fluorescent dye. Third light-emitting diodes 724 are capable of exciting a third fluorescent dye. First photodetectors 740 are capable of detecting emissions from the first fluorescent dye and the third fluorescent dye. Second photodetectors 742 are capable of detecting emissions from the second fluorescent dye.

First light-emitting diodes 720, second light-emitting diodes 722, and third light-emitting diodes 724 are arranged in a triangular configuration in both first housing 706 and second housing 708. As an exemplary explanation, this configuration can be seen with first light-emitting diode 720A, second light-emitting diodes 722A, and third light-emitting diode 724A which are arranged in a triangular configuration. First photodetectors 740 and second photodetectors 742 are arranged in a diagonal configuration in both first housing 706 and second housing 708. As an exemplary explanation, this configuration can be seen with first photodetector 740B and second photodetector 742B which are arranged in a diagonal configuration. The triangular configuration of the light-emitting diodes is alternated with the diagonal configuration of the photodetectors throughout both first housing 706 and second housing 708.

In the configuration seen in FIGS. 27A-27B, first light-emitting diodes 720 and third light-emitting diodes 724 are located opposite of first photodetectors 740. Second light-emitting diodes 722 are located opposite of second photodetectors 742. When first light-emitting diodes 720 or third light-emitting diodes 724 are activated, first photodetectors 740 will read emissions from the biological sample. When second light-emitting diodes 722 are activated, second photodetectors 742 will read emission from the biological sample.

The second configuration of light-emitting diodes and photodetectors seen in FIGS. 27A-27B is advantageous, as it provides a compact arrangement that is capable of exciting and detecting at three different radiation wavelengths. This makes optical assembly 700 suitable for use in a portable testing device.

Optical Assembly 800

Figure 28A:
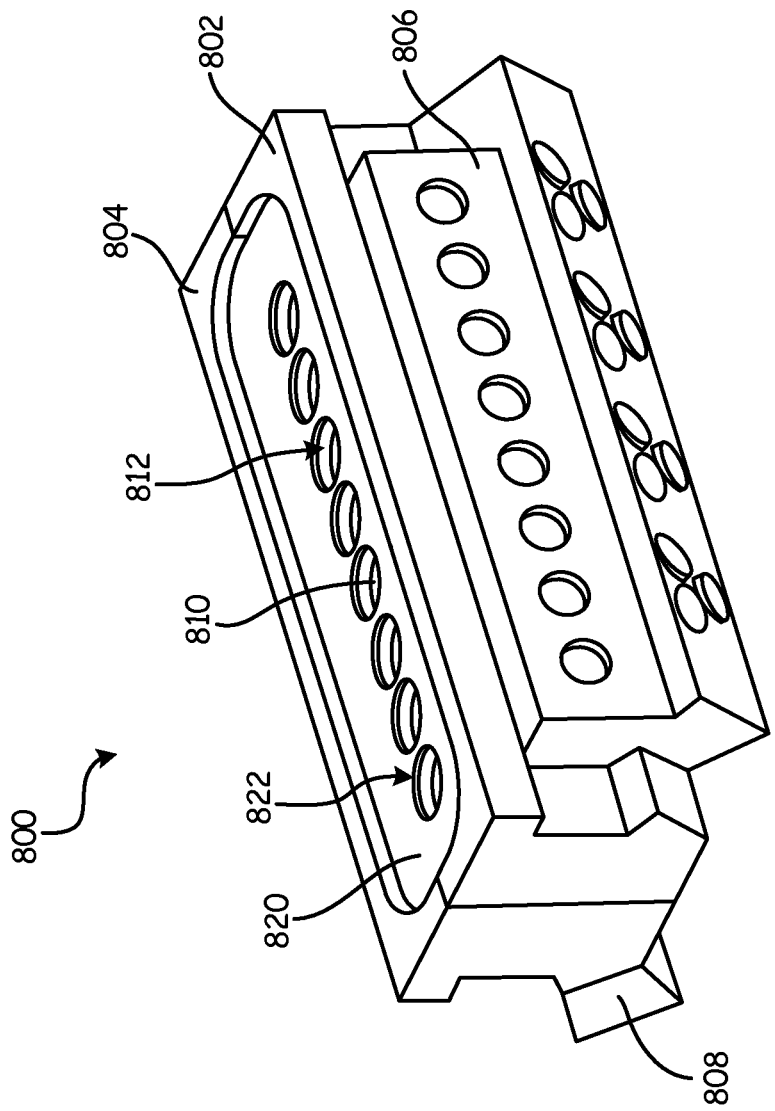
FIG. 28A is a perspective view of an optical assembly.
Figure 28B:
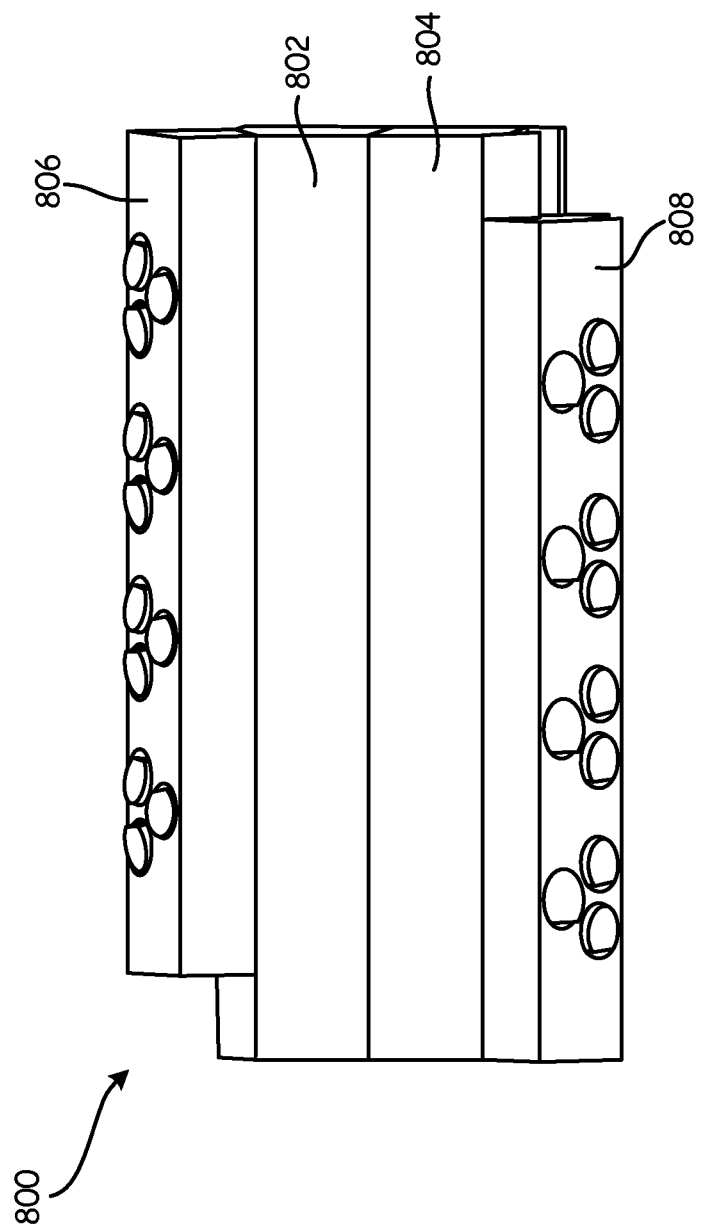
FIG. 28B is a bottom view of the optical assembly.

FIG. 28A is a perspective view of optical assembly 800. FIG. 28B is a bottom view of optical assembly 800.

Optical assembly 800 includes first housing portion 802, second housing portion 804, first optical housing 806, second optical housing 808, heat block 810, and plate 820. Heat block 810 includes wells 812. Plate 820 includes apertures 822.

Optical assembly 800 is capable of receiving an array of tubes for testing. Heat block 810 receives the array of tubes in wells 812. Wells 812 are positioned on a top side of heat block 810 and each well 812 is configured to receive one tube in the array of tubes. Heat block 810 forms a base of optical assembly 800 and heats a biological sample that is placed in each of the tubes in the array of tubes. In alternate embodiments, heat block 810 can be a sample block that is capable of receiving an array of tubes and the tubes can be heated using a different means.

Plate 820 is also included in optical assembly 800 and is placed over the top side of heat block 810. Plate 820 includes a plurality of apertures 822 that run from a top side of plate 820 to a bottom side of plate 820. Each aperture 822 in plate 820 can be aligned with one well 812 in heat block 810. When an array of tubes is placed in heat block 810, one tube can pass through each aperture 822 of plate 820 before being positioned in well 812. Plate 820 is made out of an opaque material in the embodiment shown. This prevents radiation from escaping out of optical assembly 800 and prevents ambient light from entering into optical assembly 800. Plate 820 also acts as an insulator to keep heat from heat block 810 in optical assembly 800.

A housing portion is also positioned on each side of heat block 810. First housing portion 802 is positioned on a first side of heat block 810 and second housing portion 804 is positioned on a second side of heat block 810. First housing portion 802 and second housing portion 804 join one another around heat block 810. First housing portion 802 and second housing portion 804 can be connected to one another with any suitable means.

Optical assembly 800 also includes first optical housing 806 and second optical housing 808. First optical housing 806 is connected to first housing portion 802 on the first side of heat block 810. First optical housing 806 can be connected to first housing portion 802 with any suitable means. First optical housing 806 is capable of holding a first set of light-emitting diodes and a first set of photodetectors. Second optical housing 808 is connected to second housing portion 804 on the second side of heat block 810. Second optical housing 808 can be connected to second housing portion 804 with any suitable means. Second optical housing 808 is capable of holding a second set of light-emitting diodes and a second set of photodetectors.

First housing portion 802, second housing portion 804, first optical housing 806, and second optical housing 808 are formed out of opaque materials. This allows radiation that is passed through optical assembly 800 to be retained in passages that runs through first housing portion 802, second housing portion 804, first optical housing 806, and second optical housing 808. Further, in alternate embodiments optical assembly 800 can include one housing portion on each side of heat block 810, can include one single housing piece, or any other suitable configuration.

Optical assembly 800 is advantageous, as it has a compact design that allows a set of light-emitting diodes and a set of photodetectors to be positioned on both sides of heat block 810. This allows more light-emitting diodes to be placed in each set of light-emitting diodes, increasing the overall capabilities of optical assembly 800. Light-emitting diodes can excite a biological sample at different radiation wavelengths. Thus, allowing more light-emitting diodes to be positioned in optical assembly 800 is advantageous, as optical assembly will be able to excite and detect emissions that correspond with different fluorescent dyes.

Figure 29A:
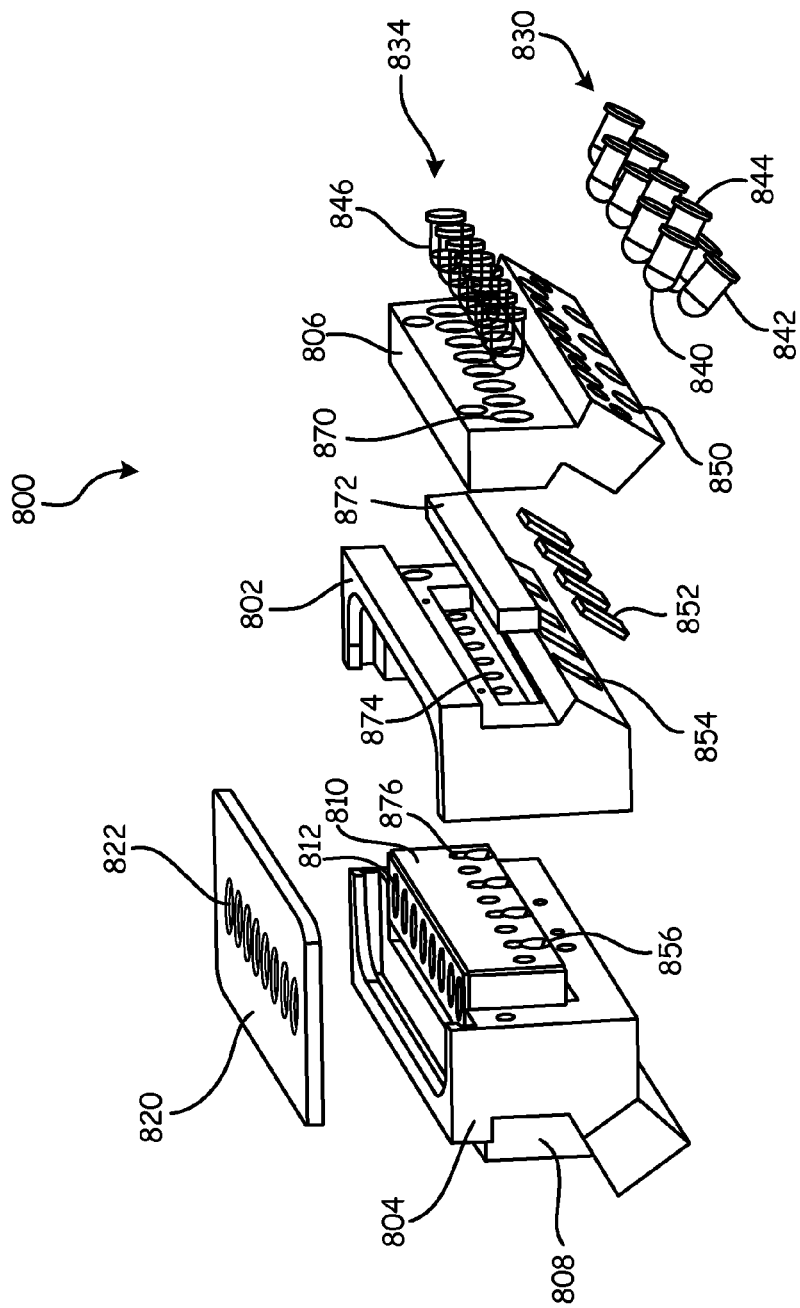
FIG. 29A is an exploded perspective view of a first side of the optical assembly.
Figure 29B:
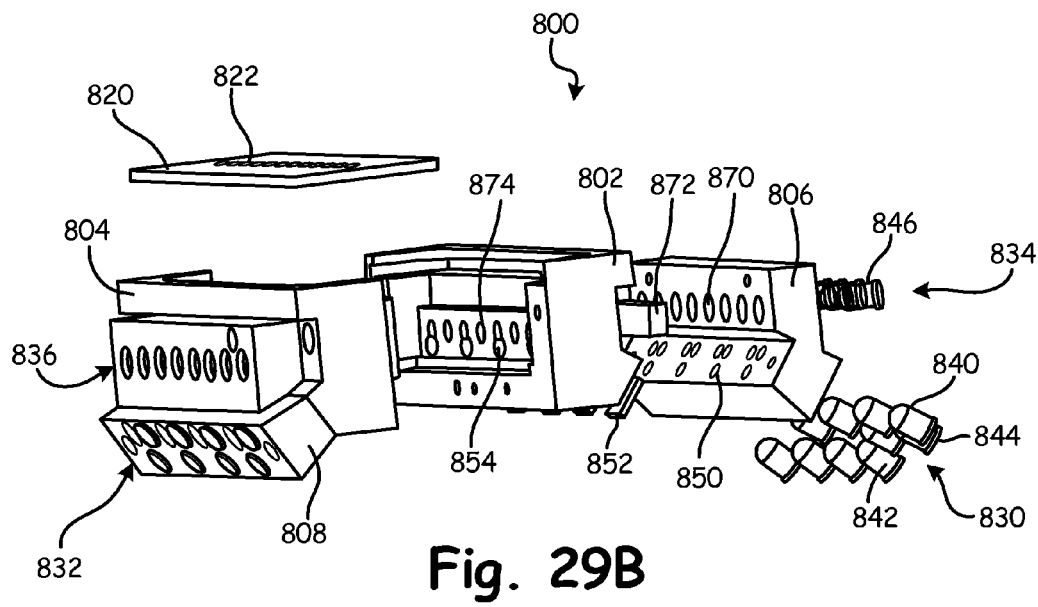
FIG. 29B is an exploded perspective view of the first side of the optical assembly.
Figure 29C:
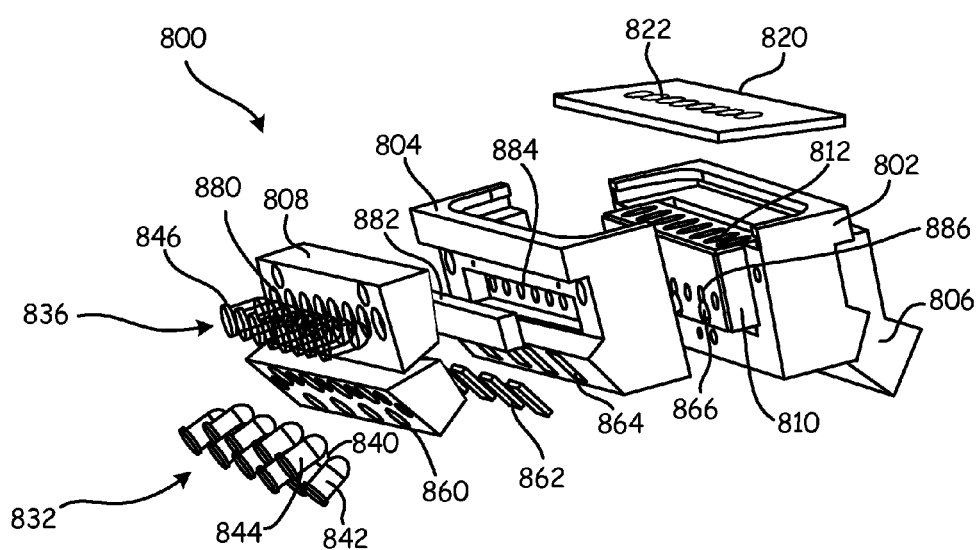
FIG. 29C is an exploded perspective view of a second side of the optical assembly.
Figure 29D:
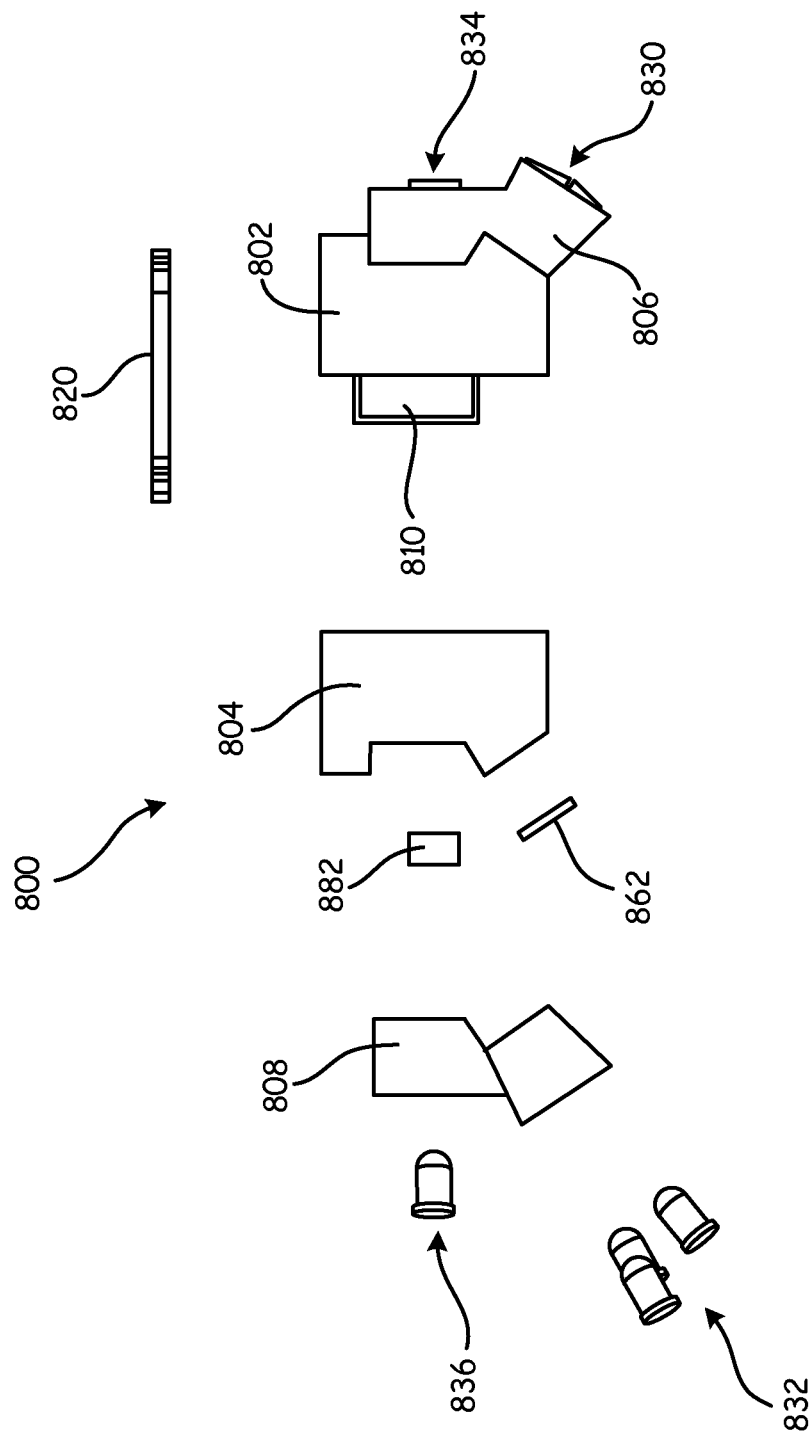
FIG. 29D is an exploded side view of the second side of the optical assembly.

FIG. 29A is an exploded perspective view of a first side of optical assembly 800. FIG. 29B is an exploded perspective view of the first side of optical assembly 800. FIG. 29C is an exploded perspective view of a second side of optical assembly 800. FIG. 29D is an exploded side view of the second side of optical assembly 800.

Optical assembly 800 includes first housing portion 802, second housing portion 804, first optical housing 806, second optical housing 808, heat block 810, plate 820, first light-emitting diode set 830, second light-emitting diode set 832, first photodetector set 834, second photodetector set 836, excitation filters 852, excitation filters 862, emission filter 872, and emission filter 882. Heat block 810 includes wells 812, passages 856, passages 866, passages 876, and passages 886. Plate 820 includes apertures 822. First housing portion 802 includes passages 854 and passages 874. Second housing portion 804 includes passages 864 and passages 884. First optical housing 806 includes passages 850 and passages 870. Second optical housing 808 includes passages 860 and passages 880. First light-emitting diode set 830 includes light-emitting diodes 840, light-emitting diodes 842, and light-emitting diodes 844. Second light-emitting diode set 832 includes light-emitting diodes 840, light-emitting diodes 842, and light-emitting diodes 844. First photodetector set 834 includes photodetectors 846. Second photodetector set 836 includes photodetectors 846.

Optical assembly 800 is capable of receiving an array of tubes for testing. Heat block 810 receives the array of tubes in wells 812. Wells 812 are positioned on a top side of heat block 810 and each well 812 is configured to receive one tube in the array of tubes. Heat block 810 forms a base of optical assembly 800 and heats a biological sample that is placed in each of the tubes in the array of tubes. Heat block 810 further includes passages 856, passages 866, passages 876, and passages 886. Passages 856 and passages 876 extend from a first side of heat block 810 to wells 812. Passages 866 and passages 886 extend from a second side of heat block 810 to wells 812. Passages 856, passages 866, passages 876, and passages 886 provide pathways through which radiation can travel through optical assembly 800.

Plate 820 is also included in optical assembly 800 and is placed over the top side of heat block 810. Plate 820 includes a plurality of apertures 822 that run from a top side of plate 820 to a bottom side of plate 820. Each aperture 822 in plate 820 can be aligned with one well 812 in heat block 810. When an array of tubes is placed in heat block 810, one tube can pass through each aperture 822 of plate 820 before being positioned in well 812.

A housing portion is also positioned on each side of heat block 810. First housing portion 802 is positioned on a first side of heat block 810 and second housing portion 804 is positioned on a second side of heat block 810. First housing portion 802 includes passages 854 and passages 874 that extend from a first side of first housing portion 802 to a second side of first housing portion 802. Second housing portion 804 includes passages 864 and passages 884 that extend from a first side of second housing portion 804 to a second side of second housing portion 804. Passages 854, passages 864, passages 874, and passages 884 provide pathways through which radiation can travel through optical assembly 800.

Optical assembly 800 further includes first optical housing 806 and second optical housing 808. First optical housing 806 is connected to first housing portion 802 on the first side of heat block 810. First optical housing 806 can be connected to first housing portion 802 with any suitable means. First optical housing 806 includes passages 850 and passages 870 that extend from a first side of first optical housing 806 to a second side of first optical housing 806. Second optical housing 808 is connected to second housing portion 804 on the second side of heat block 810. Second optical housing 808 can be connected to second housing portion 804 with any suitable means. Second optical housing 808 includes passages 860 and passages 880 that extend from a first side of second optical housing 808 to a second side of second optical housing 808. Passages 850, passages 860, passages 870, and passages 880 provide pathways through which radiation can travel through optical assembly 800.

Excitation filters 852 are positioned between first optical housing 806 and first housing portion 802. Excitation filters 852 are aligned with passages 850 in first optical housing 806 and passages 854 in first housing portion 802. Excitation filters 862 are positioned between second optical housing 808 and second housing portion 804. Excitation filters 862 are aligned with passages 860 in second optical housing 808 and passages 864 in second housing portion 804. In the embodiment shown, excitation filters 852 and excitation filters 862 are shown as a plurality of filters but it could be one filter in alternate embodiments.

Emission filter 872 is positioned between first optical housing 806 and first housing portion 802. Emission filter 872 is aligned with passages 870 in first optical housing 806 and passages 874 in first housing portion 802. Emission filter 882 is positioned between second optical housing 808 and second housing portion 804. Emission filter 882 is aligned with passages 880 in second optical housing 808 and passage 884 in second housing portion 804. In the embodiment shown, emission filter 872 and emission filter 882 are each shown as one filter, but they could be a plurality of filters in alternate embodiments.

First light-emitting diode set 830 and first photodetector set 834 are positioned in first optical housing 806. Each light-emitting diode in first set 830 is positioned in one passage 850 in first optical housing 806. Each photodetector in first set 834 is positioned in one passage 870 in first optical housing 806. First light-emitting diode set 830 includes four clusters of three different light-emitting diodes, including light-emitting diode 840, light-emitting diode 842, and light-emitting diode 844. Each of light-emitting diode 840, light-emitting diode 842, and light-emitting diode 844 excites a biological sample at a different fluorescent wavelength. In the embodiment shown, light-emitting diode 840 can excite a first fluorescent dye, light-emitting diode 842 can excite a second fluorescent dye, and light-emitting diode 844 can excite a third fluorescent dye. First photodetector set 834 includes eight photodetectors 846. In the embodiment shown, each photodetector 846 detects radiation of two different wavelength band, here detecting the first fluorescent dye and the third fluorescent dye.

Second light-emitting diode set 832 and second photodetector set 836 are positioned in second optical housing 808. Each light-emitting diode in second set 832 is positioned in one passage 860 in second optical housing 808. Each photodetector in second set 836 is positioned in one passage 880 in second optical housing 808. Second light-emitting diode set 832 includes four clusters of three different light-emitting diodes, including light-emitting diode 840, light-emitting diode 842, and light-emitting diode 844. Each of light-emitting diode 840, light-emitting diode 842, and light-emitting diode 844 excites a biological sample at a different fluorescent wavelength. In the embodiment shown, light-emitting diode 840 can excite the first fluorescent dye, light-emitting diode 842 can excite the second fluorescent dye, and light-emitting diode 844 can excite the third fluorescent dye. Second photodetector set 836 includes eight photodetectors 846. In the embodiment shown, each photodetector 846 detects radiation of one wavelength band, here detecting the second fluorescent dye.

Multiple excitation passages extend through optical assembly 800 on both sides so that radiation can travel from first plurality of light-emitting diodes 830 and second plurality of light-emitting diodes 832 to heat block 810. A first plurality of excitation passages are formed on the first side of heat block 810. Each of the first plurality of excitation passages extend through one passage 850, one passage 854, and one passage 856. There are a plurality of passages 850 to accommodate each of the light-emitting diodes in first set 830. Thus, three passages 850 are positioned to pass into one passage 854. Further, excitation filters 852 are also positioned in the first plurality of excitation passages between passages 850 and passages 854. A second plurality of excitation passages are formed on the second side of heat block 810. Each of the second plurality of excitation passages extend through one passage 860, one passage 864, and one passage 866. There are a plurality of passages 860 to accommodate each of the light-emitting diodes in second set 832. Thus, three passages 860 are positioned to pass into one passage 864. Further, excitation filters 862 are also positioned in the second plurality of excitation passages between passages 860 and passages 864.

Multiple emission passages also extend through optical assembly 800 on both sides so that radiation can travel from heat block 810 to first set of photodetectors 834 and second set of photodetectors 836. A first plurality of emission passages are formed on the first side of heat block 810. Each of the first plurality of emission passages extend through one passage 876, one passage 874, and one passage 870. Further, emission filter 872 is positioned in each of the first plurality of emission passages between passages 874 and passages 870. A second plurality of emission passages are formed on the second side of heat block 810. Each of the second plurality of emission passages extend through one passage 886, one passage 884, and one passage 880. Further, emission filter 882 is positioned in each of the second plurality of emission passages between passages 884 and passages 880.

To excite a biological sample that is positioned in heat block 810, a light-emitting diode in either first light-emitting diode set 830 or second light-emitting diode set 832 is activated. If a light-emitting diode from first set 830 is activated, radiation will travel through passage 850, excitation filter 852, passage 854, and passage 856 into well 812 of heat block 810. If a light-emitting diode from second set 832 is activated, radiation will travel through passage 860, excitation filter 862, passage 864, and passage 866 into well 812 of heat block 810.

Radiation emitted from the biological sample that is positioned in heat block 810 will be detected by a photodetector in either first set 834 or second set 836. Each photodetector from first set 834 will read emission that has traveled from well 812 of heat block 810 through passage 876, passage 874, emission filter 872, and passage 870. Each photodetector from second set 836 will read emission that has traveled from well 812 of heat block 810 through passage 886, passage 884, emission filter 882, and passage 880.

Optical assembly 800 is advantageous, as it allows for multiple light-emitting diodes to be positioned around each well 812 in heat block 810. This allows a biological sample in wells 812 to be excited at a plurality of different radiation wavelengths. In the embodiment shown in FIGS. 29A-29D, a biological sample can include a first fluorescent dye, a second fluorescent dye, and a third fluorescent dye that can all be excited by a light-emitting diode. Optical assembly 800 is further advantageous, as it is a compact design with no moving parts. The compact design allows optical assembly 800 to be used in portable testing devices to test biological materials in the field.

Card 900

Figure 30A:
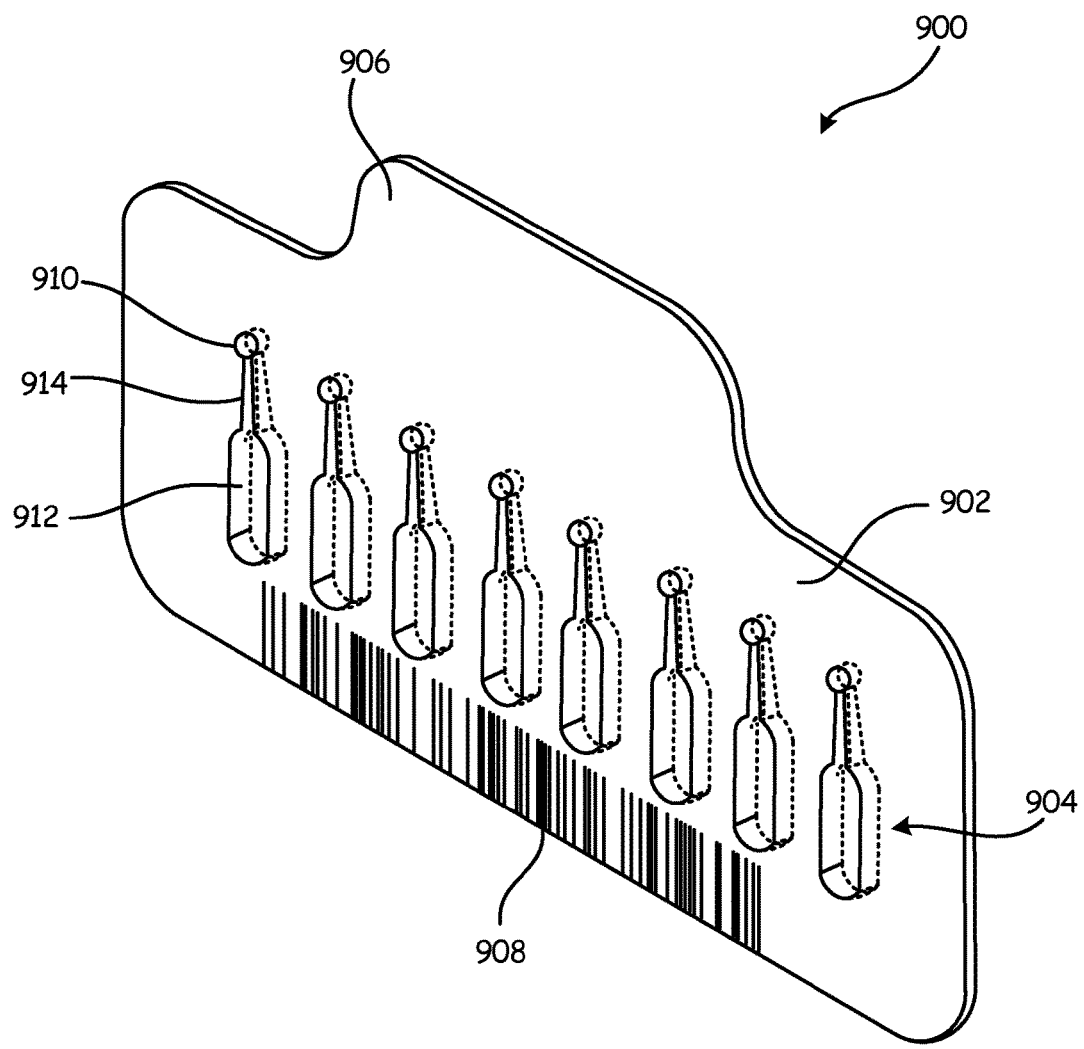
FIG. 30A is perspective view of a card.
Figure 30B:
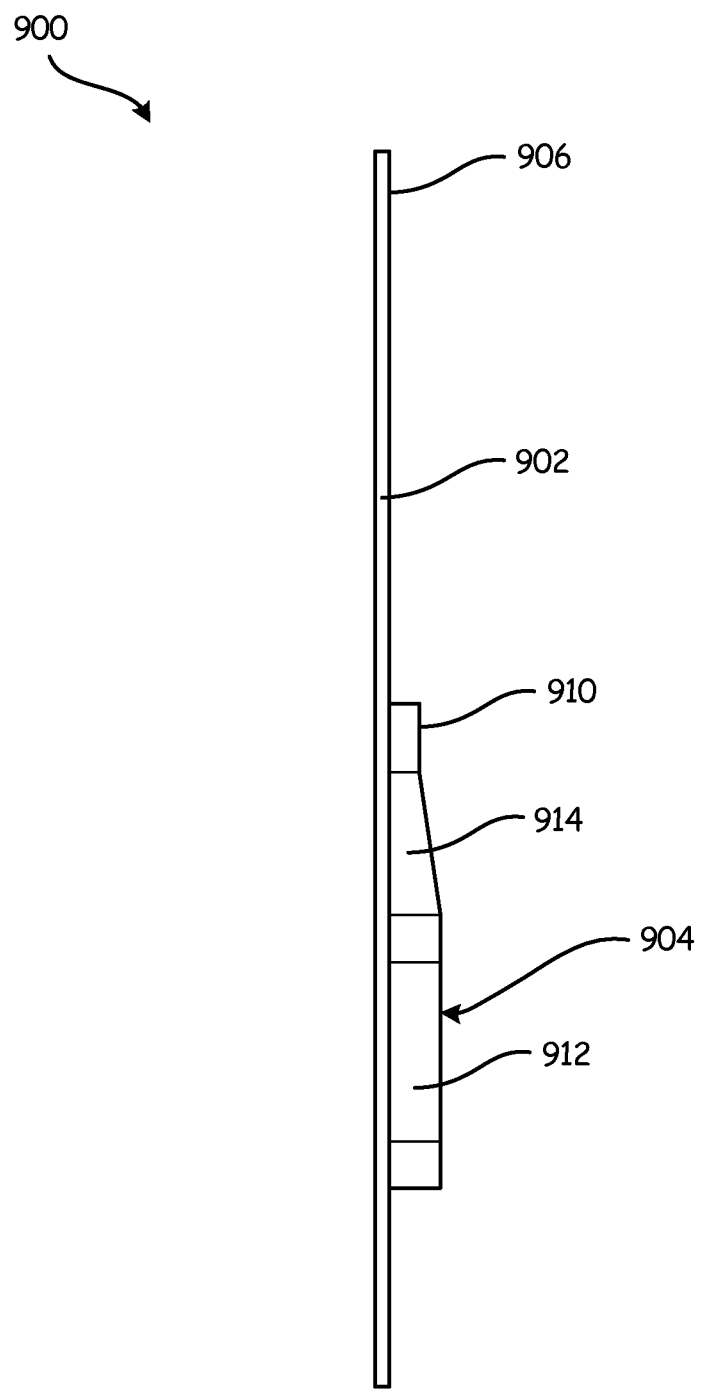
FIG. 30B is a side elevation view of the card.
Figure 30C:
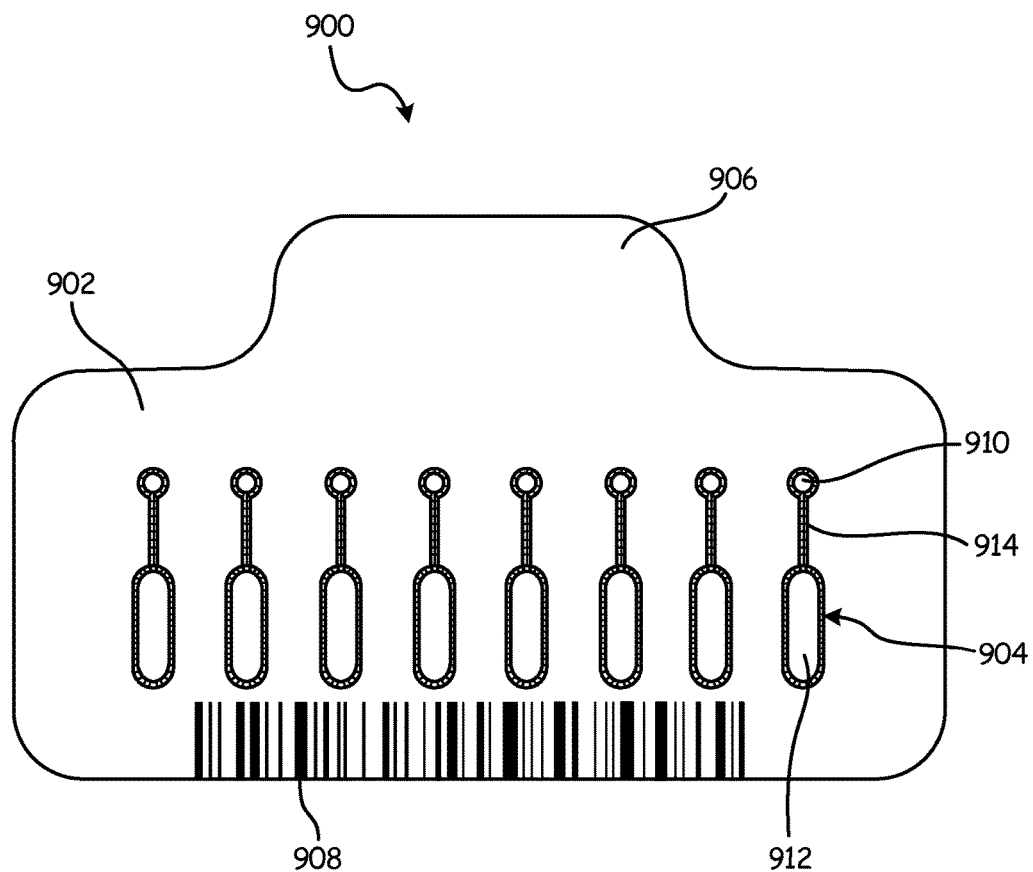
FIG. 30C is a front elevation view of the card.

FIG. 30A is perspective view of card 900. FIG. 30B is a side elevation view of card 900. FIG. 30C is a front elevation view of card 900. Card 900 includes body 902, wells 904, handle or tab 906, and code 908. Each well 904 includes first cavity 910, second cavity 912, and channel 914.

Card 900 is capable of receiving a biological material that will undergo nucleic acid amplification and then be tested. Card 900 is formed by body 902. Body 902 is made out of a transparent plastic in the embodiment shown, but can be made out of any suitable material in alternate embodiments. Card 900 includes a plurality of wells 904 on body 902. Wells 904 are embossed into body 902 during manufacturing of card 900. Body 902 also includes handle 906 at a top side of body 902. Handle 906 is a rectangular protrusion from body 902 in the embodiment shown and allows a user to easily grasp card 900. Code 908 is also printed on body 902 of card 900. Code 908 is a machine readable code that can be read by a machine code reader when card 900 is placed in a device for testing.

Each well 904 on card 900 includes first cavity 910, second cavity 912, and channel 914. First cavity 910 and second cavity 912 are positioned apart from one another. Channel 914 runs between first cavity 910 and second cavity 912 and connects them. First cavity 910 is capable of receiving a biological sample. After the biological sample is placed in first cavity 910 it will travel through channel 914 into second cavity 912. Second cavity 912 can contain a reaction mixture that the biological sample can mix with. Nucleic acid amplification can then be conducted when the biological sample is in second cavity 912. The biological sample in second cavity 912 can be excited and detected from a first side and a second side of card 900.

Card 900 is a sample holder in which a biological material can undergo nucleic acid amplification. Card 900 is advantageous over previous sample holder products for conducting nucleic acid amplification, as card 900 has a streamlined design and is easy to manage. With previous sample holders, there were multiple parts and components that were difficult to grasp and hold steady when dispensing a biological material into the sample holder. Card 900 is formed with one main body 902, making it easy to manage. Card 900 can be held with handle 906 or laid flat on a table when a biological material is being dispensed. This makes card 900 capable of being used in a field with a portable testing device, as no separate holding station or support structure is required to support card 900.

Card 900 is further advantageous, as card 900 can come preloaded with a reaction mixture in second cavities 912. This streamlines the process of preparing card 900 for testing. Further, card 900 includes code 908. Code 908 is a machine readable code that can be read by the device in which card 900 is placed. Code 908 can include information about what test protocol to run with a specific card 900, including embedded end point call algorithms and reaction mixture traceability information. Code 908 can further include additional information that can be read by the portable testing device.

Figure 31A:
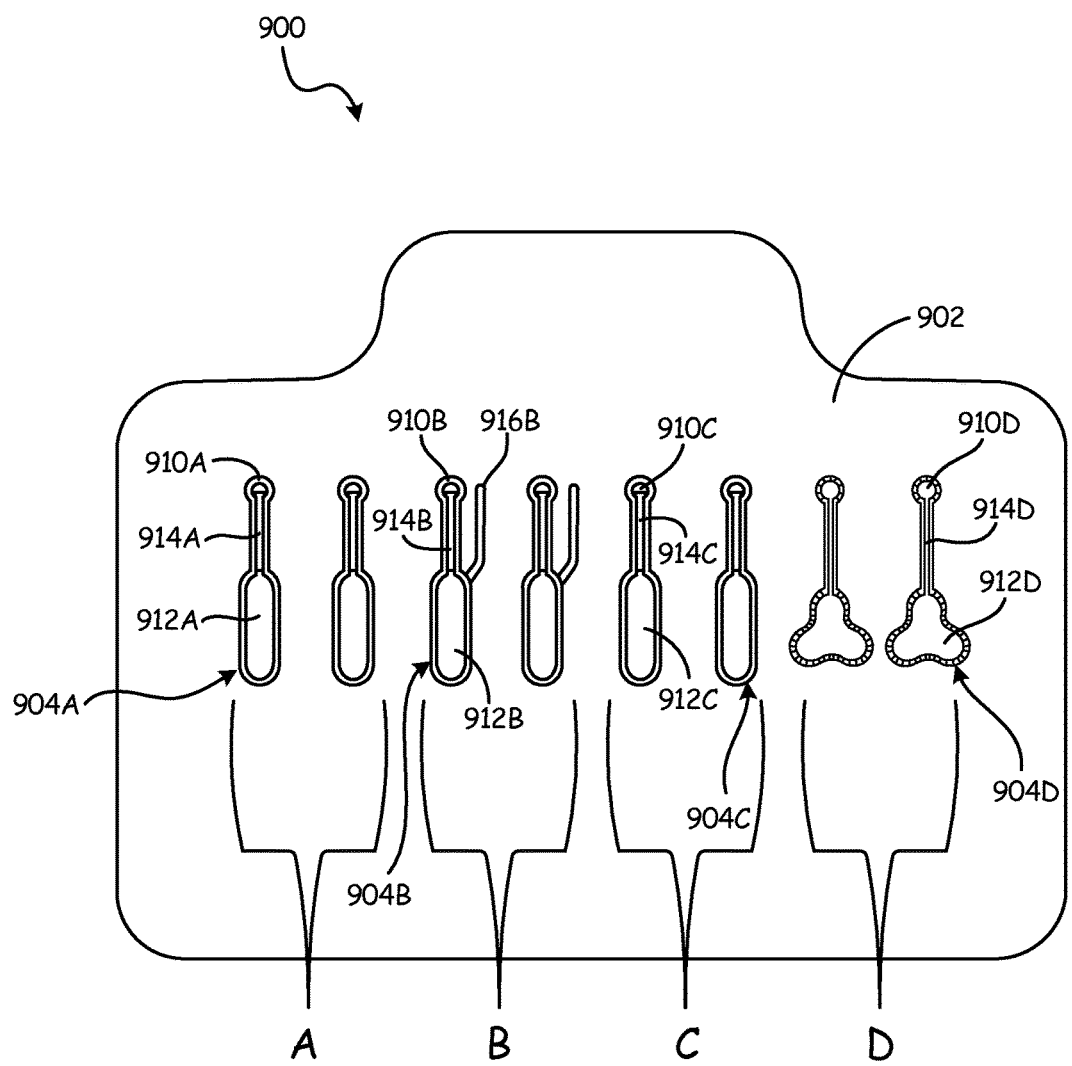
FIG. 31A is a front elevation view of the card showing well variations A-D.
Figure 31B:
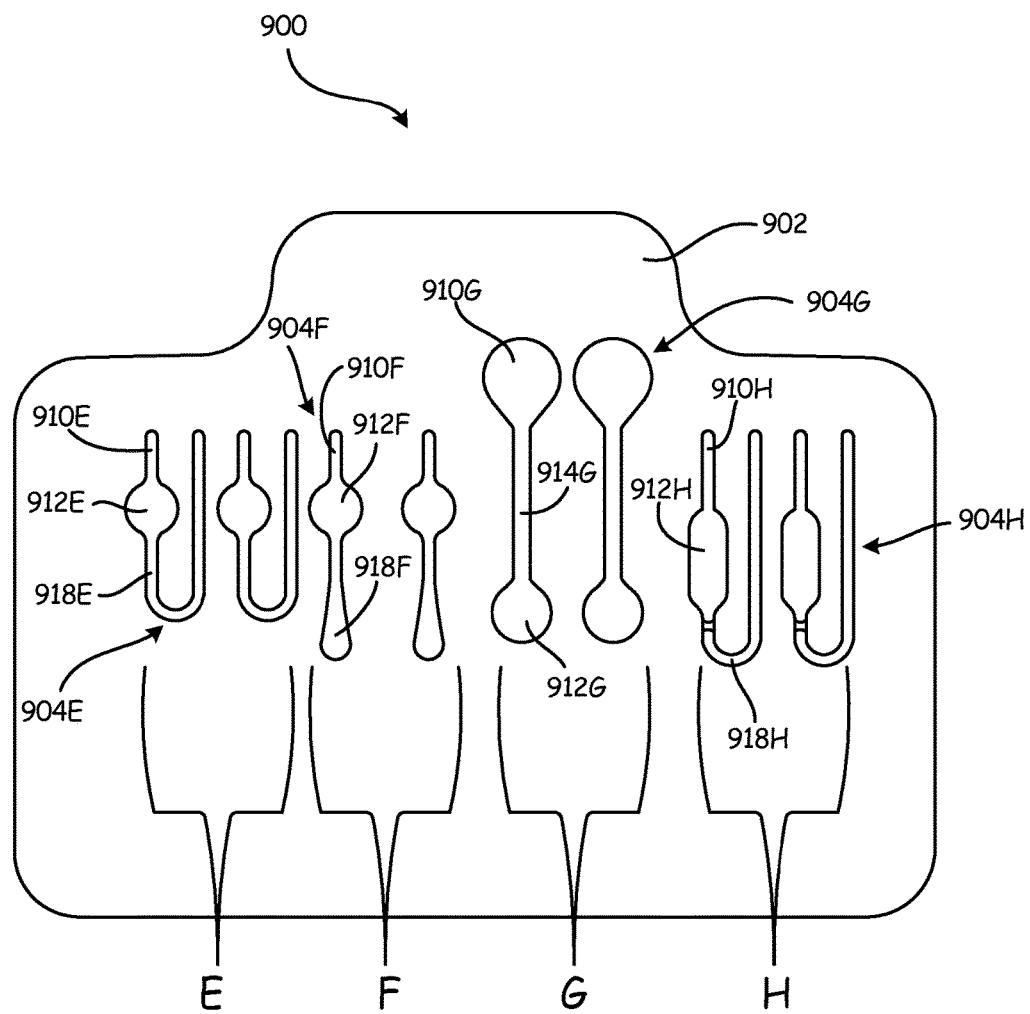
FIG. 31B is a front elevation view of the card showing well variations E-H.

FIG. 31A is a front elevation view of card 900 showing well variations A-D. FIG. 31B is a front elevation view of card 900 showing well variations E-H. Card 900 includes body 902 and wells 904, including wells 904A, wells 904B, wells 904C, wells 904D, wells 904E, wells 904F, wells 904G, and wells 904H. Wells 904 can include first cavities 910, second cavities 912, channels 914, air ducts 916, and third cavities 918.

Card 900 includes body 902. Wells 904 are positioned on body 902. Wells 904 can take any number of shapes, some variations of which are seen in FIGS. 31A-31B. Wells 904 are all capable of receiving a biological sample and mixing the biological sample with a reaction mixture that is preloaded in wells 904. The biological sample in each well 904 can then undergo nucleic acid amplification and testing.

Wells 904A each include first cavity 910A, second cavity 912A, and channel 914A. First cavity 910A and second cavity 912A are positioned apart from one another. First cavity 910A has a circular shape and a first depth. Second cavity 912A has an oval shape and a second depth. Channel 914A runs between first cavity 910A and second cavity 912A and connects them. Channel 914A has a changing depth, starting with the first depth at first cavity 910A and ending with the second depth at second cavity 912A. First cavity 910A is capable of receiving a biological sample. After the biological sample is placed in first cavity 910A it will travel through channel 914A into second cavity 912A. Second cavity 912A can contain a reaction mixture that the biological sample can mix with. Nucleic acid amplification can then be conducted when the biological sample is in second cavity 912A.

Wells 904B each include first cavity 910B, second cavity 912B, channel 914B, and air duct 916B. First cavity 910B and second cavity 912B are positioned apart from one another. First cavity 910B has a circular shape. Second cavity 912B has an oval shape. Channel 914B runs between first cavity 910B and second cavity 912B and connects them. First cavity 910B is capable of receiving a biological sample. After the biological sample is placed in first cavity 910B it will travel through channel 914B into second cavity 912B. Air duct 916B is connected to channel 914B and allows air in channel 914B to be expelled when the biological sample travels through channel 914B. Second cavity 912B can contain a reaction mixture that the biological sample can mix with. Nucleic acid amplification can then be conducted when the biological sample is in second cavity 912B.

Wells 904C each include first cavity 910C, second cavity 912C, and channel 914C. First cavity 910C and second cavity 912C are positioned apart from one another. First cavity 910C has a circular shape and has a first depth. Second cavity 912C has an oval shape and has the same depth as first cavity 910C. Channel 914C runs between first cavity 910C and second cavity 912C and connects them. Channel 914C has the same depth as both first cavity 910C and second cavity 912C. First cavity 910C is capable of receiving a biological sample. After the biological sample is placed in first cavity 910C it will travel through channel 914C into second cavity 912C. Second cavity 912C can contain a reaction mixture that the biological sample can mix with. Nucleic acid amplification can then be conducted when the biological sample is in second cavity 912C.

Wells 904D each include first cavity 910D, second cavity 912D, and channel 914D. First cavity 910D and second cavity 912D are positioned apart from one another. First cavity 910D has a circular shape. Second cavity 912D has a shape that mimics three overlapping circles. Channel 914D runs between first cavity 910D and second cavity 912D and connects them. First cavity 910D is capable of receiving a biological sample. After the biological sample is placed in first cavity 910D it will travel through channel 914D into second cavity 912D. Second cavity 912D can contain a reaction mixture that the biological sample can mix with. Nucleic acid amplification can then be conducted when the biological sample is in second cavity 912D. The shape of second cavity 912D allows for a light-emitting diode and a photodetector to be positioned over each of one of the three overlapping circles. This allows three different light-emitting diodes and three different photodetectors to be aligned with second cavity 912D.

Wells 904E each include first cavity 910E, second cavity 912E, and third cavity 918E. First cavity 910E has a thin rectangular shape. Second cavity 912E has a circular shape. Third cavity 918E has a thin horseshoe shape. First cavity 910E is connected directly to second cavity 912E and second cavity 912E is connected directly to third cavity 918E. First cavity 910E is capable of receiving a biological sample. After the biological sample is placed in first cavity 910E it will travel into second cavity 912E. Second cavity 912E can contain a reaction mixture that the biological sample can mix with. Nucleic acid amplification can then be conducted when the biological sample is in second cavity 912E. Any excess air or fluid in well 904E can travel into third cavity 918E. In an alternate embodiment, the biological sample could be received in third cavity 918E and excess air or fluid could accrue in first cavity 910E.

Wells 904F each include first cavity 910F, second cavity 912F, and third cavity 918F. First cavity 910F has a thin rectangular shape. Second cavity 912F has a circular shape. Third cavity 918F has a teardrop shape. First cavity 910F is connected directly to second cavity 912F and second cavity 912F is connected directly to third cavity 918F. First cavity 910F is capable of receiving a biological sample. After the biological sample is placed in first cavity 910F it will travel into second cavity 912F. Second cavity 912F can contain a reaction mixture that the biological sample can mix with. Nucleic acid amplification can then be conducted when the biological sample is in second cavity 912F. Any excess air or fluid in well 904F can travel into third cavity 918F.

Wells 904G each include first cavity 910G, second cavity 912G, and channel 914G. First cavity 910G and second cavity 912G are positioned apart from one another. First cavity 910G has a circular shape. Second cavity 912G has a circular shape. Channel 914G runs between first cavity 910G and second cavity 912G and connects them. First cavity 910G is capable of receiving a biological sample. After the biological sample is placed in first cavity 910G it will travel through channel 914G into second cavity 912G. Second cavity 912G can contain a reaction mixture that the biological sample can mix with. Nucleic acid amplification can then be conducted when the biological sample is in second cavity 912G.

Wells 904H each include first cavity 910H, second cavity 912H, and third cavity 918H. First cavity 910H has a thin rectangular shape. Second cavity 912H has a rectangular shape with rounded corners. Third cavity 918H has a thin horseshoe shape. First cavity 910H is connected directly to second cavity 912H. Second cavity 912H is connected to third cavity 918H with a restriction feature. First cavity 910H is capable of receiving a biological sample. After the biological sample is placed in first cavity 910H it will travel into second cavity 912H. Second cavity 912H can contain a reaction mixture that the biological sample can mix with. The restriction feature between second cavity 912H and third cavity 918H allows air to pass from second cavity 912H to third cavity 918H, but retains fluids in second cavity 912H. Nucleic acid amplification can then be conducted when the biological sample is in second cavity 912H.

Card 900 is advantageous because a plurality of differently shaped wells 904 can be used. Wells 904A-904H shown in FIGS. 31A-31B are a small sampling of the variety of differently shaped wells 904 that could be produced. Card 900 allows a biological material to be placed in wells 904 and travel through each well 904 to mix with a reaction mixture. The biological sample and reagent mixture can then undergo nucleic acid amplification and can be tested. Each well 904 requires a small amount of reaction mixture and biological material to conduct the nucleic acid amplification and testing. This will save money in materials. Further, less biological sample needs to be collected in order to complete a test.

Figure 32A:
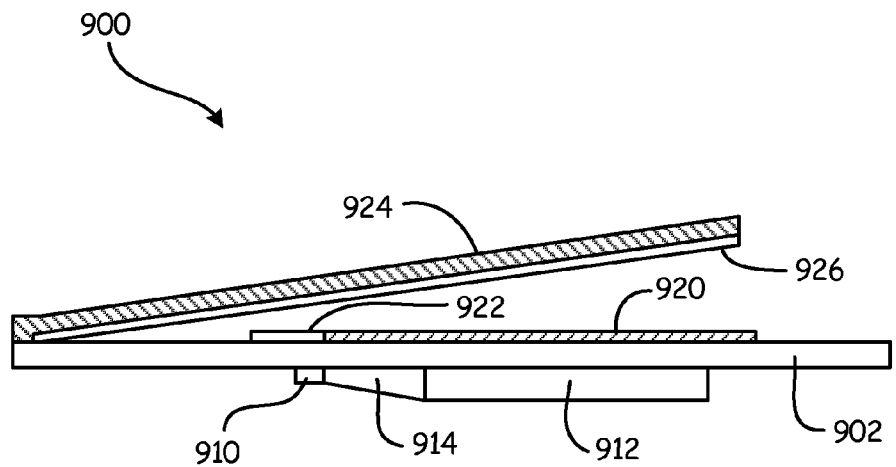
FIG. 32A is a side elevation view of the card showing seals on the card.
Figure 32B:
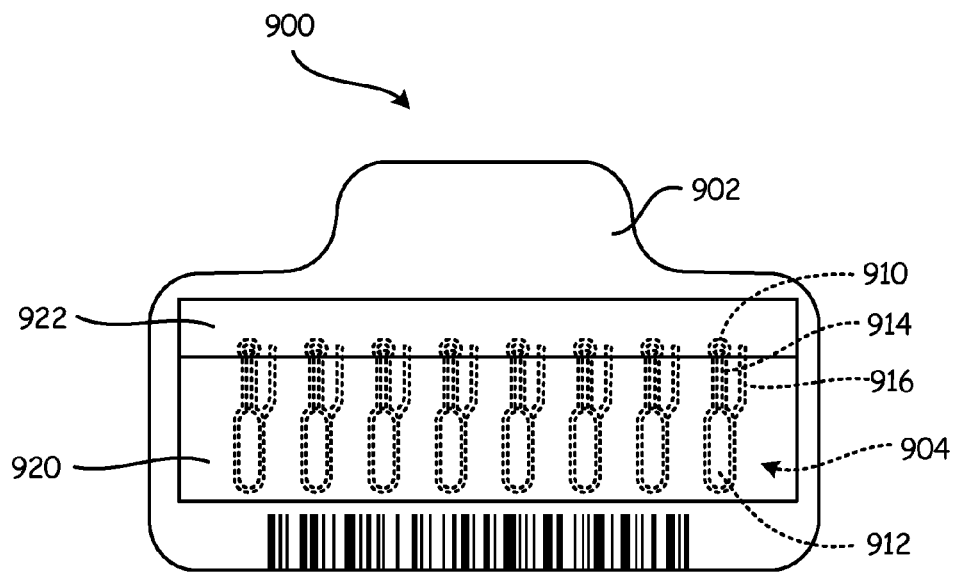
FIG. 32B is a front elevation view of the card showing a first permanent seal and a removable seal.
Figure 32C:
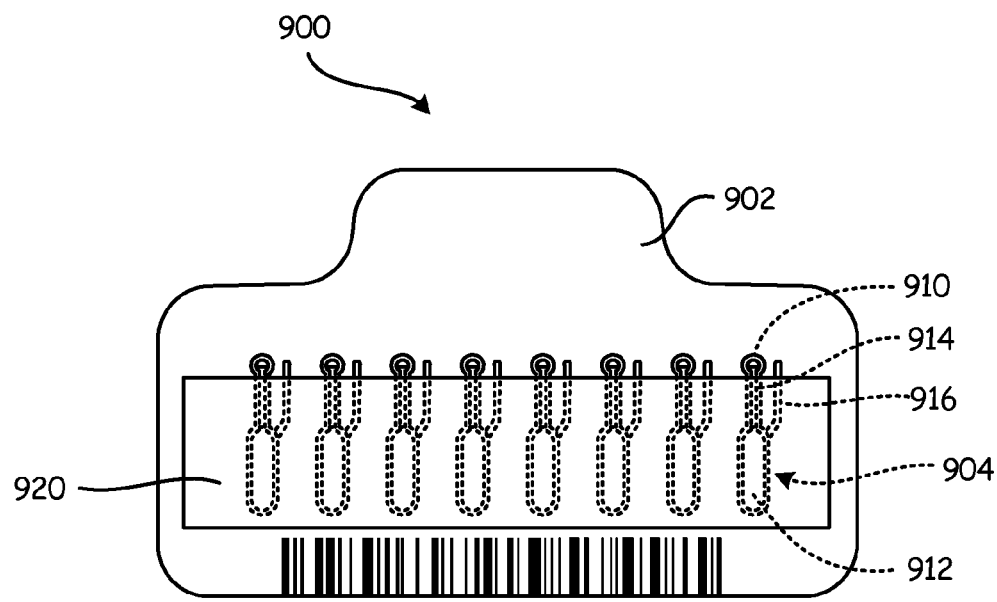
FIG. 32C is a front elevation view of the card after the removable seal is removed.
Figure 32D:
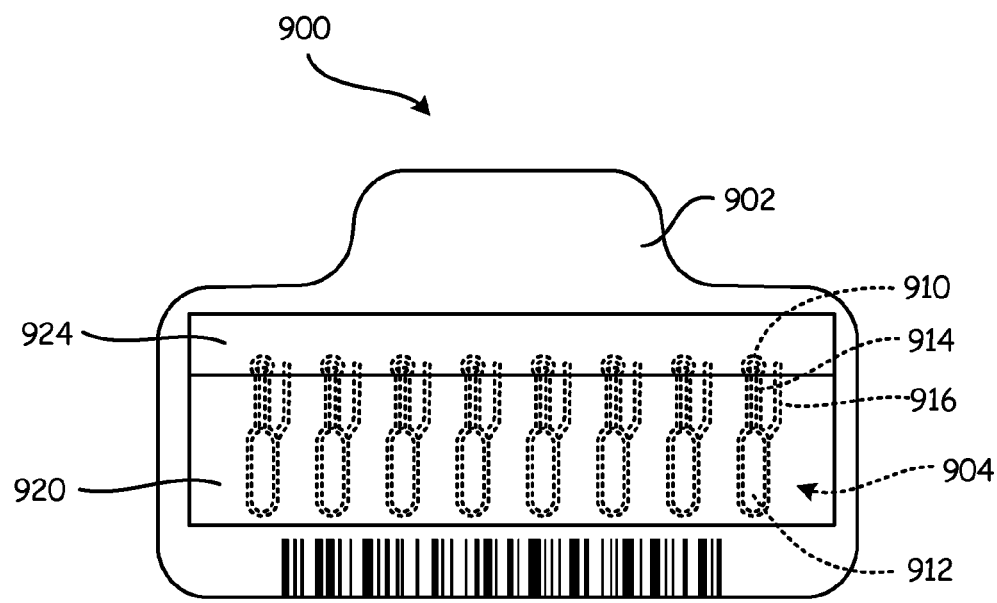
FIG. 32D is a front elevation view of the card after a second permanent seal is applied.

FIG. 32A is a side elevation view of card 900 showing seals on card 900. FIG. 32B is a front elevation view of card 900 showing first permanent seal 920 and removable seal 922. FIG. 32C is a front elevation view of card 900 after removable seal 922 is removed. FIG. 32D is a front elevation view of card 900 after second permanent seal 924 is applied. Card 900 includes body 902, wells 904, first permanent seal 920, removable seal 922, second permanent seal 924, and backing 926. Each well 904 includes first cavity 910, second cavity 912, and channel 914.

Card 900 includes wells 904 that are positioned on body 902 of card 900. Each well 904 on card 900 includes first cavity 910, second cavity 912, and channel 914. First cavity 910 and second cavity 912 are positioned apart from one another. Channel 914 runs between first cavity 910 and second cavity 912 and connects them. First cavity 910 is capable of receiving a biological sample. After the biological sample is placed in first cavity 910 it will travel through channel 914 into second cavity 912. Second cavity 912 can contain a reaction mixture with which the biological sample can mix. Nucleic acid amplification can then be conducted when the biological sample is in second cavity 912.

Card 900 further includes first permanent seal 920, removable seal 922, second permanent seal 924, and backing 926. First permanent seal 920 is positioned on body 902 of card 900 and covers channels 914 and second cavities 912 of wells 904. Removable seal 922 is positioned on body 902 of card 900 and covers first cavities 910 of wells 904. Second permanent seal 924 is attached to a top portion of body 902 of card 900, but second permanent seal 924 is not initially sealed onto body 902 of card 900. Backing 926 is attached to second permanent seal 924.

First permanent seal 920 and removable seal 922 can be sealed to card 900 prior to the sale of card 900. During manufacturing of the card, a reaction mixture can be added to second cavities 912 of wells 904. The reaction mixture can come in liquid form or it can be lyophilized. After the reaction mixture is added, first permanent seal 920 can be applied to card 900 to seal channels 914 and second cavities 912 of wells 904. Removable seal 922 can also be applied to card 900 to seal first cavities 910 of wells 904. Second permanent seal 924 and backing 926 can also be attached to a top portion of body 902 of card 900. This can be seen in FIGS. 32A-32B.

When a user wants to place a biological material in wells 904, removable seal 922 can be removed from body 902 of card 900, as seen in FIG. 32C. This will expose first cavities 910 of wells 904. A biological sample can then be placed in first cavities 910, usually by pipetting the biological sample in liquid form into first cavities 910. As the biological sample is placed in first cavities 910, it can travel through channels 914 into second cavities 912. When the biological sample reaches second cavities 912 it can mix with the reaction mixture that was previously placed in second cavities 912. After the biological sample has been fully loaded into card 900, backing 926 can be removed from second permanent seal 924. Second permanent seal 924 can then be placed on body 902 of card 900 to fully seal wells 904, as seen in FIG. 32D. Second permanent seal 924 covers first cavities 910 and first permanent seal 920 in the embodiment shown. In alternate embodiments, second permanent seal 924 can cover only first cavities 910 or it can cover first cavities 910 and a portion of first permanent seal 920.

Card 900 is advantageous, as it allows a user to easily load a biological sample into a sample holder. Card 900 is further advantageous, as it can come preloaded with a reaction mixture. After the biological sample is loaded into card 900, it will mix with the reaction mixture to prepare it for nucleic acid amplification. This is a simple way to prepare the biological sample for testing. Further, the seals that are provided on card 900 make it easy for a user to load a biological sample into card 900 while preventing contamination of wells 904.

Card 1000

Figure 33A:
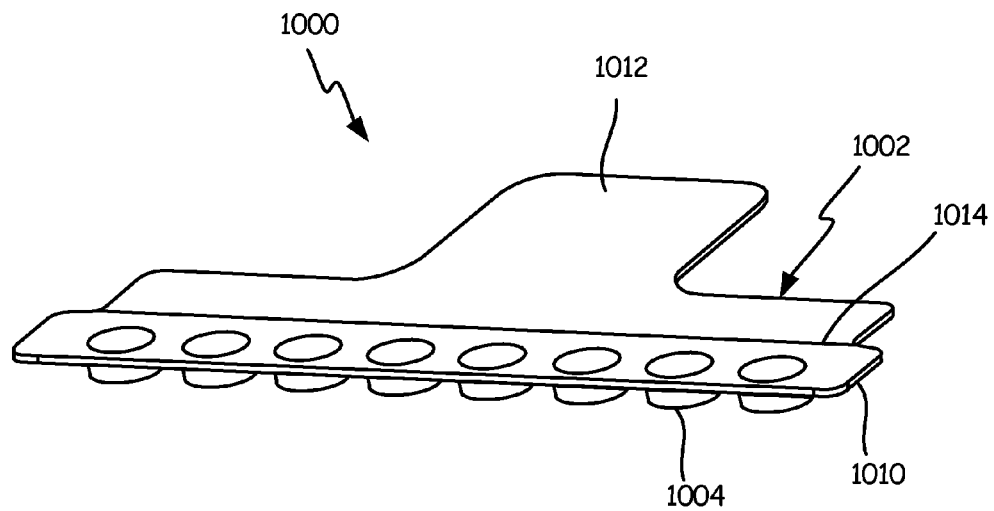
FIG. 33A is a perspective view of a top side of a card.
Figure 33B:
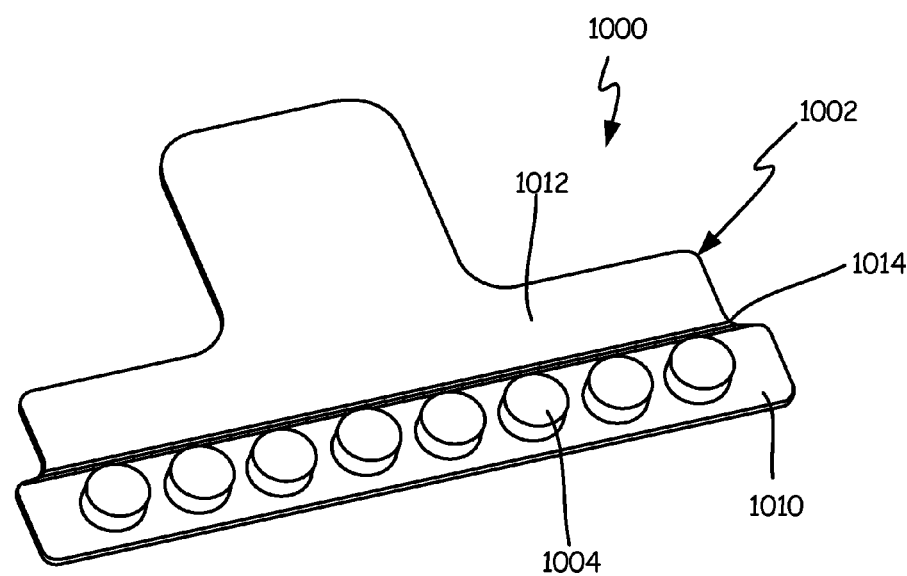
FIG. 33B is a perspective view of a bottom side of the card.

FIG. 33A is a perspective view of a top side of card 1000. FIG. 33B is a perspective view of a bottom side of card 1000. Card 1000 includes body 1002 and wells 1004. Body 1002 includes first body portion 1010, second body portion 1012, and hinge 1014.

Card 1000 is capable of receiving a biological material that will undergo nucleic acid amplification and be tested. Card 1000 is formed with body 1002. Body 1002 is made out of a transparent plastic in the embodiment shown, but can be any suitable material in alternate embodiments. Body 1002 includes first body portion 1010, second body portion 1012, and hinge 1014. First body portion 1010 is a rectangular shape. Second body portion 1012 is a T-shape. A first long side of first body portion 1010 is attached to the top long portion of the T-shape of second body portion 1012 along hinge 1014. First body portion 1010 and second body portion 1012 can be folded towards or away from one another along hinge 1014. First body portion 1010 is wider than second body portion 1012, which allows first body portion 1010 to be secured when a biological sample is placed in first body portion 1010 or when second body portion 1012 is sealed with first body portion 1010.

A plurality of wells 1004 are positioned on first body portion 1010. Each well 1004 is a circular shape and wells 1004 are positioned in a line on first body portion 1010. Wells 1004 are capable of receiving biological samples and reactions mixtures to undergo nucleic acid amplification.

The T-shape of second body portion 1012 allows the vertical portion of the T-shape to act as a handle for card 1000. Second body portion 1012 can be easily grasped by a user to hold and move card 1000. Further, a machine readable code can be printed on the handle of second body portion 1012. When card 1000 is placed in a device, a code reader can read the machine readable code on second body portion 1012. The machine readable code can indicate what test protocol to run, among other information.

Card 1000 is advantageous, as it allows a user to prepare a biological sample for testing on a compact and easy-to-use sample holder. Biological materials can be easily placed in wells 1004 and mixed with reaction mixtures. Further, the design of card 1000 with a handle on second body portion 1012 makes card 1000 easy to grasp and maneuver. Card 1000 allows a user to conduct nucleic acid amplification of small sample amounts in wells 1004.

Figure 34A:
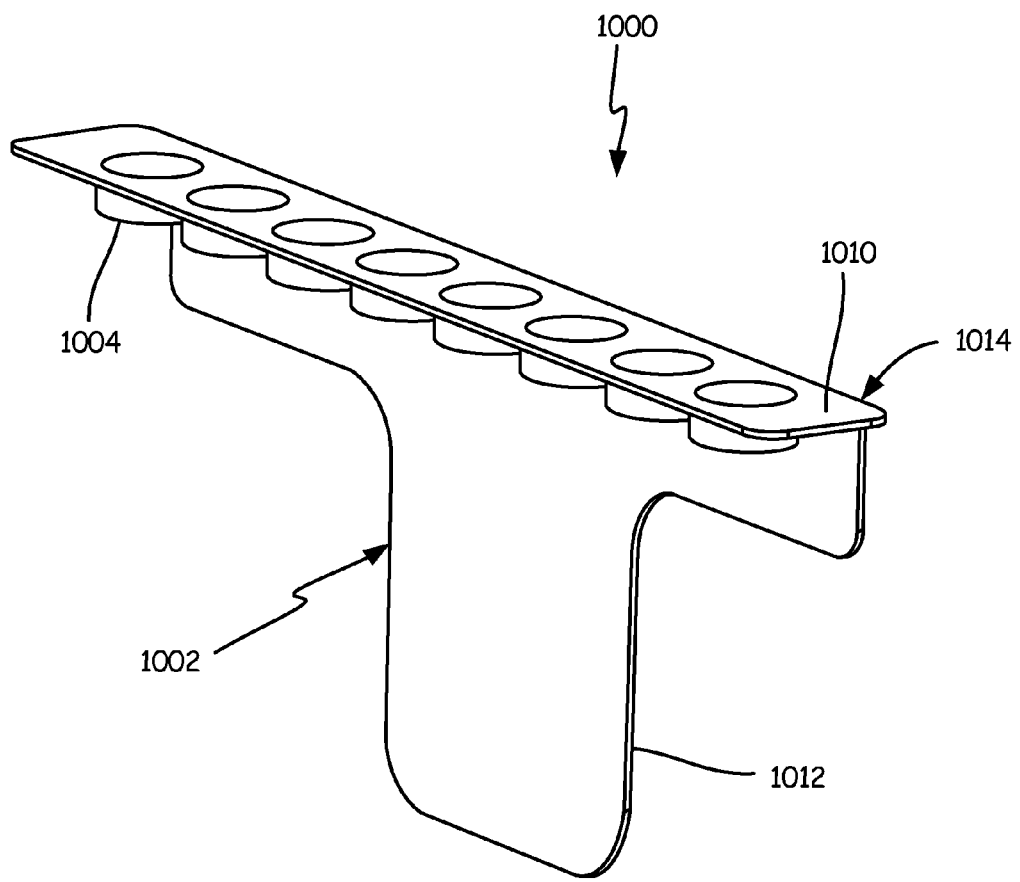
FIG. 34A is a perspective view of the card when a second body portion is rotated down.
Figure 34B:
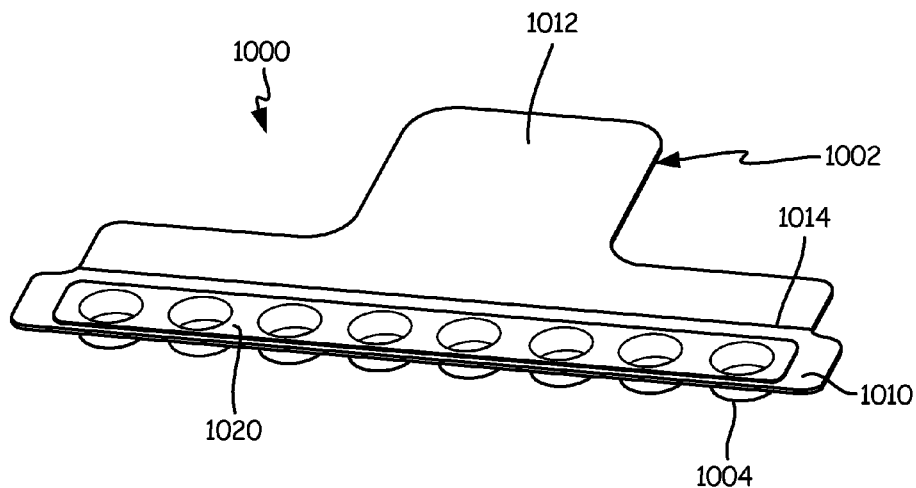
FIG. 34B is a perspective view of the card with a first permanent seal.

FIG. 34A is a perspective view of card 1000 when second body portion 1012 is rotated down. FIG. 34B is a perspective view of card 1000 with permanent seal 1020. FIG. 4C is a perspective view of card 1000 with first removable seal 1022. FIG. 34D is a perspective view of card 1000 that can be placed in a lyophilizer. FIG. 34E is a perspective view of card 1000 with second removable seal 1026 placed over first removable seal 1022. Card 1000 includes body 1002, wells 1004, permanent seal 1020, first removable seal 1022, openings 1024, and second removable seal 1026. Body 1002 includes first body portion 1010, second body portion 1012, and hinge 1014.

Card 1000 is capable of receiving a biological material to undergo nucleic acid amplification. Card 1000 is formed with body 1002. Body 1002 includes first body portion 1010, second body portion 1012, and hinge 1014. First body portion 1010 and second body portion 1012 are attached along hinge 1014 and can be folded towards or away from one another along hinge 1014. A plurality of wells 1004 are positioned on first body portion 1010. Each well 1004 is a circular shape and wells 1004 are positioned in a line on first body portion 1010. In alternate embodiments, wells 1004 can be any shape, including oval, rectangular, or tear drop shaped. Wells 1004 are capable of receiving biological samples and reactions mixtures to undergo nucleic acid amplification.

To prepare card 1000 for testing, second body portion 1012 can first be folded downwards along hinge 1014. This allows a user to either grasp second body portion 1012 to hold card 1000 steady or to place second body portion 1012 in a holder to support card 1000. When card 1000 is held steady or supported, a reaction mixture can be dispensed into wells 1004, as seen in FIG. 34A. The reaction mixture is typically dispensed in liquid form.

Either before or right after the reaction mixture is dispensed into wells 1004, permanent seal 1020 can be applied to first body portion 1010, as seen in FIG. 34B. Permanent seal 1020 is a permanent adhesive that is applied to a top side of first body portion 1010 surrounding wells 1004 in the embodiment shown. In alternate embodiments, permanent seal 1020 can be any suitable seal.

Figure 34C:
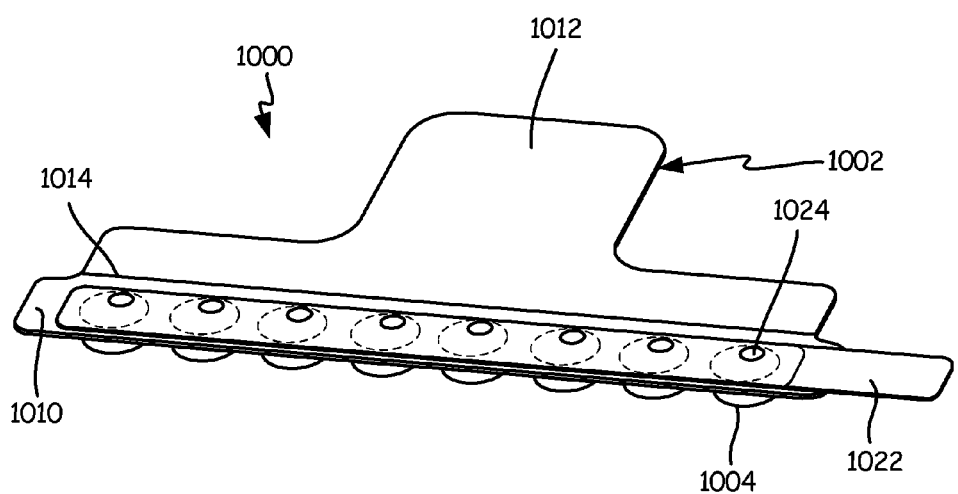
FIG. 34C is a perspective view of the card with a first removable seal.
Figure 34D:
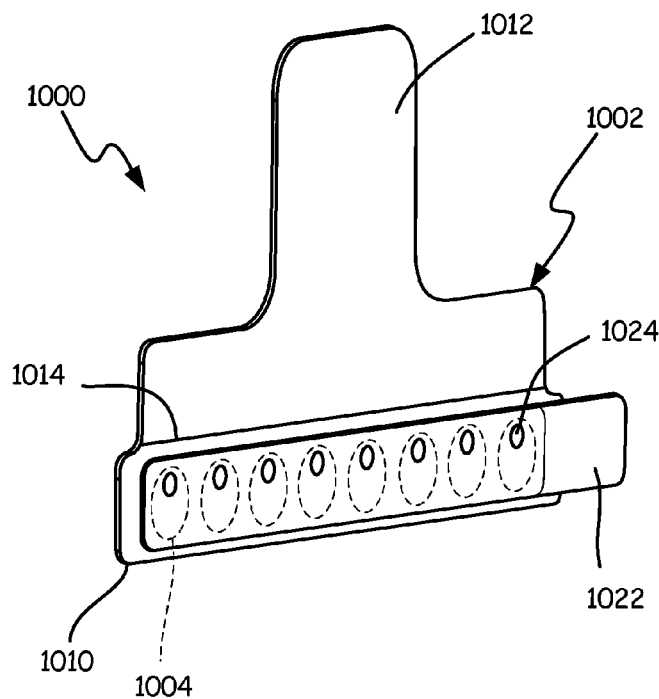
FIG. 34D is a perspective view of the card that can be placed in a lyophilizer.
Figure 34E:
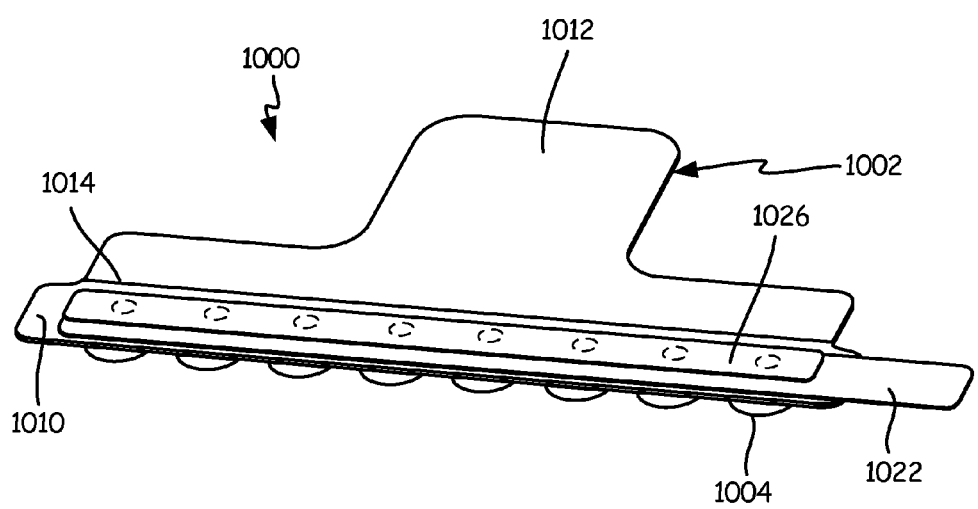
FIG. 34E is a perspective view of the card with second removable seal placed over the first removable seal.

After permanent seal 1020 is applied and the reaction mixture has been dispensed into wells 1004, first removable seal 1022 is placed over permanent seal 1020, as seen in FIG. 34C. First removable seal 1022 can be any material that is suitable for use as a seal and that can be easily removed from permanent seal 1020. First removable seal 1022 has a plurality of openings 1024 in it. One opening 1024 is positioned over each well 1004. Openings 1024 are provided to allow moisture laden air to flow into and out of wells 1004 during the remaining preparation steps.

After first removable seal 1022 has been placed over wells 1004, card 1000 can be placed in a lyophilizer, as seen in FIG. 34D. Card 1000 can be inserted into the lyophilizer in any orientation. A lyophilizer will dry-down the liquid reaction mixture that is in wells 1004. Openings 1024 in first removable seal 1022 allow air to pass into and out of wells 1004 during lyophilization.

After the reaction mixture in wells 1004 is lyophilized, second removable seal 1026 can be placed over openings 1024 in first removable seal 1022, as seen in FIG. 34E. Second removable seal 1026 can be any material that is suitable for use as a seal. Placing second removable seal 1026 over first removable seal 1022 will cover openings 1024 in first removable seal 1022. This will seal the lyophilized reaction mixture into wells 1004 and it will prevent wells 1004 from being contaminated.

As seen from the above steps, card 1000 can be easily prepared for nucleic acid amplification and testing. First removable seal 1022 and second removable seal 1026 are applied to card 1000 during preparation of card 1000 to protect card 1000 from contamination. First removable seal 1022 and second removable seal 1026 can be easily removed from card 1000 when a biological material is to be placed in wells 1004. Card 1000 is further advantageous, as it comes with a lyophilized reaction mixture preloaded into wells 1004. This makes it easy to prepare a biological sample in card 1000 for nucleic acid amplification. The ease of preparation makes card 1000 suitable for use in the field.

Figure 35A:
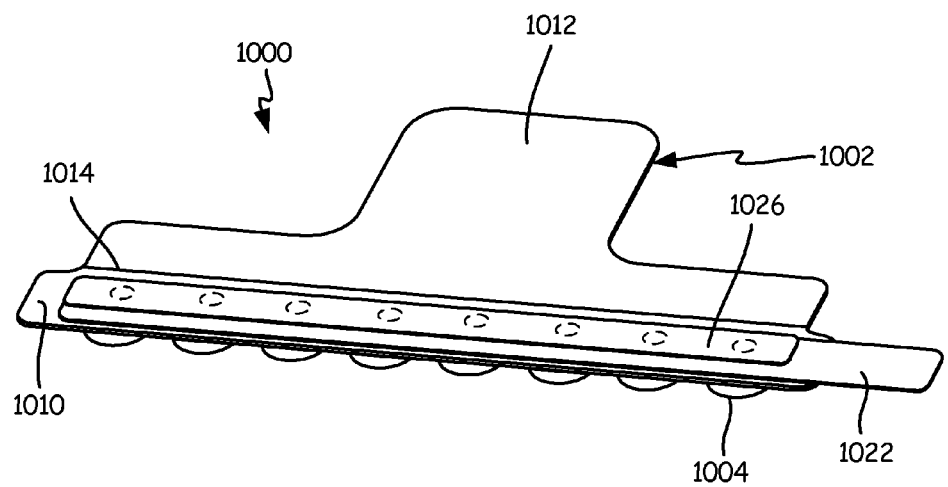
FIG. 35A is a perspective view of the card with the first removable seal and the second removable seal.
Figure 35B:
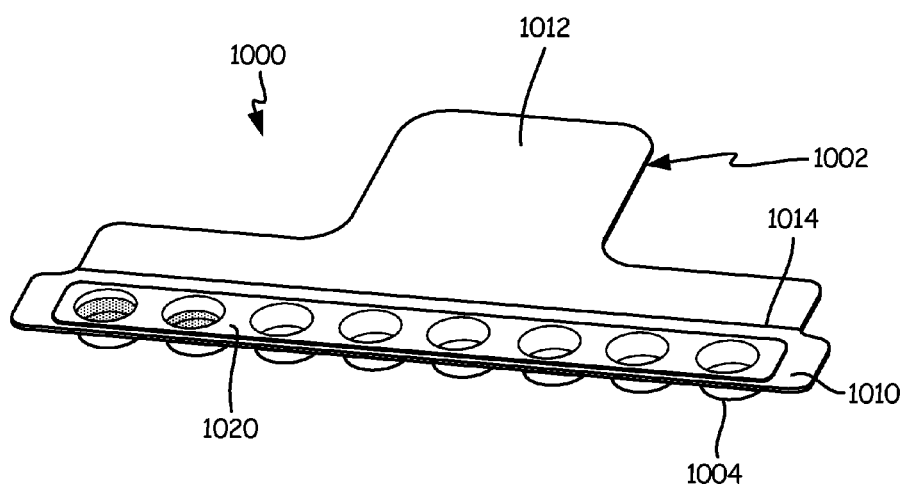
FIG. 35B is a perspective view of the card with the first removable seal and the second removable seal removed to provide access to the wells.
Figure 35C:
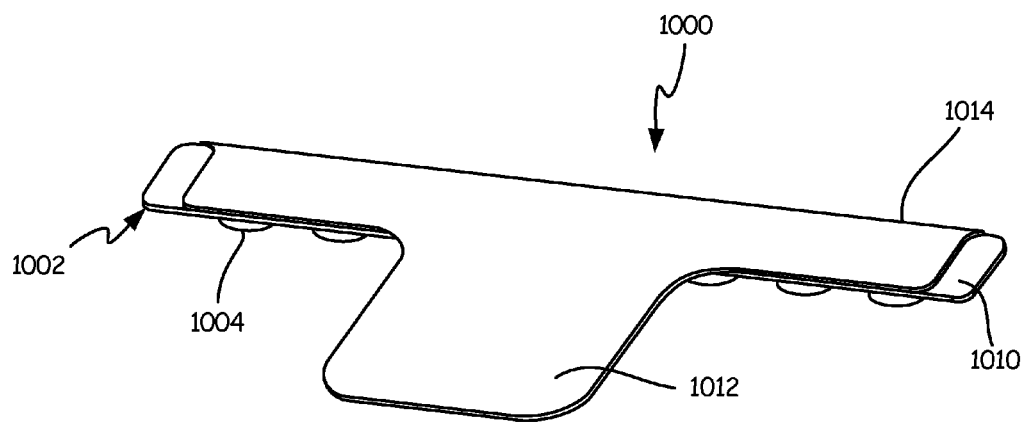
FIG. 35C is a perspective view of the card when the second body portion is folded over the wells to seal the wells with the permanent seal.
Figure 35D:
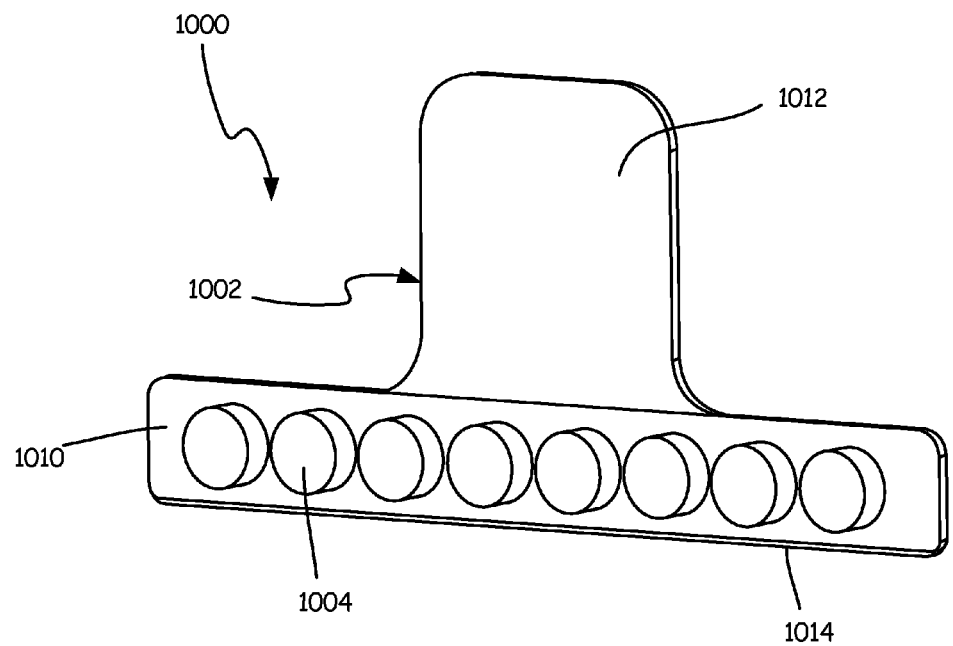
FIG. 35D is a perspective view of the card that is prepared for testing.

FIG. 35A is a perspective view of card 1000 with first removable seal 1022 and second removable seal 1026. FIG. 35B is a perspective view of card 1000 with first removable seal 1022 and second removable seal 1026 removed to provide access to wells 1004. FIG. 35C is a perspective view of card 1000 when second body portion 1012 is folded over wells 1004 to seal wells 1004 with permanent seal 1020. FIG. 35D is a perspective view of card 1000 that is prepared for testing. Card 1000 includes body 1002, wells 1004, permanent seal 1020, first removable seal 1022, openings 1024, and second removable seal 1026. Body 1002 includes first body portion 1010, second body portion 1012, and hinge 1014.

Card 1000 is capable of receiving a biological material to undergo nucleic acid amplification. Card 1000 is formed with body 1002. Body 1002 includes first body portion 1010, second body portion 1012, and hinge 1014. First body portion 1010 and second body portion 1012 are attached along hinge 1014 and can be folded towards or away from one another along hinge 1014. A plurality of wells 1004 are positioned on first body portion 1010. Each well 1004 is a circular shape and wells 1004 are positioned in a line on first body portion 1010. Wells 1004 are capable of receiving biological samples and reactions mixtures that can undergo nucleic acid amplification.

After a user has obtained card 1000, the user can place a biological sample into wells 1004 of card 1000 to test the biological sample. Card 1000 is shown in FIG. 35A as it would be received by a user. To prepare the biological sample and card 1000 for testing, first removable seal 1022 and second removable seal 1026 are removed from card 1000 by peeling them off of card 1000, as seen in FIG. 35B. This will expose permanent seal 1020. After first removable seal 1022 and second removable seal 1026 are removed, a biological sample can be placed in wells 1004. The biological sample that is placed in wells 1004 is typically in liquid form. The liquid can then mix with the lyophilized reaction mixture that was placed in wells 1004 during preparation of card 1000.

After a biological sample is placed in wells 1004, second body portion 1012 of card 1000 can be folded along hinge 1014 towards first body portion 1010. As seen in FIG. 35C, second body portion 1012 will come into contact with permanent seal 1020 on first body portion 1010. This will permanently seal wells 1004 of card 1000, as seen in FIG. 35D. After card 1000 is permanently sealed, a user can grasp the handle of second body portion 1012 to place card 1000 in a testing device.

Card 1000 is advantageous, as a biological sample can be easily loaded into card 1000 by removing first removable seal 1022 and second removable seal 1026. After the biological sample is loaded, card 1000 can be folded along hinge 1014 to form a permanent seal between first body portion 1010 and second body portion 1012. Card 1000 can then be placed in a device for testing. The ease of loaded a biological material into card 1000 and sealing card 1000 for testing making card 1000 suitable for use in the field.

Lid Assembly 1100

Figure 36A:
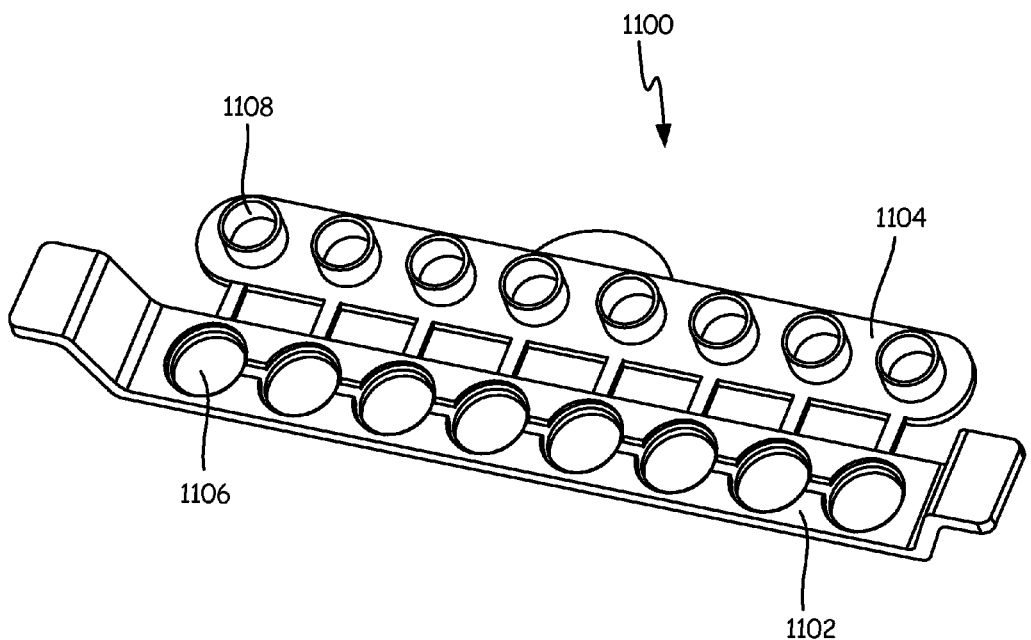
FIG. 36A is a perspective view of a lid assembly.
Figure 36B:
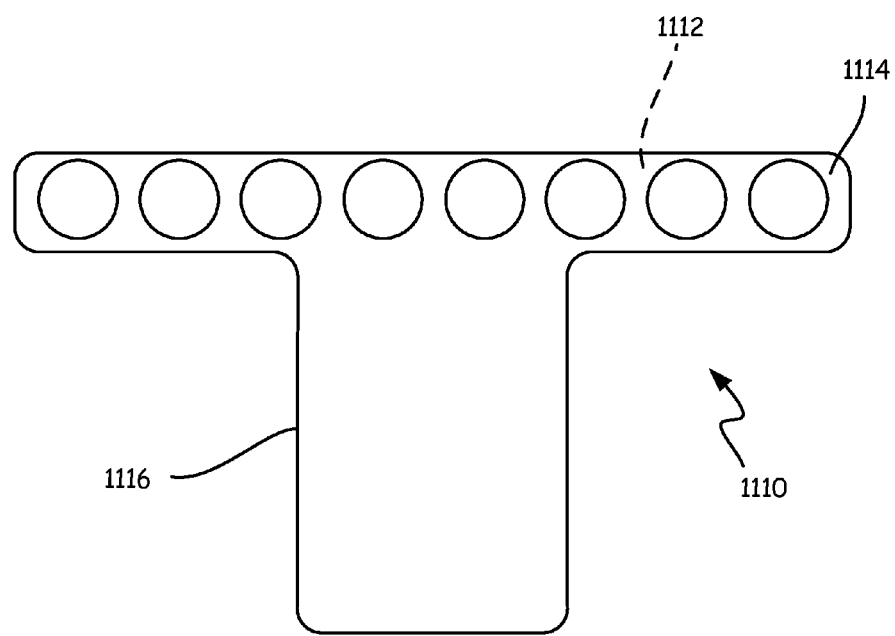
FIG. 36B is a top view of a seal that can be used with the lid assembly.

FIG. 36A is a perspective view of lid assembly 1100. FIG. 36B is a top view of seal portion 1110 that can be used with lid assembly 1100. Lid assembly 1100 includes base portion 1102, lid portion 1104, apertures 1106, and flanges 1108. Seal portion 1110 includes permanent seal 1112, backing 1114, and tab 1116.

Lid assembly 1100 includes base portion 1102 and lid portion 1104. Lid portion 1104 is attached to base portion 1102 with a plurality of hinge members so that lid portion 1104 can be folded along the hinge members towards base portion 1102. Base portion 1102 includes a plurality of apertures 1106. Each aperture 1106 is sized to fit on a standard tube so that base portion 1102 can be attached to a tube array. Lid portion 1104 includes a plurality of flanges 1108. Each flange 1108 is sized to be positioned in a standard tube so that lid portion 1104 can be folded over base portion 1102 and each flange 1108 can be placed in one tube in the tube array to seal the tubes.

Also included with lid assembly 1100 is seal portion 1110. Seal portion 1110 includes permanent seal 1112, backing 1114, and tab 1116. Permanent seal 1112 forms a first layer of seal portion 1110 and backing 1114 is positioned over permanent seal 1112 to form a second layer. Seal portion 1110 can be placed on base portion 1102 of lid assembly 1100 so that permanent seal 1112 is positioned on base portion 1102 and backing 1114 is positioned on a top side of permanent seal 1112. Backing 1114 is capable of being removed from permanent seal 1112 by peeling backing 1114 off of permanent seal 1112. Tab 1116 extends outward from a first side of backing 1114. Tab 1116 is a rectangular shape that can be grasped by a user to position seal portion 1110 on base portion 1102 of lid assembly 1100. A machine readable code can also be printed on tab 1116. When the tube array carrying lid assembly 1100 and seal portion 1110 is placed in a device for testing, the device can scan the machine readable code on tab 1116. The machine readable code can indicate what test is to be run, including information about end point call algorithms and reaction mixture traceability information, among other information.

When seal portion 1110 is positioned on base portion 1102 of lid assembly 1100, lid portion 1104 can be folded onto base portion 1102 when backing 1114 is on seal portion 1110. This will form a mechanical seal between base portion 1102 and lid portion 1104. When backing 1114 is removed, permanent seal 1112 will be exposed. Lid portion 1104 can then be folded onto base portion 1102 to form a permanent seal between base portion 1102 and lid portion 1104.

Using a standard tube array is advantageous, as the tube array can be used with devices that are already available on the market. One issue that arises when using a standard tube array is that the lid portion of the tube array can be removed either intentionally or accidentally. This poses concerns with contamination of the biological sample in the tube array. Lid assembly 1100 is thus advantageous, as it allows a user to create a permanent seal with a standard tube array. Lid assembly 1100 can be closed over backing 1114 of seal portion 1110 to form a mechanical seal that can be opened and closed when the tube array is being prepared for testing. When a biological sample in placed in the tube array, backing 1114 can be removed to expose permanent seal 1112. When lid assembly 1100 is closed over permanent seal 1112, the tube array will be permanently sealed. This eliminates concerns about contamination of the biological sample in the tube array, as it would be difficult to remove lid assembly 1100 from the tube array.

Figure 37A:
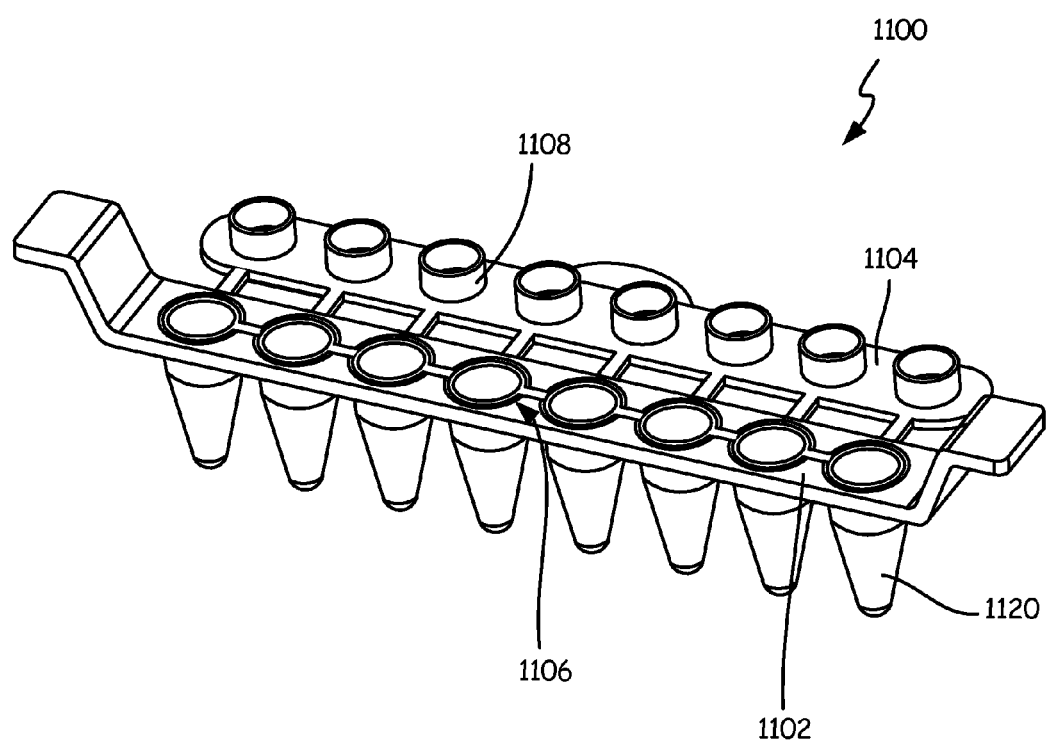
FIG. 37A is a perspective view of the lid assembly attached to an array of sample tubes.
Figure 37B:
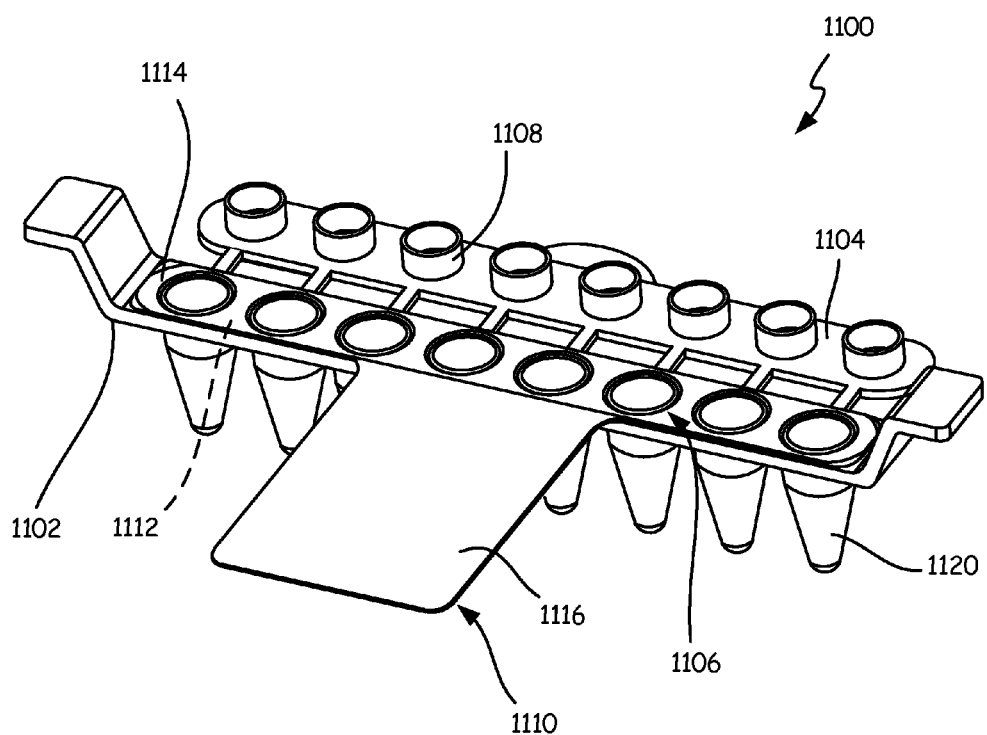
FIG. 37B is a perspective view of the lid assembly with the seal applied to the lid assembly.
Figure 37C:
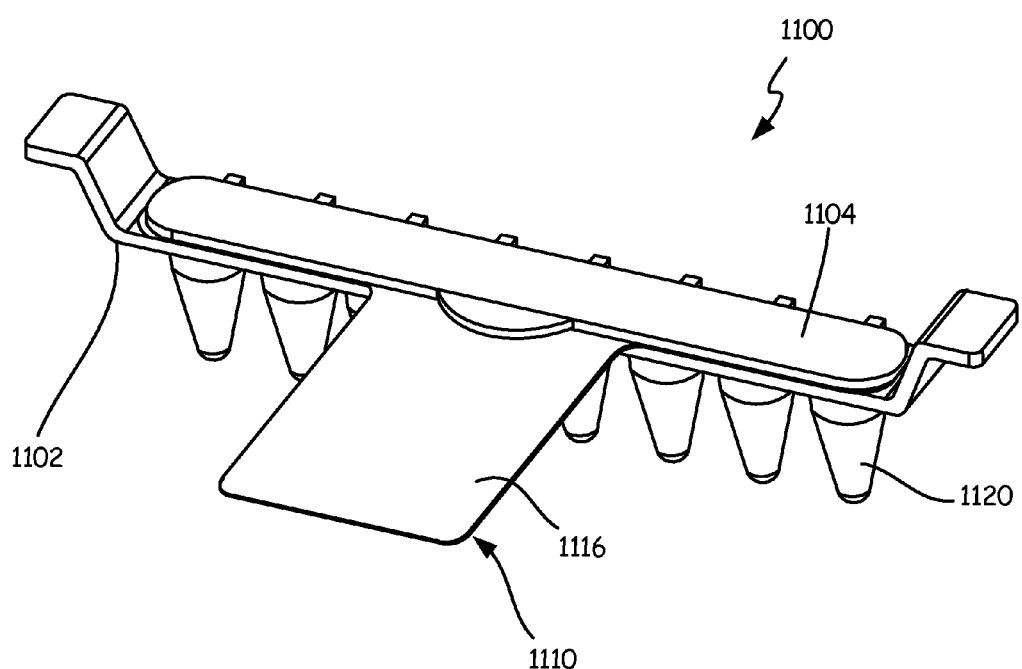
FIG. 37C is a perspective view of the lid assembly in a closed position over the seal.
Figure 37D:
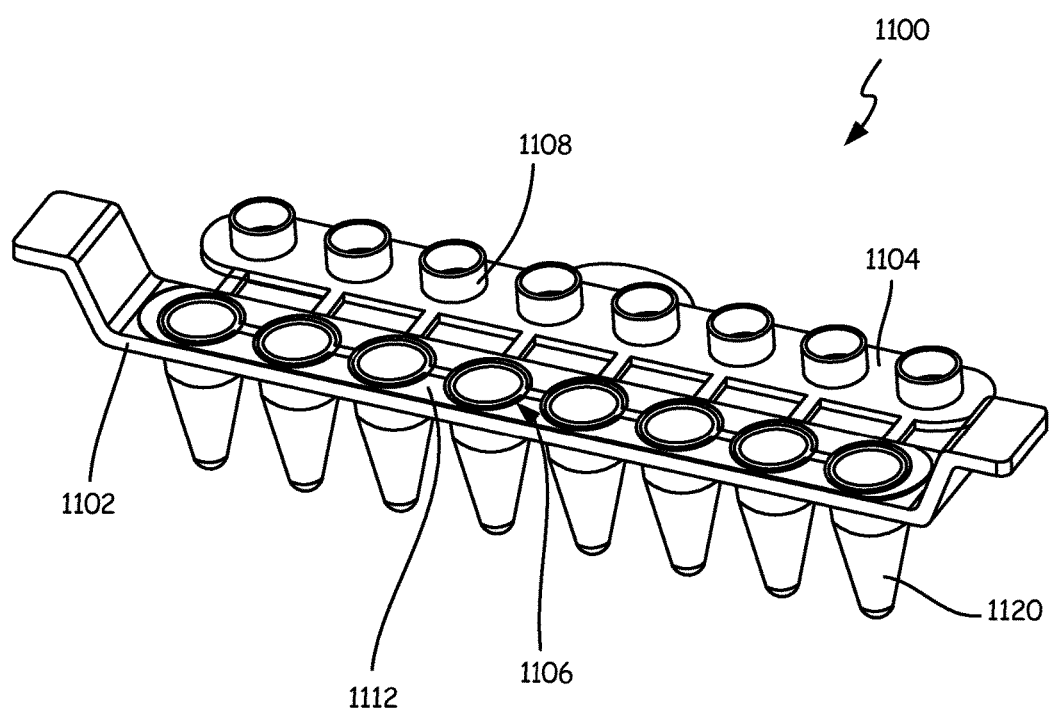
FIG. 37D is a perspective view of the lid assembly opened and a backing removed from the seal.
Figure 37E:
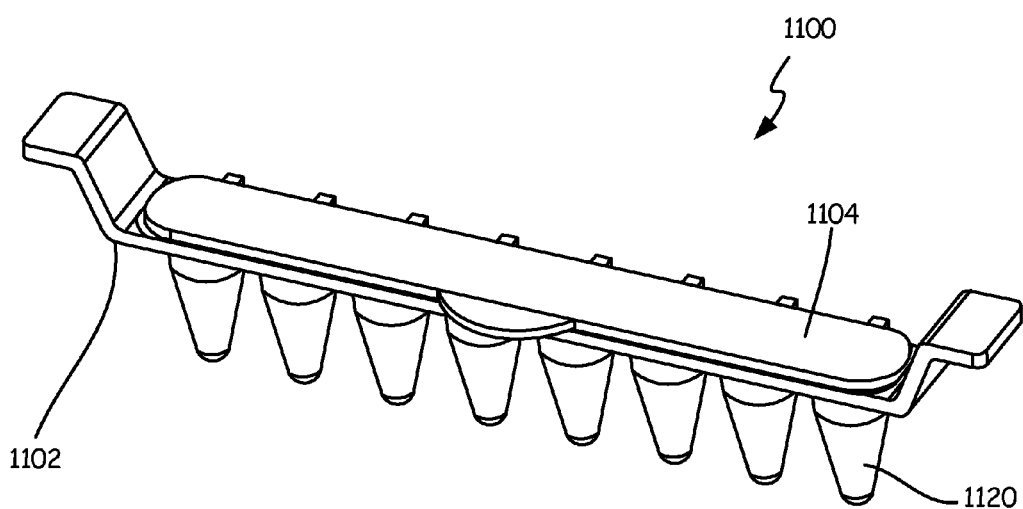
FIG. 37E is a perspective view of the lid assembly in a closed position to form a seal with the permanent seal.

FIG. 37A is a perspective view of lid assembly 1100 attached to tube array 1120. FIG. 37B is a perspective view of lid assembly 1100 with seal portion 1110 applied to lid assembly 1100. FIG. 37C is a perspective view of lid assembly 1100 in a closed position over seal portion 1110. FIG. 37D is a perspective view of lid assembly 1100 opened and backing 1114 removed from seal portion 1110. FIG. 37E is a perspective view of lid assembly 1100 in a closed position to form a seal with permanent seal 1112. Lid assembly 1100 includes base portion 1102, lid portion 1104, apertures 1106, and flanges 1108. Seal portion 1110 includes permanent seal 1112, backing 1114, and tab 1116. Also shown is tube array 1120.

Lid assembly 1100 is capable of being positioned on tube array 1120. Tube array 1120 is a standard tube array that is readily available on the market. Lid assembly 1100 includes base portion 1102 and lid portion 1104. Lid portion 1104 is attached to base portion 1102 with a plurality of hinge members so that lid portion 1104 can be folded along the hinge members towards base portion 1102. Base portion 1102 includes a plurality of apertures 1106. Each aperture 1106 is sized to fit on a standard tube so that base portion 1102 can be attached to tube array 1120. Lid portion 1104 includes a plurality of flanges 1108. Each flange 1108 is sized to be positioned in a standard tube so that lid portion 1104 can be folded over base portion 1102 and flanges 1108 can be placed in tubes in tube array 1120 to seal the tubes.

Also included with lid assembly 1100 is seal portion 1110. Seal portion 1110 includes permanent seal 1112, backing 1114, and tab 1116. Permanent seal 1112 forms a first layer of seal portion 1110 and backing 1114 is positioned over permanent seal 1112 to form a second layer. Seal portion 1110 can be placed on base portion 1102 of lid assembly 1100 so that permanent seal 1112 is positioned on base portion 1102 and backing 1114 is positioned on a top side of permanent seal 1112. Backing 1114 is capable of being removed from permanent seal 1112 by peeling backing 1114 off of permanent seal 1112. Tab 1116 extends outward from a first side of backing 1114. Tab 1116 is a rectangular shape that can be grasped by a user to position seal portion 1110 on base portion 1102 of lid assembly 1100.

To prepare tube array 1120 for testing, a biological material needs to be placed in each of the tubes in tube array 1120 and tube array 1120 needs to be sealed. To do this, a user first obtains tube array 1120 and lid assembly 1100. Lid assembly 1100 can be connected to tube array 1120 by placing apertures 1106 of lid assembly 1100 around each of the tubes in tube array 1120, as seen in FIG. 37A. Apertures 1106 form an interference fit with the tubes in tube array 1120 to hold lid assembly 1100 on tube array 1120. Further, in alternate embodiments, apertures 1106 and the tubes in tube array 1120 can have protrusions so that lid assembly 1100 will snap onto tube array 1120. Tube array 1120 is placed in apertures 1106 of lid assembly 1100 so that when lid assembly 1100 is closed, the members connecting the tubes in tube array 1120 are positioned between base portion 1102 and lid portion 1104. This prevents lid assembly 1100 from being removed from tube array 1120 after lid assembly 1100 is permanent sealed. In alternate embodiments, lid assembly 1100 can be welded or bonded onto tube array 1120 prior to the sale of tube array 1120.

After lid assembly 1100 has been placed on tube array 1120, seal portion 1110 can be placed on base portion 1102 of lid assembly 1100. Seal portion 1110 includes permanent seal 1112 as a first layer and backing 1114 as a second layer. Permanent seal 1112 will be placed on base portion 1102 of lid assembly 1100 and backing 1114 will face upwards from base portion 1102, as seen in FIG. 37B.

After seal portion 1110 has been placed on base portion 1102 of lid assembly 1100, a reaction mixture can be placed in each of the tubes in tube array 1120. The reaction mixture will typically be pipetted into each of the tubes in tube array 1120. After the reaction mixture is dispensed, it can be lyophilized. Lyophilization will dry down the reaction mixture. After the reaction mixture is lyophilized, lid portion 1104 of lid assembly 1100 can be folded over base portion 1102 and seal portion 1110. Flanges 1108 of lid portion 1104 can be inserted into one of each of the tubes in tube array 1120. Lid portion 1104 will come into contact with backing 1114 of seal portion 1110. This will form a mechanical seal between lid portion 1104 and base portion 1102 of lid assembly 1100, as seen in FIG. 37C. Tube array 1120 can then be stored until it is needed to test a biological material. Further, lid assembly 1100 can be opened and closed over backing 1114 to provide access to tube array 1120.

When a biological material is to be placed in tube array 1120 for testing, lid assembly 1100 can be opened by separating lid portion 1104 from base portion 1102. This will expose each of the tubes in tube array 1120. A biological material can then be dispensed into each of the tubes in tube array 1120, which is usually done with pipetting. The biological material is typically added to tube array 1120 in liquid form and can be mixed with the reaction mixture that was previously placed in tube array 1120. After the biological material has been added to tube array 1120, backing 1114 and tab 1116 can be removed from tube array 1120, as seen in FIG. 37D. This will expose permanent seal 1112. Tab 1116 can have a machine readable code printed on it. A user may retain tab 1116 to be scanned by a testing device before disposing of tab 1116.

After permanent seal 1112 has been exposed, lid portion 1104 of lid assembly 1100 can be folded over base portion 1102 of lid assembly 1100. Flanges 1108 on lid portion 1104 can be placed in each of the tubes in tube array 1120. Lid portion 1104 of lid assembly 1100 will come into contact with permanent seal 1112, which will form a permanent seal between lid portion 1104 and base portion 1102, as seen in FIG. 37E. Tube array 1100 and lid assembly 1100 can then be placed in a device to undergo nucleic acid amplification and testing.

Lid assembly 1100 is advantageous, as it allows a user to permanently seal a standard array of tubes. Using a standard array of tubes allows a user to test a biological sample using devices that are already available on the market. Placing lid assembly 1100 on a standard array of tubes allows a user to place a reaction mixture in the tubes and then close the tubes over seal portion 1110, including backing 1114, until the tubes are to be used for testing. At this point, the tubes can be opened and a biological sample can be placed in them. Backing 1114 can then be removed and lid assembly 1100 can be closed over permanent seal 1112. This permanently seals the array of tubes and prevents contamination of the biological sample in the tubes.

Sample Holder 1200

Figure 38A:
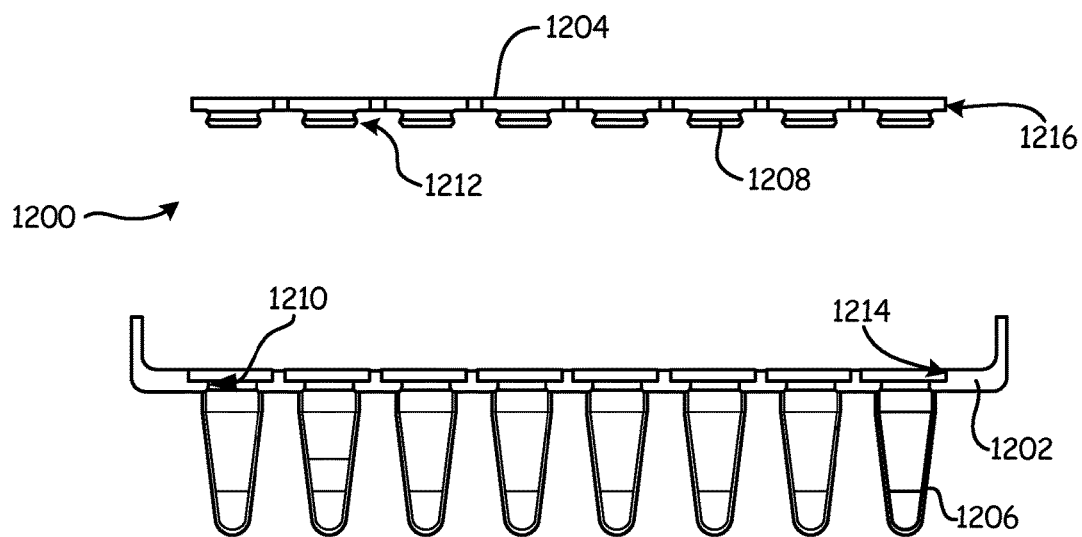
FIG. 38A is a front view of a sample holder including a tube array and a lid array.
Figure 38B:
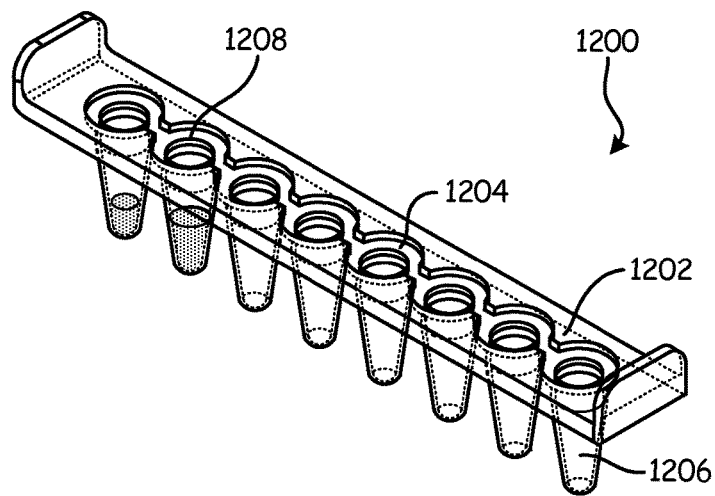
FIG. 38B is a perspective view of the sample holder when the lid array is placed on the tube array.

FIG. 38A is a front view of sample holder 1200 including tube array 1202 and lid array 1204. FIG. 38B is a perspective view of sample holder 1200 when lid array 1204 is placed on tube array 1202. Sample holder 1200 includes tube array 1202 and lid array 1204. Tube array 1202 includes wells 1206, well lips 1210, and tube lip 1214. Lid array 1204 includes flanges 1208, flange lips 1212, and lid lip 1216.

Sample holder 1200 includes tube array 1202 and lid array 1204. Tube array 1202 includes a plurality of wells 1206. Wells 1206 extend downward from a base portion of tube array 1202. Each well 1206 is capable of receiving a reaction mixture and biological material that are to be tested. In the embodiment seen in FIGS. 38A-38B, wells 1206 have a standard shape and configuration. In alternate embodiments, wells 1206 can be any shape that is capable of being tested. Lid array 1204 includes a plurality of flanges 1208. Flanges 1208 extend downward from a base portion of lid array 1204. Lid array 1204 can be placed on tube array 1202 to form sample holder 1200. Each flange 1208 on lid array 1204 can be placed in one well 1206 on tube array 1202 to form a first mechanical seal between tube array 1202 and lid array 1204.

To strengthen the first mechanical seal between tube array 1202 and lid array 1204, flanges 1208 and wells 1206 may include a plurality of protrusions to strengthen the seal between tube array 1202 and lid array 1204. Wells 1206 include well lips 1210 on an upper inside perimeter of each well 1206. Well lips 1210 can include a plurality of protrusions that run along the perimeter of wells 1206. Flanges 1208 include flange lips 1212 on a lower outer perimeter of each flange 1208. Flange lips 1212 can include a plurality of protrusions that run along the perimeter of flanges 1208. When flanges 1208 are placed in wells 1206, flange lips 1212 will come into contact with well lips 1210. The protrusions in both flange lips 1212 and well lips 1210 will form a first mechanical seal. The first mechanical seal is strengthened by the protrusions, as the protrusions make it harder for lid array 1204 to be removed from tube array 1202.

A second mechanical seal can be formed between the base portion of tube array 1202 and the base portion of lid array 1204. The base portion of tube array 1202 includes a recessed area surrounding wells 1206. In the embodiment shown in FIGS. 38A-38B, the recessed area is shaped as a plurality of circles connected to one another down the middle. Lid array 1204 is designed to mimic this shape, so that when lid array 1204 is placed on tube array 1202 it will fit in the recessed area on tube array 1202. This forms the second mechanical seal between tube array 1202 and lid array 1204. This also allows lid array 1204 to fit flush with tube array 1202, which makes it difficult for lid array 1204 to be removed from tube array 1202. In alternate embodiments, the recessed area in tube array 1202 and the shape of lid array 1204 can be any suitable shape.

To strengthen the second mechanical seal between tube array 1202 and lid array 1204, tube array 1202 and lid array 1204 may include a plurality of protrusions to strengthen the seal between the base portion of tube array 1202 and the base portion of lid array 1204. Tube array 1202 includes tube lip 1214 on an upper inside perimeter of the recessed area of tube array 1202. Tube lip 1214 can include a plurality of protrusions that run along the perimeter of the recessed portion of tube array 1202. Lid array 1204 includes lid lip 1216 on an outer perimeter of the base portion of lid array 1204. Lid lip 1216 can include a plurality of protrusions that run along the perimeter of the base portion of lid array 1204. When lid array 1204 is placed on tube array 1202, lid lip 1216 will come into contact with tube lip 1214. The protrusions in both lid lip 1216 and tube lip 1214 will form a second mechanical seal. The second mechanical seal is strengthened by the protrusions, as the protrusions make it harder for lid array 1204 to be removed from tube array 1202.

Sample holder 1200 is advantageous, as lid array 1204 can be placed securely on tube array 1202. A problem that exists with previous tube arrays is that the lid can easily come off of the tube array, either intentionally or accidentally. This presents concerns with contamination of the materials in the tube array. To prevent this from happening, sample holder 1200 provides a double-seal mechanism. The first seal is formed between flanges 1208 of lid array 1204 and wells 1206 of tube array 1202. A second seal is formed between a base portion of lid array 1204 and a base portion of tube array 1202. This double-seal mechanism is advantageous, as it is harder for lid array 1204 to be removed from tube array 1202. Further, both the first mechanical seal and the second mechanical seal are strengthened by protrusions that engage lid array 1204 with tube array 1202, making it harder for lid array 1204 to be removed from tube array 1202. In alternate embodiments, the second seal could be an adhesive seal or any other suitable seal.

Further, lid array 1204 is placed into a recessed area in the base portion of tube array 1202. This allows lid array 1204 to sit flush with tube array 1202 and make it difficult for lid array 1204 to be removed from tube array 1202, both intentionally and accidentally. Making it this difficult for lid array 1204 to be removed from tube array 1202 is advantageous, as it alleviates concerns about contamination of the material in tube array 1202.

Figure 39A:
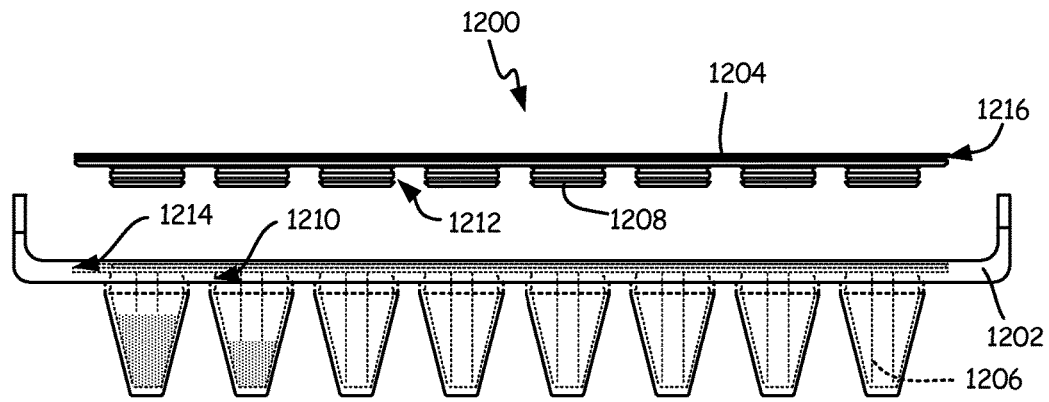
FIG. 39A is a front view of a sample holder including a tube array and a lid array.
Figure 39B:
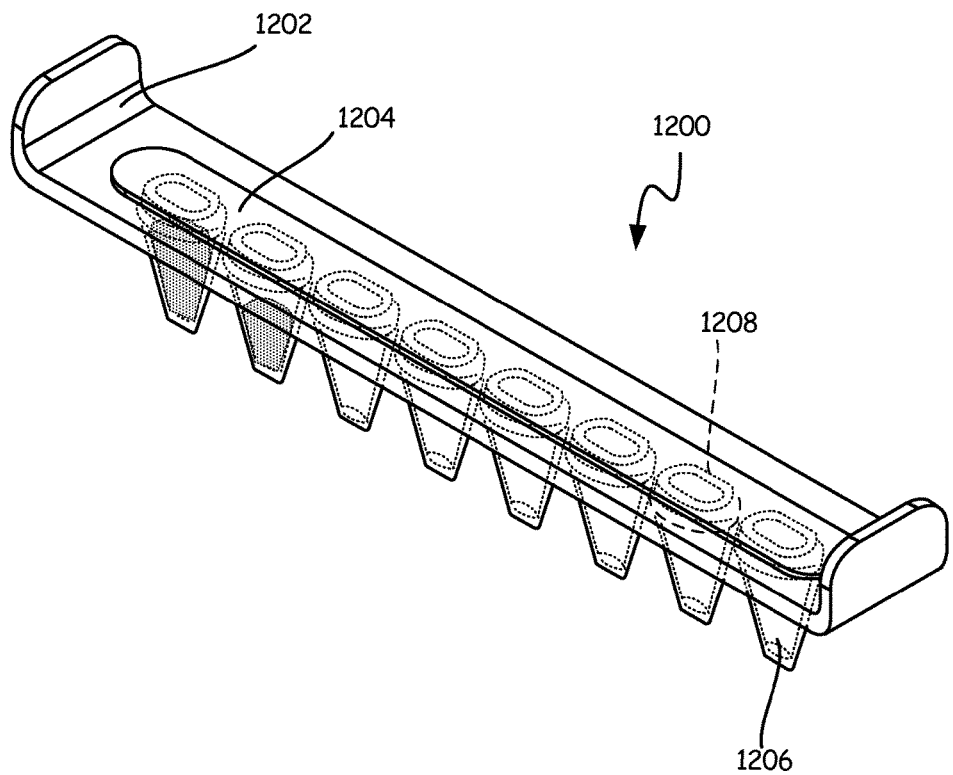
FIG. 39B is a perspective view of the sample holder when the lid array is placed on the tube array.
Figure 39C:
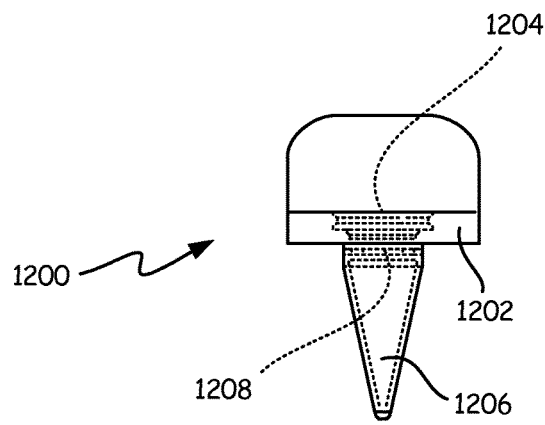
FIG. 39C is a side view of the sample holder when the lid array is placed on the tube array.
Figure 39D:
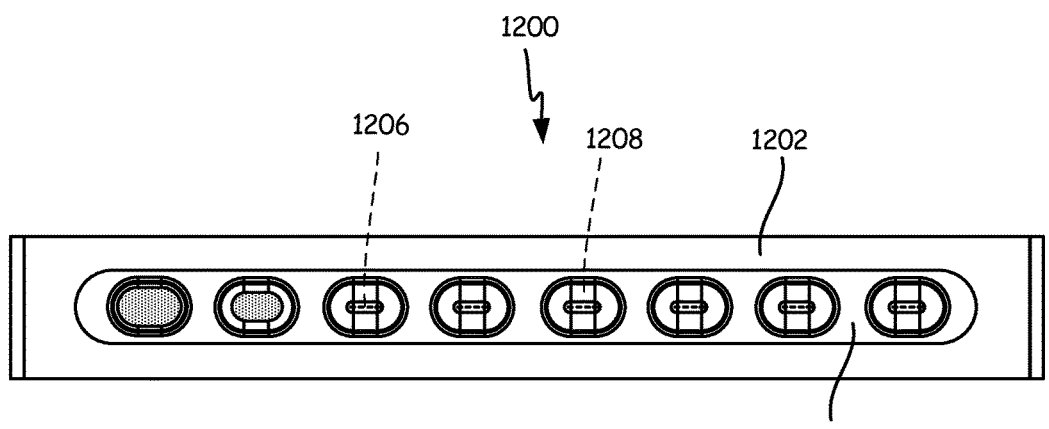
FIG. 39D is a top view of the sample holder.

FIG. 39A is a front view of sample holder 1200 including tube array 1202 and lid array 1204. FIG. 39B is a perspective view of sample holder 1200 when lid array 1204 is placed on tube array 1202. FIG. 39C is a side view of sample holder 1200 when lid array 1204 is placed on tube array 1202. FIG. 39D is a top view of sample holder 1200. Sample holder 1200 includes tube array 1202 and lid array 1204. Tube array 1202 includes wells 1206, well lips 1210, and tube lip 1214. Lid array 1204 includes flanges 1208, flange lips 1212, and lid lip 1216.

Sample holder 1200 includes tube array 1202 and lid array 1204. Tube array 1202 includes a plurality of wells 1206. Wells 1206 extend downward from a base portion of tube array 1202. Each well 1206 is capable of receiving a reaction mixture and biological material that are to be tested. In the embodiment seen in FIGS. 39A-39D, wells 1206 have an oblong oval shape with a first flat side and a second flat side. This shape allows the biological sample in wells 1206 to be read through both the first flat side and the second flat side.

Lid array 1204 includes a plurality of flanges 1208. Flanges 1208 extend downward from a base portion of lid array 1204. Lid array 1204 can be placed on tube array 1202 to form sample holder 1200. Each flange 1208 on lid array 1204 can be placed in one well 1206 on tube array 1202 to form a first mechanical seal between tube array 1202 and lid array 1204.

To strengthen the first mechanical seal between tube array 1202 and lid array 1204, flanges 1208 and wells 1206 may include a plurality of protrusions to strengthen the seal between tube array 1202 and lid array 1204. Wells 1206 include well lips 1210 on an upper inside perimeter of each well 1206. Well lips 1210 can include a plurality of protrusions that run along the perimeter of wells 1206. Flanges 1208 include flange lips 1212 on a lower outer perimeter of each flange 1208. Flange lips 1212 can include a plurality of protrusions that run along the perimeter of flanges 1208. When flanges 1208 are placed in wells 1206, flange lips 1212 will come into contact with wells lips 1210. The protrusions in both flange lips 1212 and well lips 1210 will form a first mechanical seal. The first mechanical seal is strengthened by the protrusions, as the protrusions make it harder for lid array 1204 to be removed from tube array 1202.

A second mechanical seal can be formed between the base portion of tube array 1202 and the base portion of lid array 1204. The base portion of tube array 1202 includes a recessed area surrounding wells 1206. In the embodiment shown in FIGS. 39A-39D, the recessed area has a rectangular shape with rounded corners. Lid array 1204 is designed to mimic this shape, so that when lid array 1204 is placed on tube array 1202 it will fit in the recessed area on tube array 1202. This forms the second mechanical seal between tube array 1202 and lid array 1204. This also allows lid array 1204 to fit flush with tube array 1202, which makes it difficult for lid array 1204 to be removed from tube array 1202.

To strengthen the second mechanical seal between tube array 1202 and lid array 1204, tube array 1202 and lid array 1204 may include a plurality of protrusions to strengthen the seal between the base portion of tube array 1202 and the base portion of lid array 1204. Tube array 1202 includes tube lip 1214 on an upper inside perimeter of the recessed area of tube array 1202. Tube lip 1214 can include a plurality of protrusions that run along the perimeter of the recessed area of tube array 1202. Lid array 1204 includes lid lip 1216 on an outer perimeter of the base portion of lid array 1204. Lid lip 1216 can include a plurality of protrusions that run along the perimeter of the base portion of lid array 1204. When lid array 1204 is placed on tube array 1202, lid lip 1216 will come into contact with tube lip 1214. The protrusions in both lid lip 1216 and tube lip 1214 will form a second mechanical seal. The second mechanical seal is strengthened by the protrusions, and the protrusions make it harder for lid array 1204 to be removed from tube array 1202.

Sample holder 1200 is advantageous, as it is very difficult to remove lid array 1204 from tube array 1202 either intentionally or accidentally. First, there is a double-seal mechanism between lid array 1204 and tube array 1202. Second, there are protrusions on both lid array 1204 and tube array 1202 that make it difficult for them to be separated. Third, lid array 1204 sits flush with tube array 1202 so that it is very difficult for lid array 1204 to be removed from tube array 1202. Making it hard for lid array 1204 to be removed from tube array 1202 is advantageous, as it alleviates concerns about contamination of the biological sample in tube array 1202.

Sample holder 1200 is further advantageous because of the shape of wells 1206. Wells 1206 have a first flat side and a second flat side. This allows radiation to travel into and out of wells 1206 from either side. The flat sides of wells 1206 provide a wide basis for such radiation to travel into and out of the biological sample in wells 1206.

Figure 40A:
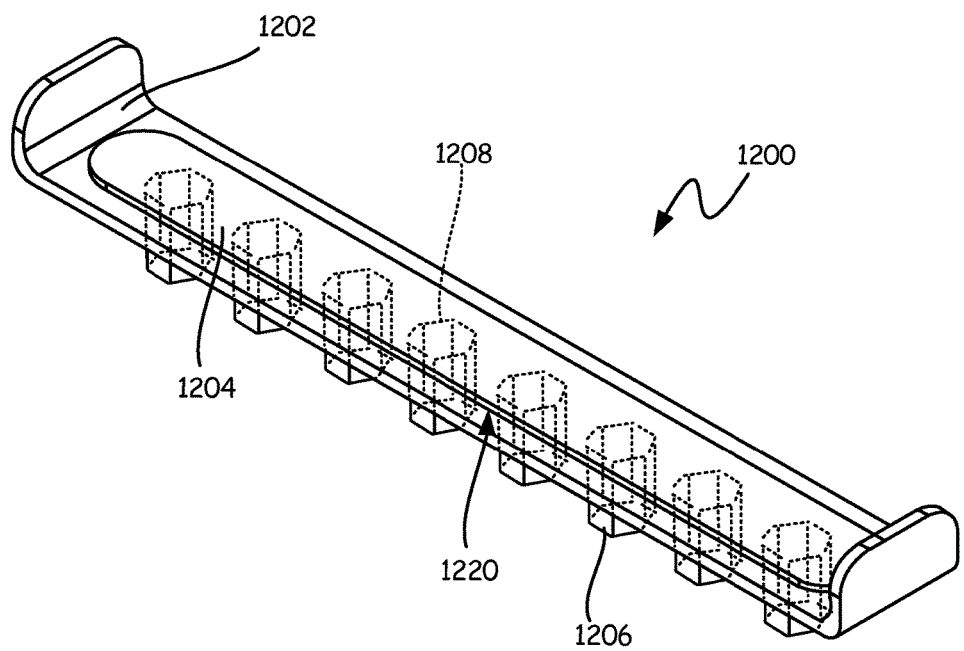
FIG. 40A is a perspective view of a sample holder when a lid array is placed on a tube array.
Figure 40B:
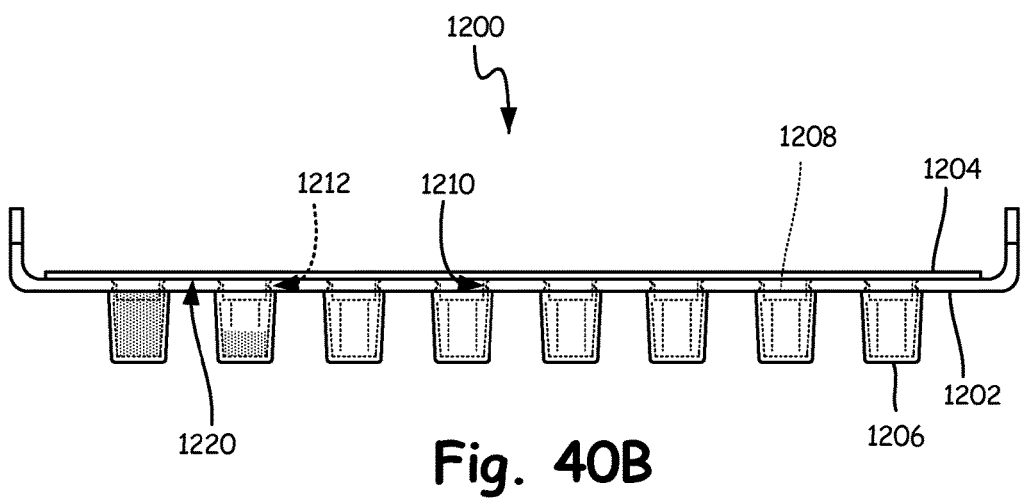
FIG. 40B is a front view of the sample holder when the lid array is placed on the tube array.
Figure 40C:
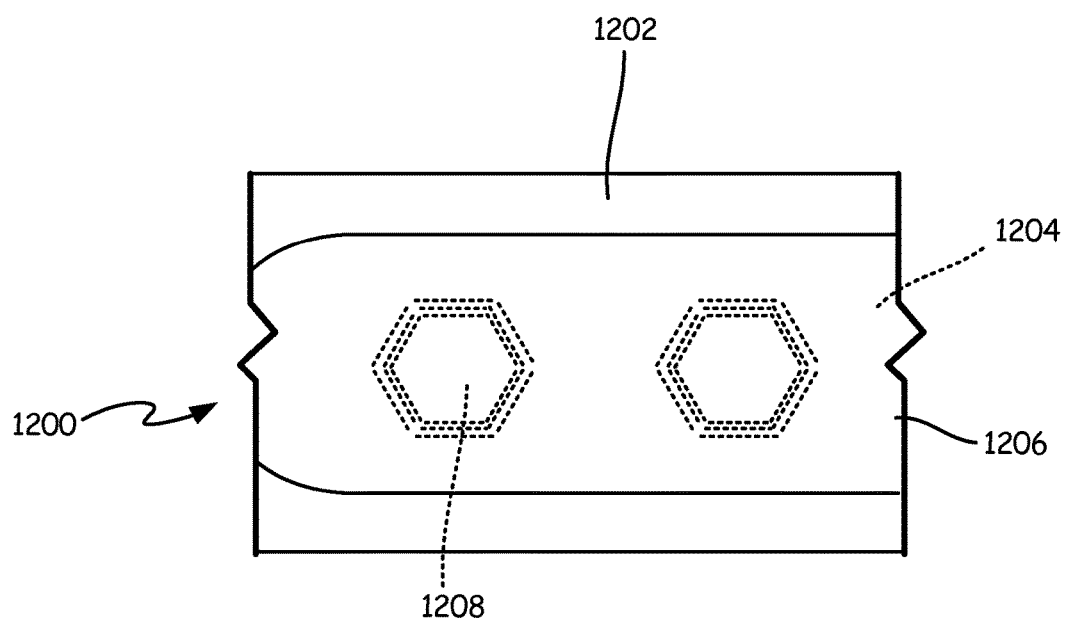
FIG. 40C is a bottom view of the sample holder.

FIG. 40A is a perspective view of sample holder 1200 when lid array 1204 is placed on tube array 1202. FIG. 40B is a front view of sample holder 1200 when lid array 1204 is placed on tube array 1202. FIG. 40C is a bottom view of sample holder 1200. Sample holder 1200 includes tube array 1202 and lid array 1204. Tube array 1202 includes wells 1206, well lips 1210, and tube lip 1214. Lid array 1204 includes flanges 1208, flange lips 1212, and lid lip 1216. Also shown is adhesive 1220.

Sample holder 1200 includes tube array 1202 and lid array 1204. Tube array 1202 includes a plurality of wells 1206. Wells 1206 extend downward from a base portion of tube array 1202. Each well 1206 is capable of receiving a reaction mixture and biological material that are to be tested. In the embodiment seen in FIGS. 40A-40C, wells 1206 have a hexagonal shape with a flat bottom. The hexagonal shape of the wells provides six different sides for each well 1206. This shape allows the biological material in each well 1206 to be read through any of the six sides.

Lid array 1204 includes a plurality of flanges 1208. Flanges 1208 extend downward from a base portion of lid array 1204. Lid array 1204 can be placed on tube array 1202 to form sample holder 1200. Each flange 1208 on lid array 1204 can be placed in one well 1206 on tube array 1202 to form a first mechanical seal between tube array 1202 and lid array 1204.

To strengthen the first mechanical seal between tube array 1202 and lid array 1204, flanges 1208 and wells 1206 may include a plurality of protrusions to strengthen the seal between tube array 1202 and lid array 1204. Wells 1206 include well lips 1210 on an upper inside perimeter of each well 1206. Well lips 1210 can include a plurality of protrusions that run along the perimeter of wells 1206. Flanges 1208 include flange lips 1212 on a lower outer perimeter of each flange 1208. Flange lips 1212 can include a plurality of protrusions that run along the perimeter of flanges 1208. When flanges 1208 are placed in wells 1206, flange lips 1212 will come into contact with well lips 1210. The protrusions in both flange lips 1212 and well lips 1210 will form a first mechanical seal. The first mechanical seal is strengthened by the protrusions, as the protrusions make it harder for lid array 1204 to be removed from tube array 1202.

A second seal can be formed between the base portion of tube array 1202 and the base portion of lid array 1204. When lid array 1204 is placed on tube array 1202, a bottom side of the base portion of lid array 1204 will come into contact with a top side of the base portion of tube array 1202. Adhesive 1220 can be placed between the bottom side of the base portion of lid array 1204 and the top side of the base portion of tube array 1202 to seal lid array 1204 onto tube array 1202. Adhesive 1220 can be any suitable adhesive and can be applied using any suitable process.

Sample holder 1200 is advantageous, as it is very difficult to remove lid array 1204 from tube array 1202 either intentionally or accidentally. There is a double-seal mechanism between lid array 1204 and tube array 1202. The first seal is a mechanical seal and the second seal is an adhesive seal. There are also protrusions on both lid array 1204 and tube array 1202 that make it difficult for them to be separated. Making it hard for lid array 1204 to be removed from tube array 1202 is advantageous, as it alleviates concerns about contamination of the biological sample in tube array 1202.

Sample holder 1200 is further advantageous because of the shape of wells 1206. Wells 1206 have a hexagonal shape with six distinct sides. This allows radiation to travel into and out of wells 1206 from any of the six sides. This allows three different light-emitting diodes to be positioned on three sides of wells 1206 and three photodetectors to be positioned on the remaining three sides of wells 1206. Each light-emitting diode can excite the biological sample in wells 1206 at a different radiation wavelength and each photodetector can detect different radiation wavelengths that are emitted from the biological sample. This allows three different fluorescent dyes to be tested out of wells 1206.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A portable testing device comprising: a housing with an integrated touchscreen display and a receptacle in which a sample holder containing a biological sample and reagent mixture can be placed; an optical assembly positioned in the housing, wherein the optical assembly is configured to amplify and detect a signal from the biological sample and reagent mixture in the sample holder, wherein the optical assembly includes a first excitation filter that extends across at least a portion of the entire-optical assembly and a first emission filter that extends across at least a portion of the entire-optical assembly, and wherein the optical assembly comprises: a sample block in which a sample holder containing a biological sample and reagent mixture can be positioned, the sample block comprises: a plurality of cavities that are shaped to receive the sample holder; and a heating component to heat the biological sample and reagent mixture in the sample holder; a first housing portion positioned on a first side of the sample block, wherein the first excitation filter and the first emission filter are positioned in the first housing portion, and the first housing portion further comprises: a first plurality of light-emitting diodes positioned on a first side of the first excitation filter; a first plurality of photodetectors positioned on a first side of the first emission filter; and a second housing portion positioned on a second side of the sample block, the second housing portion comprises: a second excitation filter positioned in the second housing portion; a second plurality of light-emitting diodes positioned on a first side of the second excitation filter; a second emission filter positioned in the second housing portion; and a second plurality of photodetectors positioned on a first side of the second emission filter; an electronic assembly that is configured to receive data from the optical assembly and transmit it for display on the touchscreen display; and a power supply in the housing to power the portable testing device.

2. The portable testing device of claim 1, wherein the housing of the portable testing device further comprises:
an integrated handle to allow for transport of the device; and
a lid over the receptacle that is movable between an open and closed position.

3. The portable testing device of claim 1, and further comprising:
a machine readable code reader in the housing for reading a machine readable code.

4. The portable testing device of claim 1, wherein the receptacle includes a plurality of cavities that are configured to receive a tube array.

5. The portable testing device of claim 1, wherein the receptacle includes one cavity that is configured to receive a card.

6. The portable testing device of claim 5, wherein the card comprises:
a body portion defining a shape of the card;
a plurality of wells that are integrally formed with the body portion, wherein each well has a first cavity, a second cavity, and a channel connecting the first cavity to the second cavity;
a first permanent seal covering the channel and the second cavity of each of the plurality of wells;
a removable seal covering the first cavity of each of the plurality of wells that can be removed to provide access to each of the plurality of wells; and
a second permanent seal with a removable backing attached to the body portion of the card sample holder, wherein the removable backing can be removed and the second permanent seal can be placed on the body portion of the card to seal the first cavity of each of the plurality of wells.

7. The portable testing device of claim 1, wherein the sample block further comprises: a first plurality of apertures, wherein each aperture extends from a bottom side of the sample block to one of the plurality of cavities; a second plurality of apertures, wherein each aperture extends from a first side of the sample block to one of the plurality of cavities; a third plurality of apertures, wherein each aperture extends from a bottom side of the sample block to one of the plurality of cavities; and a fourth plurality of apertures, wherein each aperture extends from a second side of the sample block to one of the plurality of cavities.

8. The portable testing device of claim 7, and further comprising:
a plurality of lenses, wherein one lens is positioned in each of the second plurality of apertures in the sample block.

9. The portable testing device of claim 7, wherein the first housing portion further comprises:
a first plurality of passages, wherein each of the first plurality of passages in the first housing portion is aligned with one of the first plurality of apertures in the sample block, and wherein the first plurality of passages are positioned on a second side of the first excitation filter; and
a second plurality of passages, wherein each of the second plurality of passages in the first housing portion is aligned with one of the second plurality of apertures in the sample block, and wherein the second plurality of passage are positioned on a second side of the first emission filter.

10. The portable testing device of claim 9, wherein the second housing portion further comprises:
a third plurality of passages, wherein each of the third plurality of passages in the second housing portion is aligned with one of the third plurality of apertures in the sample block, and wherein the third plurality of passages are positioned on a second side of the second excitation filter; and
a fourth plurality of passages, wherein each of the fourth plurality of passages in the second housing portion is aligned with one of the fourth plurality of apertures in the sample block, and wherein the fourth plurality of passages are positioned on a second side of the second emission filter.

11. The portable testing device of claim 10, wherein: the first plurality of passages and the first plurality of apertures are positioned so that light from each of the first plurality of light-emitting diodes passes through the first excitation filter, one of the first plurality of passages, and one of the first plurality of apertures into the biological sample and reagent mixture in the sample holder; and the third plurality of passage and the third plurality of apertures are positioned so that light from each of the second plurality of light-emitting diodes passes through the second excitation filter, one of the third plurality of passages, and one of the third plurality of apertures into the biological sample and reagent mixture in the sample holder.

12. The portable testing device of claim 11, wherein:
the second plurality of passages and the second plurality of apertures are positioned so that emissions from the biological sample and reagent mixture in the sample holder passes through each of the second plurality of apertures, each of the second plurality of passages, and the first emission filter to the first plurality of photodetectors; and
the fourth plurality of passages and the fourth plurality of apertures are positioned so that emissions from the biological sample and reagent mixture in the sample holder passes through each of the fourth plurality of apertures, each of the fourth plurality of passages, and the second emission filter to the second plurality of photodetectors.

13. The portable testing device of claim 1, wherein:
the first plurality of light-emitting diodes are bi-color light-emitting diodes;
the first excitation filter is a dual bandpass filter;
the first emission filter is a dual bandpass filter;
the second plurality of light-emitting diodes are bi-color light-emitting diodes;
the second excitation filter is a dual bandpass filter; and
the second emission filter is a dual bandpass filter.

14. The portable testing device of claim 1, wherein:
the first plurality of light-emitting diodes emit radiation at a predetermined cycle rate of 1.54 kHz; and
the second plurality of light-emitting diodes emit radiation at a predetermined cycle rate of 1.54 kHz.

* * * * *